US012766250B2

(12) United States Patent
Tschirren et al.

(10) Patent No.: US 12,766,250 B2
(45) Date of Patent: Oct. 20, 2026

(54) NEEDLE INSERTION MECHANISM FOR AN INJECTION OR INFUSION DEVICE

(71) Applicant: Ypsomed AG, Burgdorf (CH)

(72) Inventors: Markus Tschirren, Burgdorf (CH); Michael Dobler, Balsthal (CH); Andres Mellenberger, Koppigen (CH)

(73) Assignee: Ypsomed AG, Burgdorf (CH)

( * ) Notice: Subject to any disclaimer, the term of this patent is extended or adjusted under 35 U.S.C. 154(b) by 376 days.

(21) Appl. No.: 18/615,294

(22) Filed: Mar. 25, 2024

(65) Prior Publication Data

US 2024/0269376 A1 Aug. 15, 2024

Related U.S. Application Data

(63) Continuation of application No. PCT/EP2022/071926, filed on Aug. 4, 2022.

(30) Foreign Application Priority Data

Sep. 27, 2021 (EP) .................................... 21199024

(51) Int. Cl.
*A61M 5/142* (2006.01)

(52) U.S. Cl.
CPC ................... *A61M 5/14248* (2013.01); *A61M 2005/14256* (2013.01); *A61M 2205/103* (2013.01);
(Continued)

(58) Field of Classification Search
CPC ......... A61M 2005/14252; A61M 2005/14256; A61M 2005/1585; A61M 2205/121;
(Continued)

(56) References Cited

U.S. PATENT DOCUMENTS 7,815,607 B2 * 10/2010 Rutti ..................... A61M 5/158
604/157

FOREIGN PATENT DOCUMENTS

EP 1970084 A1 9/2008
EP 3501576 A1 * 6/2019 .......... A61M 5/3234
(Continued)

OTHER PUBLICATIONS

Extended European Search Report issued in European Patent Application No. 21199024.7, issued on Mar. 23, 2022, 10 pages.
(Continued)

*Primary Examiner* — Rebecca E Eisenberg
(74) *Attorney, Agent, or Firm* — Dorsey & Whitney LLP

(57) ABSTRACT

Needle insertion mechanisms for an injection device include a housing, a needle holder holding a needle, a slider moveable from a first position retaining the needle holder in a retracted position towards a second position allowing movement of the needle holder to an inserted position. An intermediate member positioned between the needle holder and the slider is moveable from a blocked position to a release position releasing the needle holder for movement to the inserted position. A biased gearing between the intermediate member and the needle holder biases the intermediate member towards the release position. A lock between the intermediate member and the slider is configured to lock the intermediate member in the blocked position against the bias of the gearing. Movement of the slider towards the second position unlocks the lock and the biased gearing moves the intermediate member into the release position thereby releasing the needle holder.

19 Claims, 30 Drawing Sheets

(52) U.S. Cl.
CPC ... *A61M 2205/121* (2013.01); *A61M 2205/13* (2013.01); *A61M 2205/3327* (2013.01); *A61M 2205/583* (2013.01); *A61M 2205/8206* (2013.01)

(58) Field of Classification Search
CPC .......... A61M 5/14244; A61M 5/14248; A61M 2005/1426
See application file for complete search history.

(56) References Cited

FOREIGN PATENT DOCUMENTS

| | | | | |
|---|---|---|---|---|
| EP | 3603700 | A1 | 2/2020 | |
| EP | 3862037 | A1 | 8/2021 | |
| EP | 4154926 | A1 | 3/2023 | |
| WO | WO-2018024625 | A1 * | 2/2018 | ........ A61M 5/14248 |
| WO | 2023046348 | A1 | 3/2023 | |

OTHER PUBLICATIONS

International Search Report and Written Opinion issued in International Application No. PCT/EP2022/071926, mailed on Nov. 4, 2022, 12 pages.

* cited by examiner

Fig. 3a, b, c
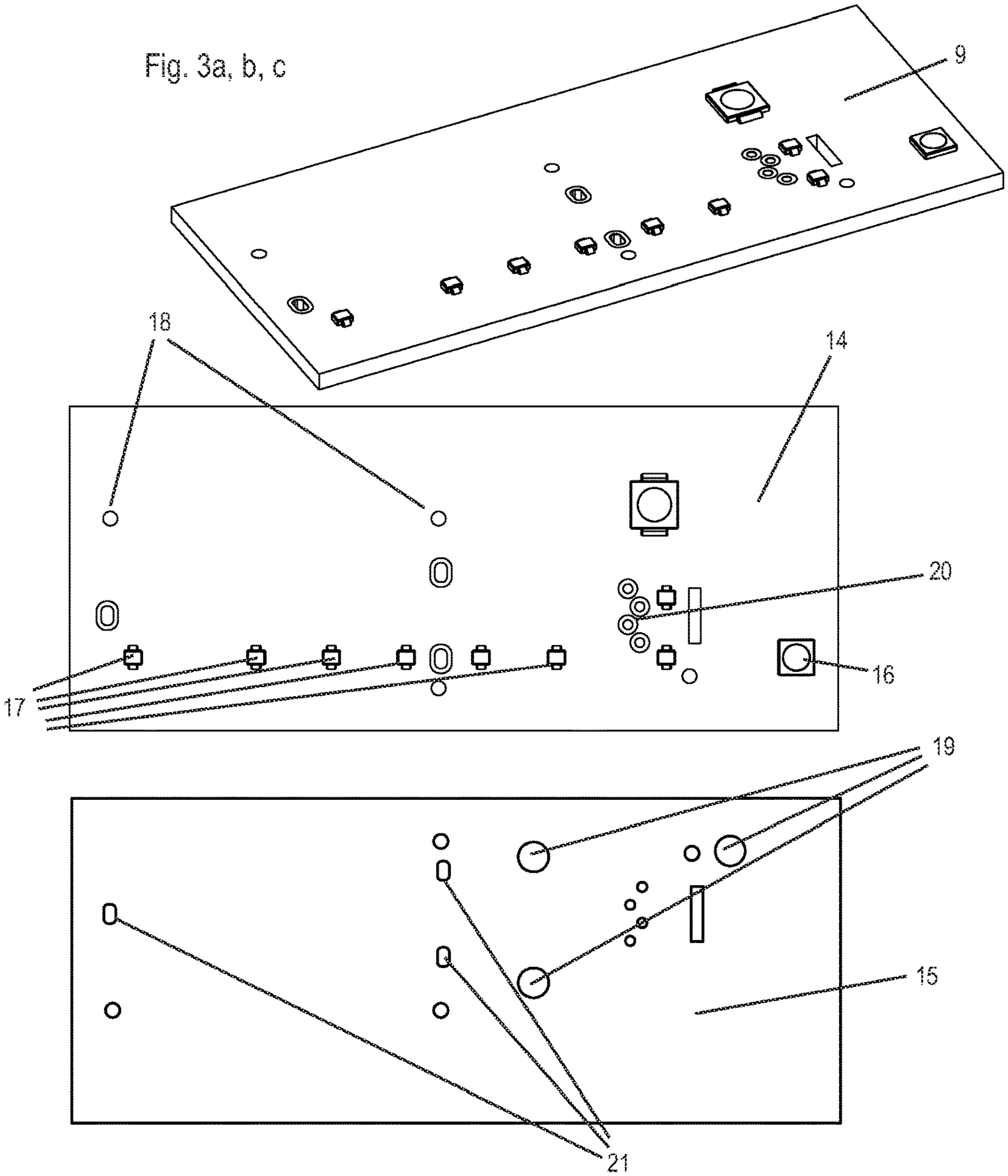
Fig. 3d
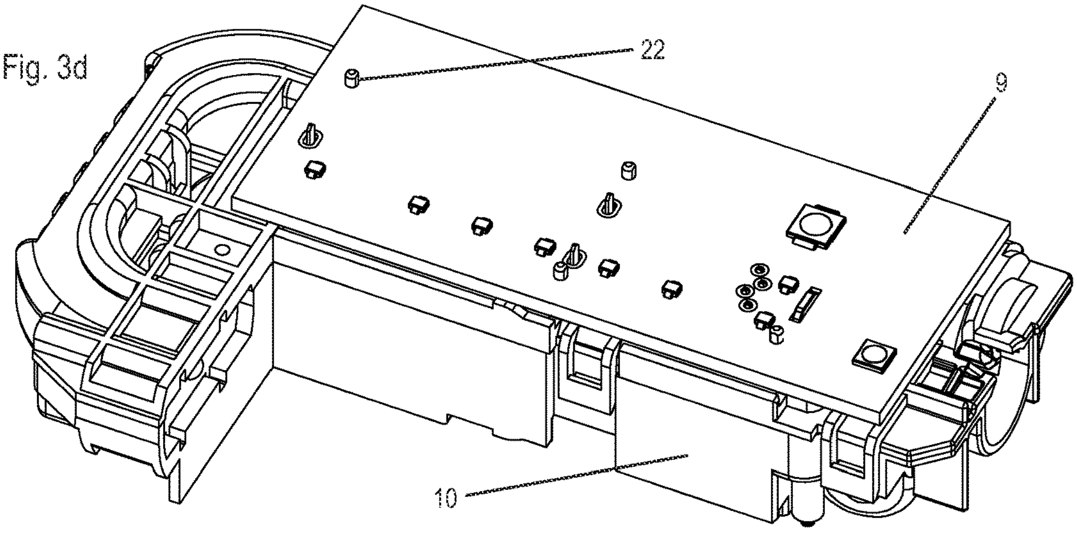

Fig. 8n
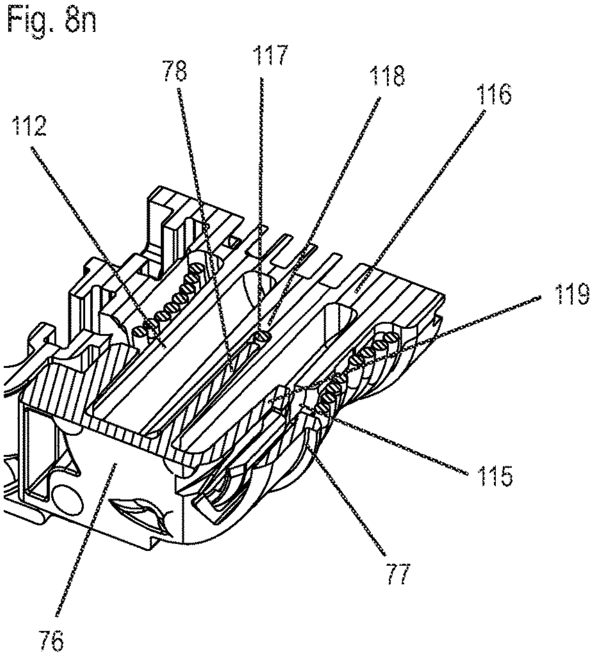
Fig. 8o
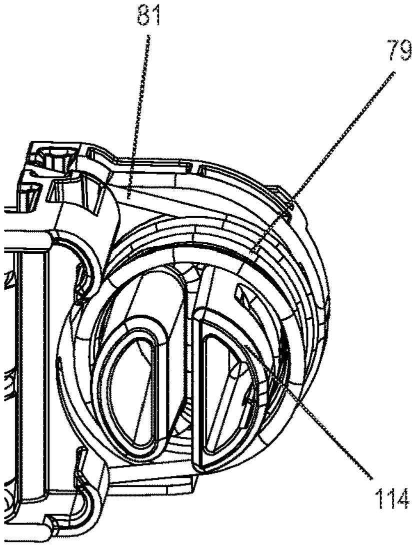
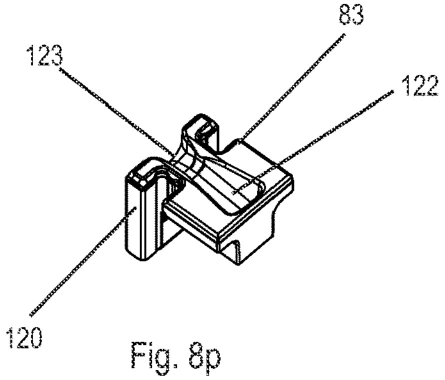
Fig. 8p
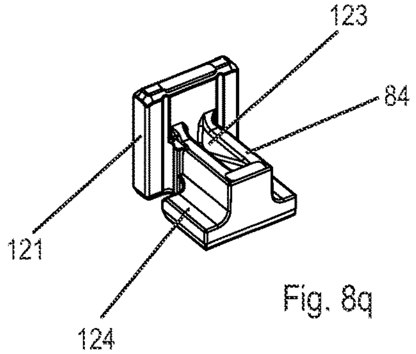
Fig. 8q
Fig. 8r
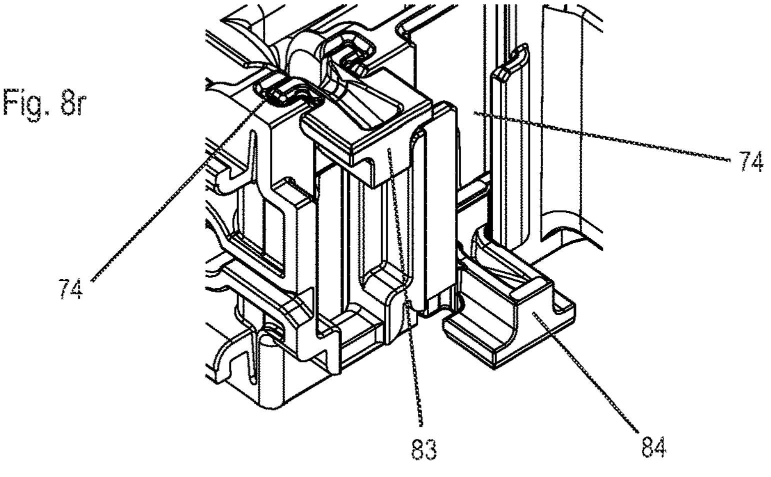

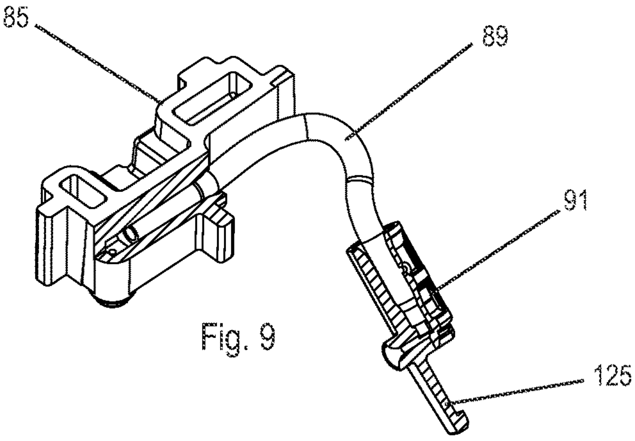
Fig. 9
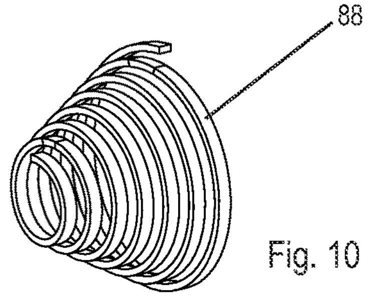
Fig. 10
Fig. 11
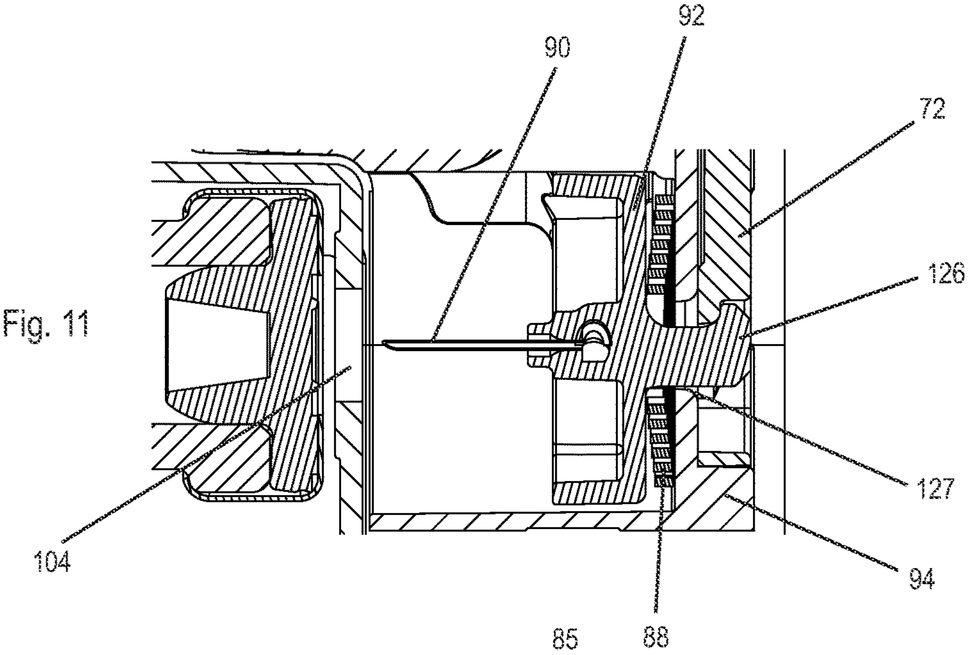
Fig. 12
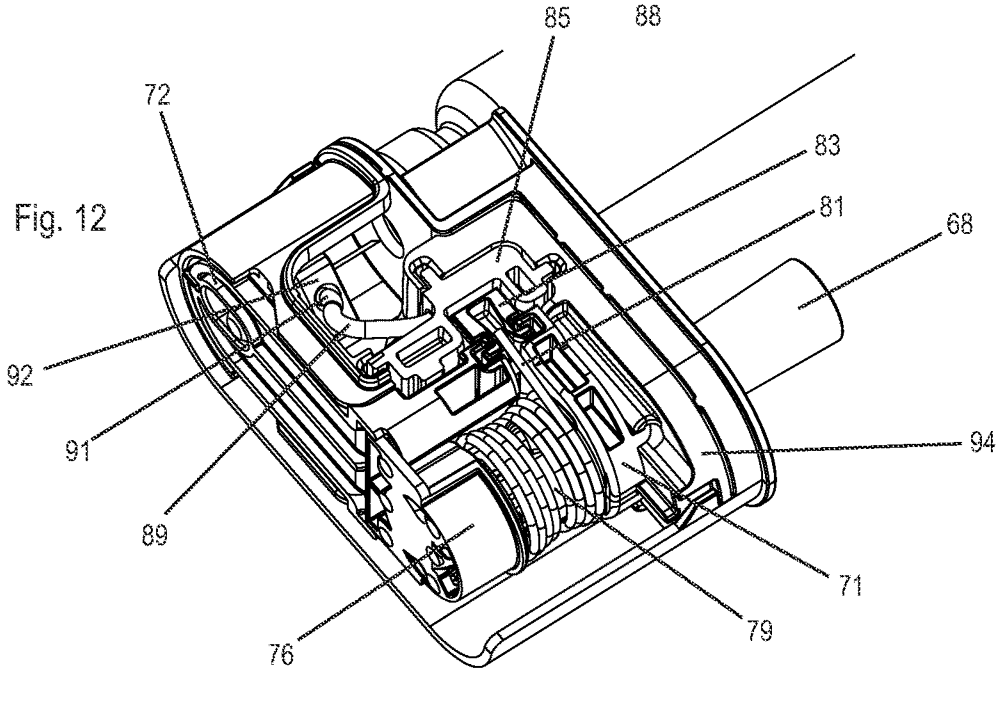

Fig. 13
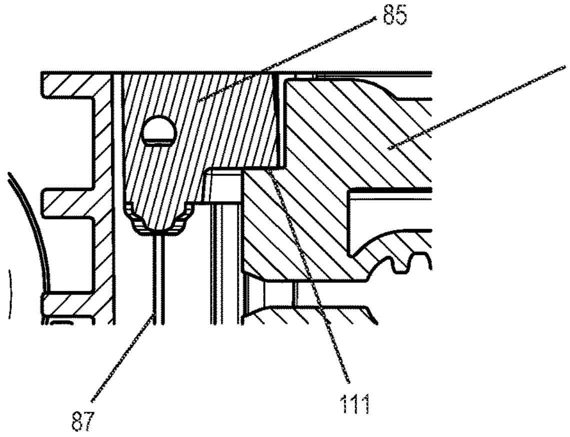
Fig. 14
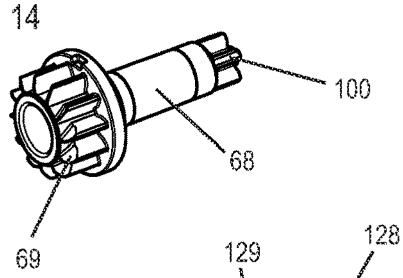
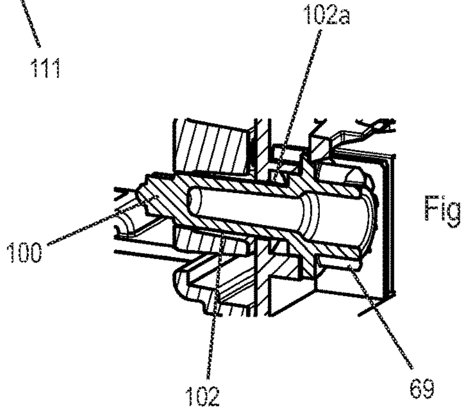
Fig. 15
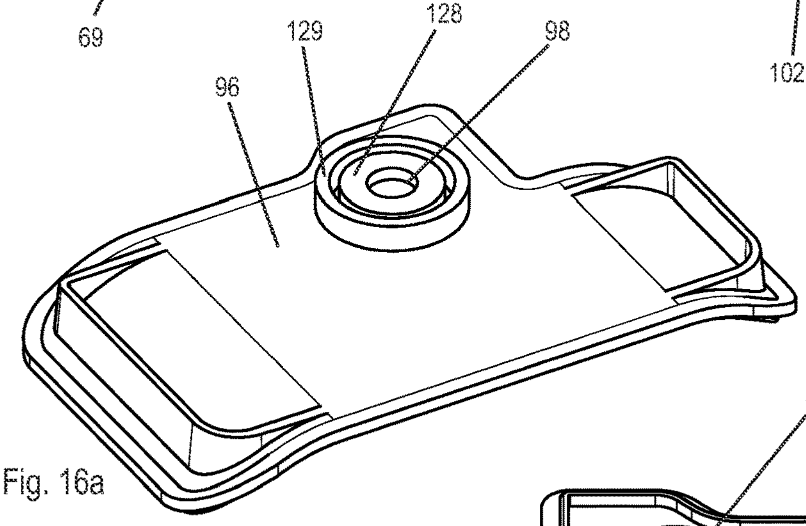
Fig. 16a
Fig. 16b
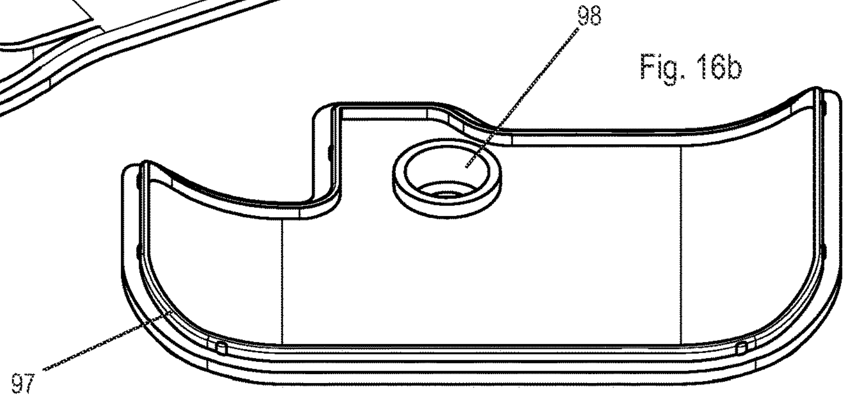
Fig. 17
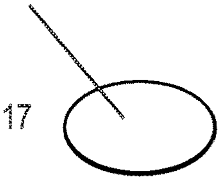
Fig. 18
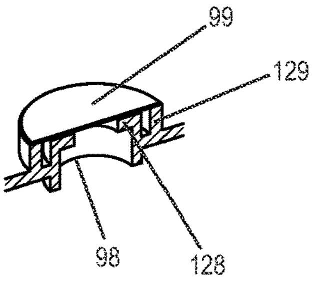

NEEDLE INSERTION MECHANISM FOR AN INJECTION OR INFUSION DEVICE

CROSS REFERENCE TO RELATED APPLICATIONS

This application is a continuation of International Patent Application No. PCT/EP2022/071926, filed Aug. 4, 2022, which claims priority to European Patent Application No. 21199024.7, filed Sep. 27, 2021, each of which is incorporated by reference herein, in the entirety and for all purposes.

TECHNICAL FIELD

The current disclosure relates to a needle insertion mechanism for an injection or an infusion device.

BACKGROUND

Injection and infusion devices are used for the subcutaneous delivery of liquid medicaments to a patient. Infusion devices typically deliver the medication from a cartridge using a drive mechanism and a control mechanism that controls the advancement of a piston rod that abuts a moveable plunger present in the cartridge containing the medication. The medication is delivered to the patient via an opening in the cartridge to a fluid path and an external infusion set comprising a needle for subcutaneous delivery. With such infusion devices both continuous and temporary medicament delivery rates can be programmed.

The injection and infusion devices may comprise a dose setting mechanism, a delivery mechanism, a needle insertion and/or retraction mechanism or a needle shield protection system which is connected or connectable to a drive mechanism. The drive mechanism is driven by a power source which supplies energy to the injection or infusion device for executing tasks such as medication delivery, establishing a connection between the fluid path and the cartridge, skin needle insertion, skin needle retraction, cartridge needle insertion, advancing and/or retracting a piston rod, signaling to the user that the medication is in progress and/or complete, signaling to the user that the device can be removed, powering a processing unit in the device or establishing a wireless connection for data transmission to an external such as a smart phone. The power source used in such injection or infusion devices can be selected from a wide variety of options such as, but not limiting to, a spring (compression, torsional spring, and leaf spring), an electromotor, a battery, pressurized gas or liquid-hydraulic systems and the like. In the injection and infusion devices, several operations need to be arranged in a certain sequence for a correct operation and transmission of power from the energy source to final medicament delivery, for example, by advancing the plunger in the cartridge. The energy consumption by the several steps required to complete an injection needs to be managed well.

A patch device is an example of an infusion device that is attachable to the skin of the patient. Such patch devices do not need an external infusion set for delivery as the fluid path and skin insertion needle are contained in the patch device and may be inserted into the patient therefrom.

For a patch injection device, the skin needle can be inserted first, either using a steel needle (also called cannula) or a combination of a steel needle with a soft cannula; subsequently the steel needle must be retracted to leave the soft cannula in the subcutaneous tissue of the patient, followed by delivery of medication. Typically, the needle, either a soft needle or a steel needle is retracted into the device before the patch device can be removed from the body. Alternatively, the needle is not retracted but a needle shield is extended from the body of the device to protect the needle tip and prevent needle stitching by the patient.

A wearable bolus injector (WBI) is an example of a patch injection device and a bolus of medication, preferably between 1 and 10 mL, is delivered to the patient within a time period between 30 seconds and 30 minutes. Typically, the bolus is injected at a constant delivery rate.

The patch injection device may comprise a prefilled reservoir (a prefilled device, for example a pre-filled WBI) or the reservoir holder in the device is empty and the user inserts a filled cartridge into the reservoir holder prior to use. Alternatively, an empty cartridge is present in the device and the cartridge is filled from the outside just prior use by the user. A prefilled WBI has the advantage that there are no steps required by the user (patient or health care professional).

Examples of the reservoir are a flexible reservoir or a cartridge having a barrel closed by a moveable plunger enclosing a volume available for a liquid or solid medicament and the barrel ends in an opening that is closed by a sealing assembly. An example of the scaling assembly is a septum closing a narrowed neck portion of the cartridge and the septum is attached to the cartridge using a crimp. There may be a permanent fluid connection between the medicament enclosed in the reservoir and a fluid path ending in a skin needle or, alternatively, the fluid connection is established using a reservoir or cartridge needle insertion mechanism. In the latter case the cartridge needle does not penetrate the septum until shortly before use. The cartridge closed by a septum may, for example, be pierced by a cartridge needle just prior to use to establish a fluid connection between the content in the reservoir, via the cartridge needle that is connected to the fluid path ending in the skin insertion needle. The fluid path may comprise a flexible tubing connecting the skin needle to the cartridge needle. The advantage of a non-permanent connection between the fluid path and the cartridge is that there is less risk of contamination during shelf life (for example for a prefilled WBI), and that the cartridge handling during fill-finish is less demanding and better accepted by the pharmaceutical industry as non-standard fluid paths connected to the cartridges do not need to be brought into a sterile fill-finish environment.

An example of a wearable bolus injector is disclosed in EP3603700 A1. A needle or hollow spike can be moved from a non-inserted position to a position piercing the septum of a cartridge. The needle is driven by a spring biasing the needle towards the inserted position and the needle is part of a needle holder which keeps the needle in the non-inserted position as the needle holder engages a control element which may be a sliding element or slider. The control element is moved by an electric drive from a first position keeping the needle holder in the non-inserted position to a second position for releasing the needle holder which is subsequently moved by the spring to the inserted position. In the non-inserted position, the spring also biases the control element towards the housing and the frictional forces between the control element and the housing and the frictional forces between the needle holder engaging the control element need to be overcome for moving the control element towards the second position. As a consequence, the electric drive must also overcome these initial frictional forces. Additionally, the electric drive transfers the rotational movement of a cam shaft to a sliding movement of the control element. The cam shaft is engaged with the housing via a sealing, an O-ring, and the press fit of the O-ring leads to additional frictional losses that need to be compensated for by the electric drive. Both drawbacks may lead to excessive energy consumption and/or overdesigning of the device components such as electric motor, gearing mechanisms or power supply.

It is an object of the present disclosure to overcome the above mentioned drawbacks and reduce the energy consumption using an improved needle insertion mechanism with lower frictional losses.

This objective is solved by the independent claim and specific variants are disclosed in the dependent claims.

SUMMARY

The injection device comprising the needle insertion mechanism of the current disclosure may comprise one or more of the following units:

A housing unit (HU) that the user holds for placing and attaching the injection device to the skin and which encloses the other subassemblies that will be described below. The housing unit may have a starting button accessible to the user for starting the injection and a sensing patch unit (SU) attached to an outside surface. The housing unit may have a viewing window for viewing a part of a cartridge unit (CU) enclosed within the housing that will be described below as well. Furthermore, the housing unit may have selected areas intended for providing visual signaling to the user. The selected areas may be transparent or semi-transparent to view an optical indicator. The housing unit may have an opening for receiving the cartridge unit and the opening may be closed using a cover.

A control unit or Printed Circuit Board Unit (PCB) which controls the device based on signals received from the sensing patch unit, from a Drive Unit (DU) having a power source such as an electromotor or signals received from an external source via a wireless communication such as a Bluetooth connection. The control unit comprises a Printed Circuit Board (PCB) and the electrical power may be supplied by a battery present in the Housing Unit, for example in the Drive Unit. The electronic circuitry of the injection device comprises the battery, the PCB and optionally the sensing patch unit (SU) comprising sensors that will be described below. The PCB may have a push button switch which may be pressed upon by the starting button for starting the injection of the device. The push button switch may be in a disabled (or silent) mode during shelflife and enabled (activated mode) when the sensing patch unit provides a signal that, for example, the device is attached to the skin of the patient. The control unit may provide signals to the user of the device such as audible, tactile or visual status signals (for example using LED or OLEDs) related to the start, progress, end of the injection or when there is a malfunctioning of the device. Examples of the malfunctioning are an occlusion in the medicament delivery system, low battery power, removing the device from the injection site prior to finalizing the injection or failure to insert or retract the needle from the patient's skin. The printed circuit board unit may also send the status signals to an external source such as a smart phone using the bluetooth connection.

The injection device further comprises a drive unit (DU) comprising a drive housing supporting the components of the drive unit. Once the device and the drive unit is activated a piston rod advances from a retracted position to an extended position for delivering a medicament from a cartridge unit (CU) via a needle unit (NU) to the patient. An example of such a power package is a battery powered electromotor that both may be part of the DU. Alternative power packages such as pneumatic, hydraulic or spring driven mechanisms may be used as well that are operated either pure mechanically and/or are supported by the battery powered electromotor. The housing of the of the drive unit supports and guides the piston rod either for a pure linear advancement, or the piston rod may be segmented and guided to perform a U-turn in order to reduce the dimensions (length) of the device. A gearing mechanism is part of the drive unit and the gearing mechanism transforms a rotation of the electromotor into piston rod advancement. The piston rod may rotate around its axis or slide during advancement. For rotational advancement, the piston rod is threadedly engaged with the housing of the drive unit, for non-rotational advancement the piston rod is splined to the housing of the drive unit. For example, the gear mechanism may rotate a threaded rod which is threadedly engaged with a piston rod that is splined to the housing such that the piston rod advances without rotation as the threaded rod is rotated. The gear mechanism may comprise a plurality of gear wheels including worm wheels and the gear mechanism may engage a gear wheel that is part of a cam shaft (CT) driving the needle insertion and retraction mechanism in the needle unit (NU). The needle unit (NU) will be described in detail hereafter. The control unit may control the rotation, the rotational speed and the rotational direction and therewith control and switch between the different operational states of the device, e.g. at rest, needle insertion into the patients skin, establishing a fluid communication between the cartridge unit and the needle unit, delivery of the medicament and retracting the skin needle into the needle unit upon completion of the injection. The rotation of the electromotor is typically switched from non-rotating when the device is sleeping during shelflife, into rotation in a first rotation direction for activating the needle insertion mechanism of the needle unit comprising the skin needle and/or cartridge needle to establish the fluid connection between the patient and the cartridge unit. Subsequently the rotation direction is reversed in the second direction to advance the piston rod and expel medicament from the cartridge unit and the rotation direction may switch back to the first direction for retracting the skin needle from the patient. The rotation is transmitted from the electromotor to the drive unit (piston rod) and the needle insertion mechanism (needle unit) via the gearing mechanism to gear up or gear down the rotational speed of the electromotor. The electromotor thus may generate different rotational speeds for each rotation direction and for each operation status. The mechanism for advancing the piston rod, for example via the threaded rod described above, may be permanently coupled to the gearing mechanism or there may be a coupling mechanism between the gearing mechanism and the threaded rod such that piston rod advancement mechanism can be decoupled from the operation of the needle unit. The needle unit may be permanently coupled to the gearing mechanism or a second coupling mechanism may couple or decouple the rotation from the gear mechanism to the needle unit. The coupling mechanism may be a one-way coupling mechanism such that rotation in one rotation direction is transmitted either to the needle unit or to the threaded rod of the piston rod drive mechanism. The one-way coupling may be an axial or radial one-way ratchet system.

The drive unit housing may provide structural support to other components of the injection device and may hold the PCB unit, the needle unit or the cartridge unit. The drive unit housing may support and provide guidance to contacting elements that enable the transfer of signals from a sensor layer that is part of the sensing patch unit to the PCB unit. The drive unit is configured to be connected to the housing unit.

A sensing patch unit (SU) is attached to the outside surface of the housing unit and comprises a multilayered system having at least one adhesive layer for attachment to the housing, one skin adhesive layer for attachment to the skin of the patient, at least one release liner layer covering the skin adhesive layer, one sensor layer comprising sensors, for example capacitive sensors, one layer having contacts for contacting the sensors in the sensor layer to the control circuit located at the printed circuit board. The sensors in the sensing patch may be capacitive sensors and the capacity of the sensors depends on the presence or absence of the release liner and whether the sensors are in close contact with the human skin. The release liner may have electrically conductive areas at least partially shielding the capacitive sensors in the sensor layer in the sensing patch unit. The removal of the release liner may be detected by the sensors as the dielectric and the capacitance is changed due to the removal of the release liner. Once the device is attached to the skin, the capacitance may change once again or reach a certain level which is measured by the sensors in the sensor layer and signaled to the PCB. The capacitive sensors are powered by the battery present in the drive unit via the contacting elements that may be guided through the drive unit. The sensor layer may have a plurality of sensors embedded therein or printed thereon. The capacitance is measured and transmitted to the control unit of the PCB and the data are used to, for example, activate the push button switch or even automatically start the injection procedure. The sensors in the sensor layer may be formed as electrically conductive areas in the sensor layer for example by printing or by galvanic or chemical deposition of metals (such as silver, gold, aluminum, copper or metal alloys) onto a base sheet forming the sensor layer. Alternatively an electrically conductive carbon layer is used as the sensor and the carbon is printed onto the base sheet or formed by local carbonization of the base sheet. Laser light that locally carbonizes a polymeric sheet of base material such as polycarbonate or polyethyleneterephthalate may be used for that purpose. The sensing patch unit SU may not have a sensor layer but the sensors may be embedded in the housing of the injection device. For example electrically conductive sensor areas may be injection molded directly onto or into the housing using two-component injection molding techniques where one component is non-conductive whereas the other component is electrically conductive. The other component may, for example be a carbon black filled plastic or a plastic filled with metal particles and the carbon black or the metal particles form a percolating network. Alternatively, the housing is treated with laser light to locally carbonize the surface and form the sensor areas. As another alternative, the surface may be flamed to form the conductive layer.

The multilayered system forming the sensing patch unit SU provides at least one passage for the skin insertion needle or for the films that are connected to the needle unit and/or cartridge unit within the housing. The films are guided via the passage in the housing and the passage in the sensing patch unit to the outside surface of the release liner.

The injection device further comprises the needle unit NU enclosed by a needle housing. comprising a compartment enclosing a fluid path that can be sterilized. The needle housing may further comprise a receiving section for receiving the cartridge unit and an opening for receiving a needle insertion and/or retraction mechanism. The opening is closed by a needle cover closing the needle housing. The needle insertion and/or retraction mechanism enables the movement of the skin needle from a retracted position inside the needle unit through a passage in the needle housing to the outside of the needle unit for skin insertion. The needle retraction mechanism moves the skin needle back into the needle unit after delivery of the medicament. The needle retraction mechanism is optional as the skin insertion needle may not be retracted into the device but instead a needle shield may protect the needle after delivery and the shield may move axially and/or rotationally from the inside of the injection device (needle unit) to the outside thereby covering the tip of the skin needle and avoid undesired needle stitching. The needle insertion mechanism may further provide means for inserting the cartridge needle from a position within the needle unit to a second position outside the needle unit thereby penetrating a septum of the cartridge unit. The needle insertion for the cartridge needle and skin needle may occur almost simultaneously and the connecting tubing (conduit) ensures that the medicament can flow to the patient. The cartridge needle and the skin needle may be oriented perpendicular to another. The cartridge needle and the skin needle may be hollow steel needles that are each engaged with a carrier or so-called needle holder. Alternatively, hollow plastic needles are used which may be rigid or flexible. In the latter case, the flexible needle is inserted together with a rigid needle into the skin of the patient and the rigid needle is subsequently retracted. The needles may have the opening at the tip and/or may have separate opening on the side (pencil tip configuration). The carriers (or needle holders) may be slideably engaged within the fluid path compartment and driven by at least one resilient member from a first to a second position thereby inserting the cartridge needle into the cartridge unit and the skin needle into the patient's skin. As a resilient member springs may be used such as compression springs, torsional springs, leg springs or belleville springs. Alternatively elastic elements, compressed gas or pyrogenic means may be used to insert the needles. The resilient member may directly engage with the carriers for the skin needle or the cartridge needle or the resilient element may engage an intermediate member that engages the carrier, having the advantage that tolerances may be compensated that arise when the carriers move towards the inserted position. Controlling the release of the resilient member for needle movement is done using a needle control element or so-called slider. Optionally, the needle control element comprises two parts, namely a slider and an intermediate member. The intermediate member may be positioned between the slider and a needle holder.

The slider is part of the needle unit and moves from a first position to at least one intermediate position into an end position. In the initial position, the slider blocks the movement of the needle carriers that are biased to move towards their inserted positions. In an intermediate position, the needle holder holding the cartridge needle or the skin needle may be released and the cartridge needle and/or the skin needle move to the inserted position. In the end position of the slider, the skin needle is retracted into the fluid path compartment or the needle shield is released to cover the non-retracted skin needle. The slider may be slideably engaged with the needle housing and may move parallel to the bottom of the injection device from the starting to the end position or the slider may rotate through the several positions. The control slider is driven by a cam shaft (CT) that is part of the needle unit and may be engaged with the gearing mechanism of the drive unit. The cam shaft is therefore rotated by the electromotor via the gearing mechanism. The rotation of the cam shaft may be converted into a linear movement of the slider using a gear rack. The fluid path compartment of the needle housing may have an opening that facilitates the assembly of needle insertion and retraction mechanism and the opening is closed by a needle cover (NC) that is glued, welded (for example laser welded or ultrasonic welded) onto the housing to close the opening after assembly. The fluid path compartment has passages that allows the cam shaft to engage with the drive unit, or allows the cartridge needle to pierce the septum of the cartridge unit, or allows the skin needle to be inserted into the skin of the patient. For a safe operation of the device and to prevent contamination of the medicament, it may be required to sterilize the fluid path compartment and therefore the needle cover must form a sterile barrier for the opening in the fluid path compartment. Additionally, the passages for the cam shaft and the needles (skin/cartridge) need to form a sterile barrier or are covered by a sterile barrier. The cam shaft may be engaged with the needle housing using an air tight seal such as an O-ring (alternative solutions like a V-ring or X-ring are presented below) thus allowing for rotation of the cam shaft while preventing contamination of the fluid path compartment. The passages for the skin/cartridge needle may be covered by a sterile barrier film that may be removed prior to the needle movements as the needles may punch out a part of the film leading to needle blockage. The fluid path compartment may be sterilized via the passages as the films covering the passages are porous and enable chemical gas sterilization. Alternatively, the films are non-porous and radiation sterilization is used for sterilizing the fluid path compartment or, alternatively, a separate window is part of the needle housing which is covered by a porous film for chemical sterilization.

The injection device comprises a cartridge unit (CU) which may be inserted just prior to injection, or the injection device is ready to use and already contains the cartridge unit. The cartridge unit comprises a hollow barrel having two open ends. The barrel may be made from glass and optionally made from a plastic such as polypropylene. At the distal end, the barrel narrows into a neck section which is configured for attaching a pierceable septum to the barrel. The septum is attached to the neck using a crimp cap. Opposite to the septum, the barrel is closed by a plunger thereby enclosing the liquid medicament in a fluid tight manner. Advancement of the plunger by the piston rod of the drive unit expels the medicament from the cartridge once a fluid path connection has been established by piercing the septum with the cartridge needle. A cartridge adapter may be positioned between the plunger and the piston rod to compensate for an axial gap between the plunger and the distal end of the piston rod. The cartridge unit is receivable in a cartridge holder which is part of the needle housing or the housing unit. Once the cartridge is received in the cartridge holder, the septum is aligned with the cartridge needle. The barrel of the cartridge unit may be oriented parallel to the bottom surface of the housing unit intended for attachment to the patients skin. The surface of the septum that is not contacting the medicament is sterile and protected from contamination during shelflife. A sterile barrier film may therefore cover the surface of the septum during shelflife. The septum's surface is sterilized using chemical sterilization, steam sterilization or heat sterilization. A porous film may be used as sterile barrier film in combination with gas sterilization such as ETO sterilization or using hydrogen peroxide plasma sterilization. The sterile barrier film may be attached to the crimp of the cartridge unit and the sterile barrier film may be protected by a protective cap that may be removed prior to inserting the cartridge unit into the device. The sterile barrier film may be removed before the cartridge needle pierces the septum i.e. just before use.

The specific details for the needle insertion mechanism, the sealing of the cam shaft, closing the needle unit with the needle cover, a system for removal of the sterile barrier films and finally the arrangement of the visual indicators within the housing are presented below.

In a first aspect which is part of the present disclosure, a needle insertion mechanism for an injection device is presented comprising a needle holder for holding a needle, and the needle holder is adapted to be moved or advanced from a needle retracted position to a needle inserted position, for example under or by means of a needle insertion bias. Furthermore the mechanism comprises a slider (also called control element) which is moveable or adapted to be controlled to be moved from a first position for keeping the needle holder in the needle retracted position towards a second position allowing movement of the needle holder to the inserted position. Additionally, an intermediate member may operatively be positioned between the needle holder and the slider, the intermediate member being moveable from a blocked position, thereby securing or keeping the needle holder in the needle retracted position, to a release position releasing the needle holder for movement along the needle axis into the needle inserted position. A biased gearing or intermediate member bias may be positioned between the intermediate member and the needle holder which biases the intermediate member towards the release position. Alternatively a biasing member or magnets may be positioned between the intermediate member and the needle holder. The needle insertion bias may be converted or redirected into the biased gearing or the intermediate member bias. A lock is located between the intermediate member and the slider locking the intermediate member in the blocked position against the bias of the biased gearing, or against the biasing member or against the bias of opposed paired magnets or against the intermediate member bias. Movement of the slider towards the second position will unlock the lock and the biased gearing (or biasing member of magnets) will move the intermediate member into the release position thereby releasing the needle holder.

The biased gearing biases the intermediate member towards the needle release position, In the prior art the slider had to overcome the frictional resistances between the housing (mechanism holder) and the slider as the biasing force acted directly on the slider. The biased gearing of the current disclosure utilizes the passive forces generated by the biased gearing for movement of the intermediate member such that only a small force is required for movement of the slider for opening the lock as the slider is not directly subjected to the biasing forces. The advantage is that less energy is consumed for moving the slider as only the forces for unlocking the lock need to be overcome and not the frictional forces between the slider and the housing. The electric drive/rack and pinion system can therefore be designed for smaller forces thereby optimizing the energy optimization for the needle insertion mechanism.

The intermediate member may be a intermediate part or a connector or a coupler or may be called a slider release latch.

The needle holder may hold a needle or cannula and may be moved along the needle axis. The needle or cannula may be a hard (steel) needle or a soft (plastic needle) or a combination thereof, for example a hollow (soft) plastic cannula surrounding a steel needle. The needle holder with the needle may move along the needle axis from a position within the housing to a position outside the housing, for penetrating the skin of a patient for subcutaneous. Alternatively, the needle holder is moved along the needle axis within the housing or from one housing part to another housing part towards a reservoir filled with medicament. The reservoir may be a flexible reservoir or a rigid reservoir such as a glass cartridge closed by a septum. The needle may penetrate a septum that is part of the reservoir or cartridge.

Alternatively, the needle insertion mechanism may have both a needle for penetration of the skin and a separate needle for insertion into the reservoir, with a fluid connection between the cartridge/reservoir needle and the skin needle.

A biasing member, for example a spring may be positioned between a housing of the injection device or the needle insertion mechanism and the needle holder for moving the needle holder into the needle inserted position. The needle insertion bias may be provided by the spring. A spring ensures that the cartridge needle holder is moved towards the cartridge or the skin needle holder is moved towards the skin upon release of the intermediate member by unlocking the lock. The cartridge needle can penetrate the septum of the cartridge or reservoir. Therefore relatively high forces (strong springs) are required which lead in the prior art to high frictional forces between the slider and the housing or mechanism holder. Frictional forces are linearly proportional to the normal forces and thus strong springs required for fast insertion lead to high frictional forces for moving the slider before needle insertion. The spring may be a compression spring, torsional spring, a leg spring or a spiral spring. Alternatively, the needle holder is moved by an electric drive, a magnetic drive or a pneumatic drive.

The biased gearing in the needle insertion mechanism comprises at least one gearing surface present on the needle holder and at least one complementary gearing surface present on the intermediate member.

The gearing surface and the complementary gearing surface are part of the gearing and oriented such that the biased gearing biases the intermediate member towards the release position. The gearing surface and complementary gearing surface can be flat or curved or a combination thereof. The gearing surfaces may be inclined with respect to the needle axis, with an angle between the plane of the surface and complementary surface and the needle axis below 80 degrees, preferably below 70 degrees, more preferably below 60 degrees. The biased gearing biases the intermediate member towards the release position, alternatively the intermediate member is moved into the opposite direction or the intermediate member is biased towards a linear or a rotational movement.

Optionally, the gearing surfaces may have two inclination angles, a first angle of, for example, 60 degrees and a second angle having a lower inclination angle for example below 50 degrees.

The gearing surface of the needle holder may be present on a knob extending from the needle holder engaging the complementary gearing surface on a locking fork on the intermediate member. The locking fork may be U-shaped with an opening for the knob. The complementary gearing surface may be located on the legs of the U-shaped opening.

In an embodiment, the spring biases the biased gearing or provides the intermediate member bias and additionally the spring provides the needle insertion bias for moving the needle holder into the needle inserted position. The spring thus serves at least two purposes—moving the needle holder towards the inserted position and biasing the biased gearing for movement of the intermediate member towards the release position.

The lock of the needle insertion mechanism may comprise a locking member on the intermediate member engaging a locking surface on the slider and/or a locking surface on the housing when the slider is in the first position. The locking member can also be called a locking part or simply a locker.

The locking member and the locking surfaces on the housing and/or slider are in a form-fit or in a friction fit engagement when the slider is in the first position, thereby keeping the lock in the locked position.

Form fit or friction fit keeps the lock in a locked position thereby keeping the intermediate member in the blocked position. Alternatively the lock is based on magnetic forces, for example using two magnets. The magnets may be passive magnets or electromagnets. The lock thus may be unlocked by switching two electromagnets from a mutual attraction to a mutual repellant force.

The locking member for the needle insertion mechanism may be positioned between and may abut a locking surface present on a protrusion on the slider and may abut a locking surface present on a protrusion on the housing or a housing part such as the mechanism holder.

The locking member for the needle insertion mechanism may have at least one flexible arm present on the intermediate member and the end of the flexible arm may abut the locking surfaces on the slider and/or on the housing.

The end of the flexible arm may have an enlarged head portion being in a form fit or friction fit engagement with one or both of the surfaces on the housing and on the slider when the slider is in the first position. Other engagement such as ratchet systems may be envisaged or the end of the flexible arm may be part of a magnetic lock and comprise a magnet engaging a magnet present on the slider and/or on the housing.

The needle insertion mechanism where the abutment between the locking member and the locking surface on the slider is released when the slider is moved from the first position towards the second position.

The flexible arm may be flexed due to the movement of the intermediate member towards the release position by the biased gearing thereby releasing the abutment between the locking surface on the housing and the locking member and thereby unlocking the lock.

The needle insertion mechanism where the intermediate member and/or the slider is guided by the housing for movement perpendicular to the longitudinal axis. The guidance by the housing may be optimized to reduce friction between the intermediate member and the housing (or housing part such as the mechanism holder) and between the slider and the housing. The optimization may include the use of low friction materials (polymers filled with graphite or silicone oil) and/or polishing of the contact surfaces and/or using lubricants.

The intermediate member and the slider may be moved in opposite directions. The slider and intermediate member may be arranged to move linearly in opposite directions. Alternatively both rotate in two opposite rotation directions.

The needle insertion mechanism may be operated using an electric drive, for example by moving the slider by an electric motor using a rack and pinion system transforming a rotational movement of the cam shaft into a linear movement of the slider.

The needle insertion mechanism may be used in a patch injection device comprising one or more of the following units: the housing unit, the cartridge unit, the needle unit, the drive unit, the sensing patch unit as described in detail above.

In a second aspect which is part of the current disclosure for the reduction of the frictional losses, a sealing element is presented. The sealing element may be configured to provide a sealing between a rotatable shaft, part of the drive unit or needle unit and a housing, part of the housing unit or the needle unit or the drive unit. The rotatable shaft may be the cam shaft mentioned above. The sealing comprises a first sealing surface configured for engaging the housing and a second sealing surface configured for engaging the rotatable shaft. The first and second sealing surfaces may be connected by a living hinge and made from an elastomeric material.

The sealing element may be compressed between the rotatable cam shaft and the housing and may have a circular shape surrounding the rotatable shaft that is contacted by the second sealing surface. Furthermore a cross-section of the sealing element may be V-shaped and where the living hinge is located at the bottom of the V-shaped cross-section.

The sealing element is part of a patch injection device and may be located between the drive unit and the needle insertion unit of the patch injection device and provides a liquid tight sealing and/or a sterility barrier.

In a third aspect, which is not part of the present disclosure, a detail of the needle unit presented above is disclosed. The needle unit may be for a patch injection device and comprises a needle housing with a bottom surface surrounded by a wall forming an opening. The opening may be closed by a needle housing cover, for example by a welding seam and where the welding seam is oriented parallel to the bottom surface. Optionally, the needle housing may comprise at least one passage that is covered by a sterile barrier that may be removed from the at least one passage.

The needle housing may house the needle unit described above, whereby the needle unit may be configured to move an insertion needle from a position within the needle housing towards a position at least partially extending from the bottom of the needle housing through the passage. Optionally, the needle unit can retract the needle back into the housing from the extended position.

As an alternative, the needle unit may be configured to move a second insertion needle from a position within the housing to a position outside the needle unit but still within the housing. The second insertion needle may be moved into a reservoir located inside the injection device.

The welding seam may be made by laser welding or ultrasonic welding. The laser light used for laser welding is oriented perpendicular to the bottom surface and the focal point of the laser light is located close to or within the seam.

A method for closing a needle unit of a patch injection device is presented comprising at least the following steps:

- providing a needle housing with a bottom surface and an opening surrounded by sidewalls;
- providing a needle unit configured to move at least one needle from a position inside the needle housing to a position at least partially extending outside the needle housing;
- providing a needle housing cover for closing the opening;
- inserting the needle unit into the needle housing;
- covering the opening with the needle housing cover;
- applying laser light to the surface of the needle housing cover for welding the needle housing cover to the needle housing;

where the laser beam is oriented perpendicular to the bottom surface to form a welding seam essentially parallel to the bottom surface.

In a fourth aspect which is not part of the current disclosure a detail of the housing unit presented above is disclosed. The injection or infusion device comprises a housing or housing part forming a wall between the inside and outside of the injection or infusion device. An electronic control system having a plurality of visual indicators is located inside and adjacent to the housing and each of the plurality of visual indicators is separated from the other of the plurality of visual indicators by at least one partition wall. The electronic control system may be part of the PCB unit.

The housing is at least partially translucent and the at least one partition wall is less translucent than the wall of the housing part located between the inside and outside. The visual indicator may be a LED light or OLED light. The at least one partition wall may be oriented perpendicular to the wall of the housing that is translucent. The at least one partition may be separate from the housing and may be made from a different material then the housing, or the at least one partition wall may be integrally formed with the housing. In the latter case the at least one partition wall is made by injection molding of a plastic and the housing and partition wall are integrally formed. The wall thickness of the translucent part of the housing may be below the wall thickness of the at least one partition wall.

In a fifth aspect which is not part of the current disclosure, a system is presented for removing or releasing a film from an injection or an infusion device, for example a patch injection or patch infusion device for skin attachment using an adhesive patch. The system comprises a release liner covering the skin adhesive of the adhesive patch and at least one sterile barrier film or film assembly at least partially covering a surface or passage inside the housing unit (HU). One end section of the sterile barrier film or film assembly is attached to the cartridge unit (CU) or needle unit (NU) with a first adhesive strength F1 and the other end section of the sterile barrier film or film assembly is attached to the release liner with a third adhesive strength F3. The adhesive strength F3 is above adhesive strength F1. The adhesive strength may be expressed in Newtons (N).

The film assembly may comprise a pull tab connecting the at least one sterile barrier film to the release liner where the pull tab is attached to the release liner with the third adhesive strength F3 and attached to the at least one sterile barrier with adhesive strength F2. The adhesive strength F3 is above or equal to F2 and F2 is above F1: F3≥F2>F1.

The one end section of the sterile barrier film is attached to a housing part surrounding the passage of the needle unit covered by the sterile barrier film. Alternatively the one end section of the sterile barrier film covers a pierceable septum of the cartridge unit, the one end section may, for example, be attached to the crimp of the cartridge unit with adhesive strength F1.

The one end section of the sterile barrier film may cover a passage for a cartridge needle of the needle unit and/or the one end section may a passage for a skin needle of the needle unit.

The system may be configured for simultaneous removal of the at least one film or film assembly together with the release liner.

The system for removing or releasing a film where the adhesive strength F1 is below 9N preferably below 7N, more preferably below 6N.

The system for removing or releasing a film where the adhesive strength F3 is above 7N more preferably above 9N, more preferably above 10N most preferably above 15N.

The system for removing or releasing a film where the adhesive strength F2 is above 7N more preferably above 9N, more preferably above 10N most preferably above 15N The system for removing or releasing a film where the adhesive strengths F1, F2, F3 are based on an adhesive, welding, thermal welding, ultrasonic welding, laser welding connection.

The system for removing or releasing a film where the at least one sterile barrier film is a porous membrane configured for gas (ETO, NOx) or gas plasma (for example hydrogen peroxide) sterilization. The porous membrane may be a non-woven membrane comprising polyethylene fibres such as a Tyvek film.

The above mentioned aspects may be combined with each other.

BRIEF DESCRIPTION OF THE DRAWINGS

While the disclosure has been described in detail in the drawings below and foregoing general description, such description is to be considered illustrative or exemplary and not restrictive. Variations to the disclosed embodiments can be understood and effected by those skilled in the art and practicing the claimed disclosure, from a study of the drawings, the disclosure, and the appended claims.

FIGS. 3*a*, 3*b*, 3*c*: PCB unit,

FIG. 3*d*: PCB unit assembled with drive unit (DU),

FIG. 9: Fluid path, not shown are the skin needle and the cartridge needle,

FIG. 10: Cartridge needle slider spring,

FIG. 11: Detailed view of cartridge needle slider in mechanism holder,

FIG. 12: Needle insertion assembly, cartridge needle and skin needle in retracted position, FIG. 13: Detail of skin needle holder abutting the slider, keeping the holder in the retracted position, FIG. 14: Cam shaft of the needle unit, FIG. 15: Cam shaft in passage of the needle unit, FIGS. 16*a*, 16*b*: Needle cover for needle unit, FIG. 17: Sterile barrier film, FIG. 18: Sterile barrier film covering aperture skin needle in needle cover.

DETAILED DESCRIPTION

Definitions

The term "medicament" or "medication" includes any flowable medical formulation suitable for controlled administration through a means such as, for example, a cannula or a hollow needle and comprises a liquid, a solution, a gel or a fine suspension containing one or more medical active ingredients. A medicament can be a composition comprising a single active ingredient or a pre-mixed or co-formulated composition with more than one active ingredient present in a single container. Medication includes drugs such as peptides (e.g., insulin, insulin-containing drugs, GLP-1 containing drugs or derived or analogous preparations), proteins and hormones, active ingredients derived from—or harvested by—biological sources, active ingredients based on hormones or genes, nutritional formulations, enzymes and other substances in both solid (suspended) or liquid form but also polysaccharides, vaccines, DNA, RNA, oligonucleotides, antibodies or parts of antibodies but also appropriate basic, auxiliary and carrier substances.

The distal end or distal direction is defined by the direction of the needle configured to penetrate the skin of the patient. For an injection pen this may be the injection needle and the end of the pen holding the needle or being configured to hold the needle is the distal end. For an infusion device the distal end and the distal direction is towards the needle configured to penetrate the skin of the patient, which may be along the axis of the device or tilted or perpendicular to the axis of the device. The distal direction in an infusion device represents the direction in which the medicament flows towards the insertion needle. The proximal direction or end is opposite to the distal direction or end.

In the claims, the word "comprising" does not exclude other elements or steps, and the indefinite article "a" or "an" does not exclude a plurality. For example "a spring" does not exclude the fact that there may be two springs that functionally or structurally fulfill the purpose of "a spring". The mere fact that certain elements or steps are recited in distinct claims shall not preclude the existence of further meaningful combinations of these elements or steps.

Figure 1A:
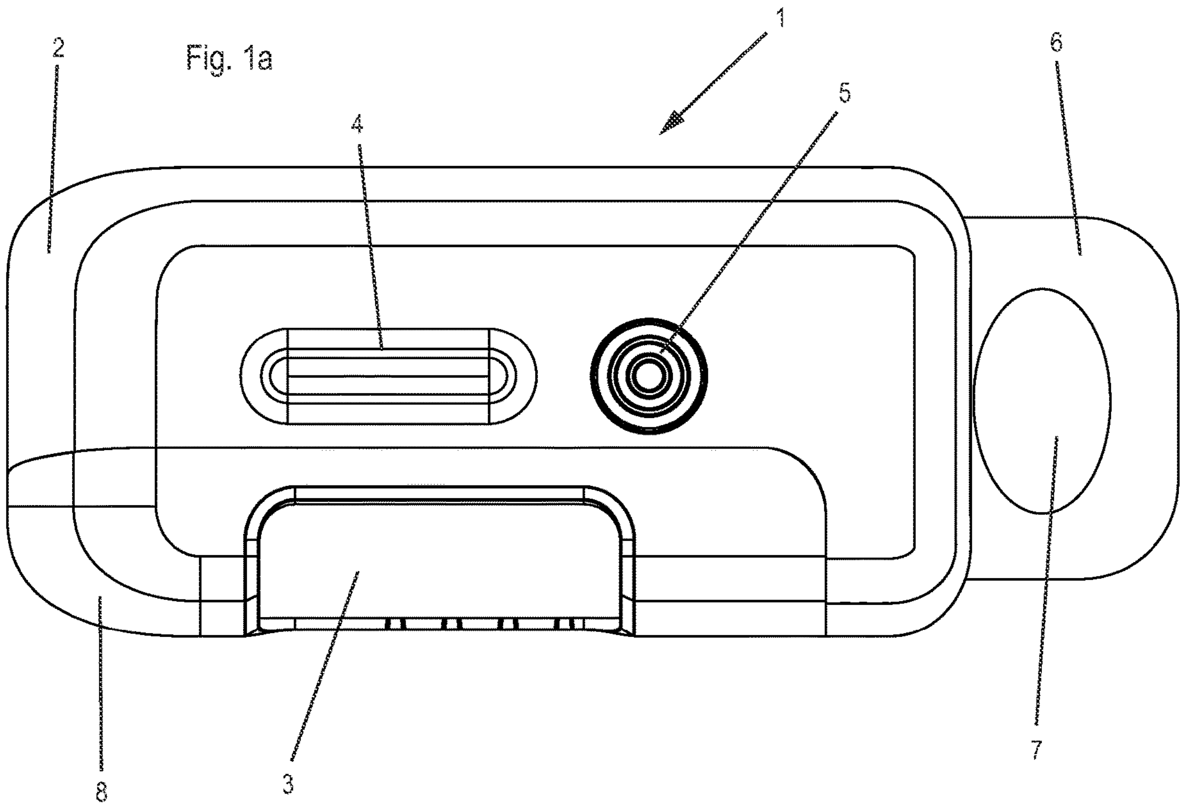
FIGS. 1*a*, 1*b*: Injection device.
Figure 1B:
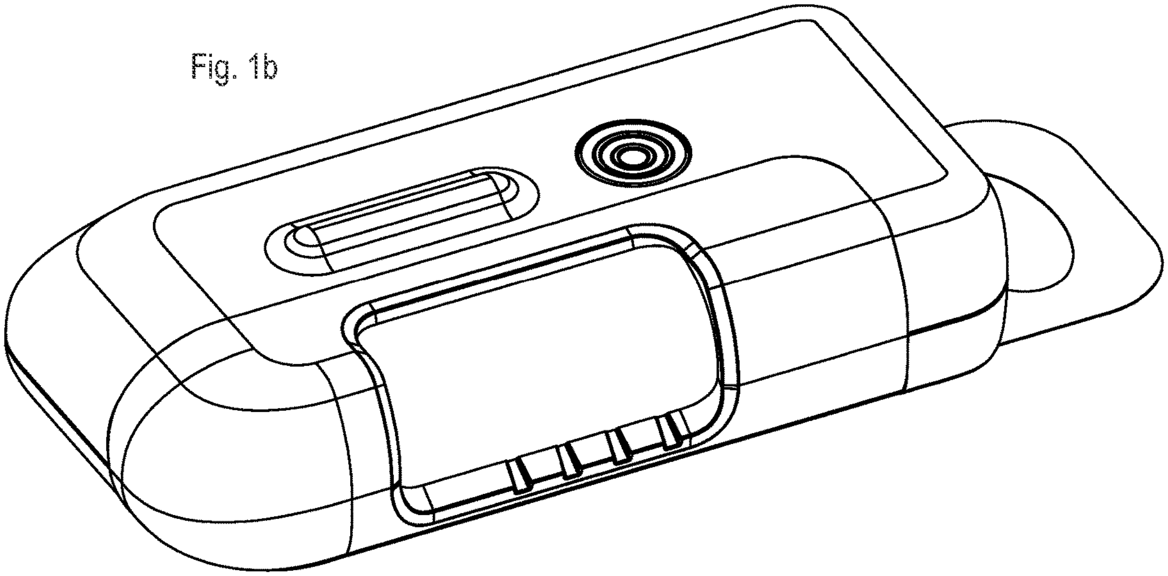
Figure 2:
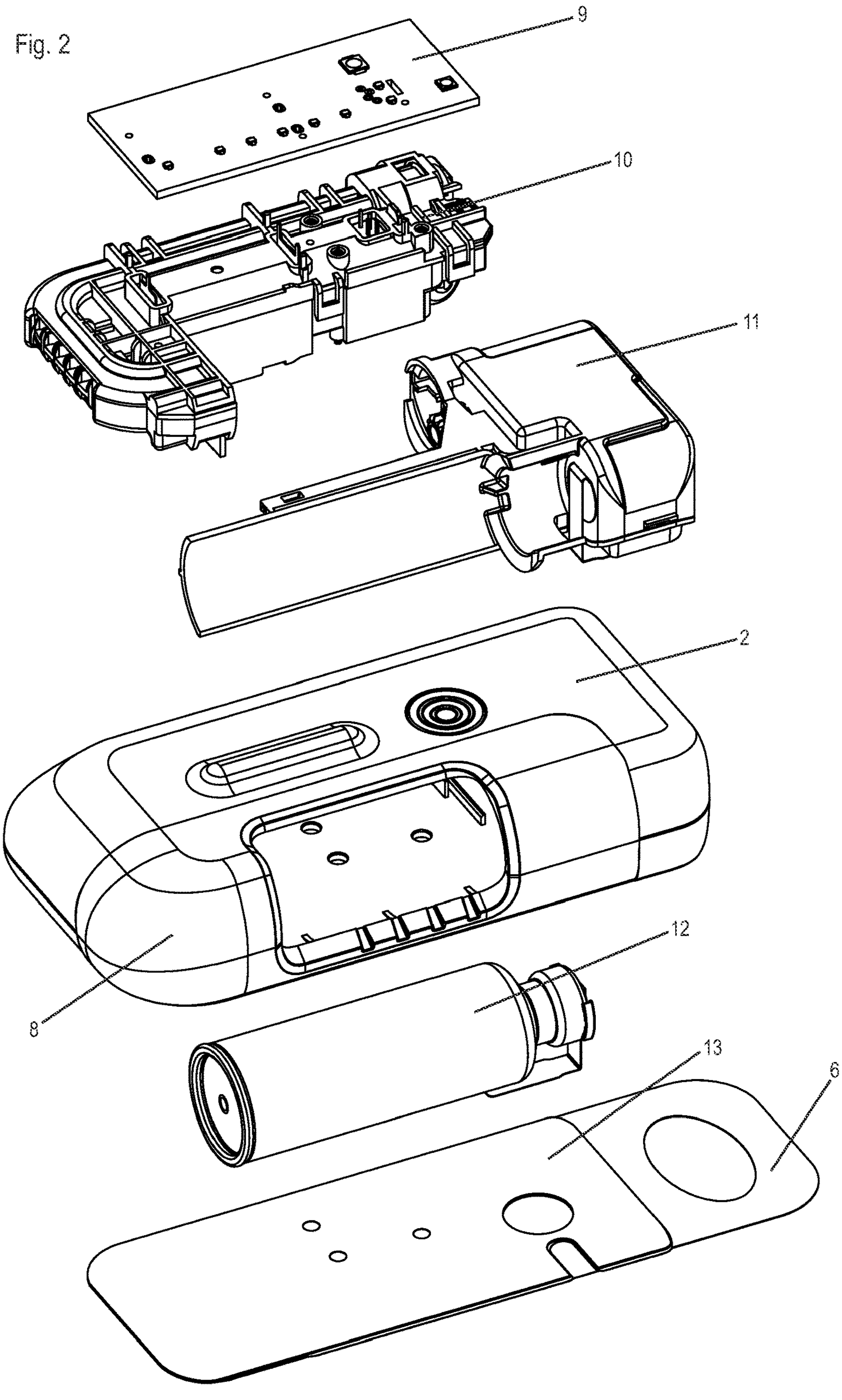
FIG. 2: Injection device showing the subassemblies.

Turning to the Figures, in FIG. 1*a*, the injection device (1) is shown which comprises a housing unit HU (2) having an indicator (4) and a push button (5). The housing unit HU (2) is closed by a cover (8) having a viewing window (3) for viewing a not shown cartridge. The injection device can be attached to the skin of the patient by a skin adhesive layer which is part of a sensing patch unit that is attached to a bottom surface of the housing unit (2). The skin adhesive layer is covered by a release liner (6) which prevents undesired attachment of the injection device such that the patient can first select a suitable location for skin attachment. The release liner is a sheet of material that comprises a gripping area (7) facilitating the removal of the release liner by the user. The gripping area may be roughened or having an elevated area that may be structured. Alternatively, the gripping area may be an aperture in the sheet of material, as shown in FIG. 2. The gripping area may have visual indicators such as arrows or symbols printed thereon to instruct the user. A 3-dimensional perspective view of the injection device is presented in FIG. 1*b*.

An exploded view of the injection device showing the subassemblies and components forming the device is shown in FIG. 2. The injection device comprises a printed circuit board unit PCB (9) for controlling the injection of the device, a drive unit DU (10) for driving a piston rod, a needle insertion mechanism being part of a needle insertion unit NU (11), the housing unit HU (2), a cartridge unit CU (12) and a sensing patch unit SU (13).

The PCB unit (9) is shown in FIGS. 3*a*,3*b*, and 3*c* and comprises a printed circuit board with a selection of electronic components and features such as conductive leads, integrated circuits, contacts for power supply, contacts for receiving signals from the sensing patch unit (13), contacts for sending signals to the electromotor, a switch and a wireless transmitter/receiver unit. The top surface (14) of the PCB unit comprises a push button switch (16), positioning apertures (18), LED light indicators (17) and through holes forming contacts (20) for a stepper motor. The bottom surface (15) comprises contacts (21) for contacting the battery and separate contacts (19) for contacting contact springs. The PCB unit (9) is positioned on top of the drive unit (10) using protrusions (22) of the drive unit that engage the apertures (18) of the PCB unit, see FIG. 3*d*. The PCB unit may be fixated by plastic deformation and/or melting the protrusions (22) after positioning the PCB unit on top of the drive unit (10). Alternatively, the PCB unit (9) is fixated using a snap-fit connection.

Figure 4:
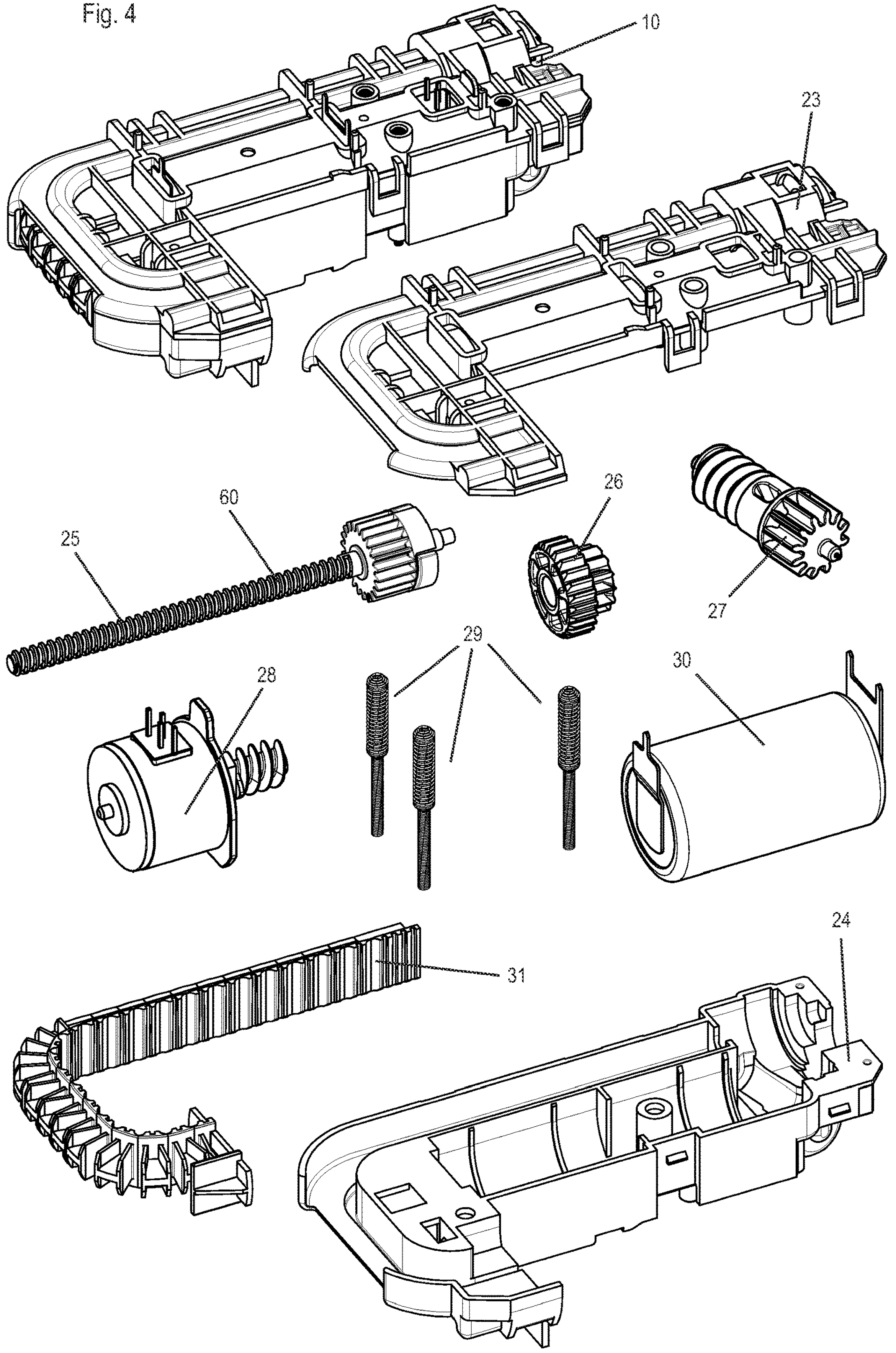
FIG. 4: Exploded view showing all components of drive unit.

An exploded view of the parts forming the drive unit DU (10) is depicted in FIG. 4. A drive cover (23) engages a drive carrier (24) thereby forming the housing for the drive unit. An elongated threaded rod TR (25) is received by bearings in the drive carrier (24). The threaded rod (25) is driven by an electromotor via a gearing mechanism and rotation of the threaded rod (25) is transformed in axial movement of a piston rod. The gearing mechanism comprises a gear shaft (27) and the gear mechanism is driven by a stepper motor (28). The gear shaft (27) is received by bearings in the drive carrier (24) and the stepper motor (28) is received in a preformed compartment of the drive carrier. The stepper motor (28) is powered by a battery (30) which is also enclosed in, and may be attached to the drive carrier (24). For example the battery may be glued or adhesively attached to the drive carrier to prevent battery loosening upon mechanical impact. Alternatively, a press-fit connection is used to fixate the battery using clips or a resilient foam material. A plurality of contact springs (29) are guided through the drive unit (10) establishing contacts between the sensing patch unit and the PCB unit. The contact springs (29) are made from an electrically conductive material and may be spiral springs which may contact the sensing patch unit or the PCB unit directly or via contacting pins that are biased by the spring. The diameter of the contact springs (29) may vary to facilitate the positioning in one of the drive cover (23) or the drive carrier (24). The drive unit has a piston rod (31) which may be guided by the drive carrier (24) to form a U-shaped piston rod that is configured to advance a plunger in a cartridge for expelling the medicament from the device.

Figure 5A:
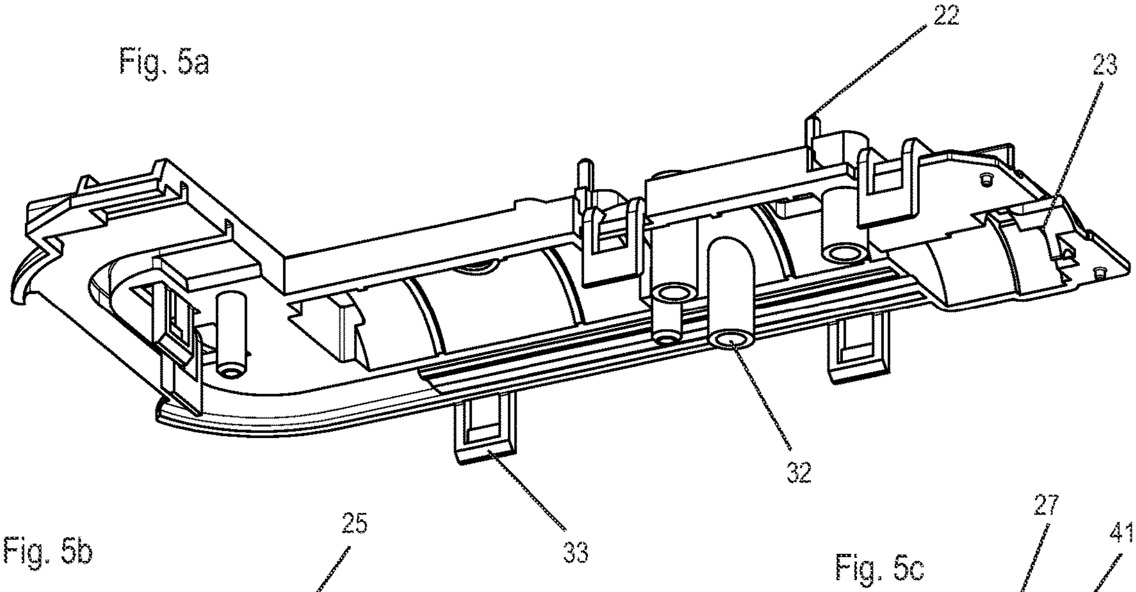
FIG. 5*a*-5*k*: Individual components drive unit.
Figure 5B:
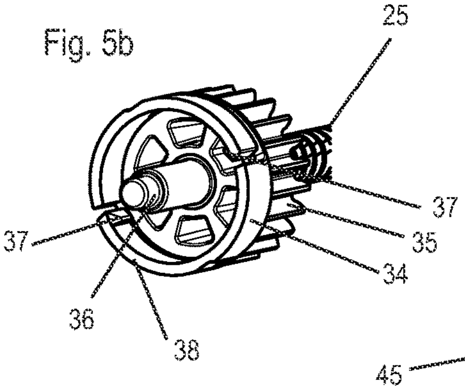
Figure 5C:
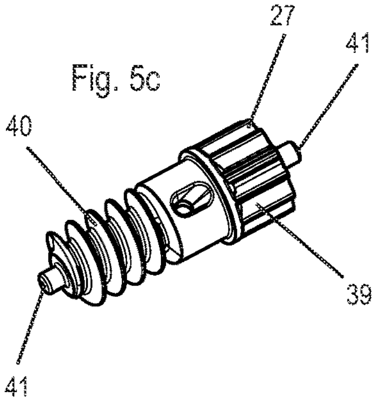
Figure 5D:
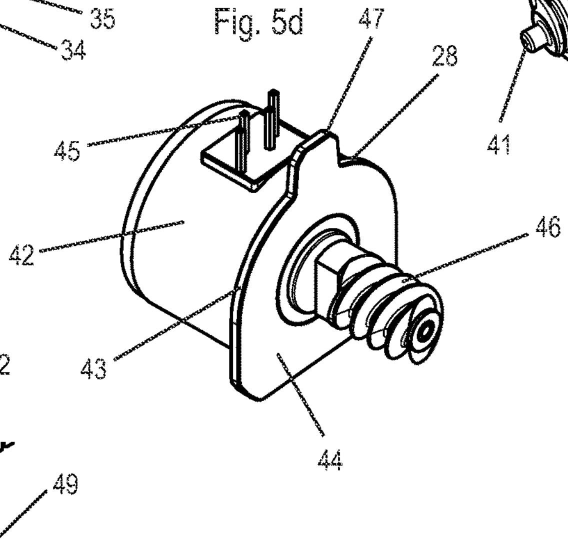

A detailed view of the components forming the drive unit is shown in FIGS. 5*a* to 5*k*. The drive cover DC (23) comprises the protrusions (22) for positioning and fixation of the PCB unit (9) and a snapper (33) or snap fit connector for connecting the drive cover to the drive carrier (24). The drive cover comprises cylindrically shaped apertures (32) that are aligned with complementary apertures of the drive carrier to form a passage for the contacting springs (FIG. 5*a*). In FIG. 5*b*, the threaded rod (25) comprises a threaded rod driver (34), shaped as a gear wheel that is rotationally and axially fixed to the threaded rod (25) and comprises gear teeth (35) on the outside circumferential surface of the driver (34) and which are oriented parallel to the axis of the threaded rod. Adjacent to the gear teeth (35) there is at least one flexible arm (38) having at least one ratchet member (37) pointing towards the central axis of the threaded rod (25). The at least one flexible arm (38) surrounds a hollow space within the driver (34) that is available for the ratchet wheel (26). The threaded rod (25) has a shaft end (36) that is received in a bearing formed in the drive carrier (24). The shaft of the threaded rod (25) may engage a central opening of the ratchet wheel (26). The gear shaft (27) is shown in FIG. 5*c* and comprises a gear wheel (39) that is configured to engage a worm wheel of the stepper motor. Adjacent to the gear wheel (39), the gear shaft comprises a worm wheel (40) that is configured to engage the gear teeth (35) of the threaded rod driver (34). The gear shaft (27) has shaft ends (41) that are received by bearings in the drive carrier (24). A detailed view of the stepper motor (28) is presented in FIG. 5*d*, the stepper motor comprises a motor (42) an end plate (44), contacts (45) and worm wheel (46) of the stepper motor. The end plate (44) has edges (43) to rotationally and axially fixate the stepper motor (28) in the drive carrier. The end plate (44) may have a handle (47) facilitating the gripping and automated positioning of the stepper motor (28) in the drive carrier (24). The worm wheel of the stepper motor (46) engages the gear wheel (39) of the gear shaft and the worm wheel (40) of the gear shaft (27) engages the gear teeth (35) of the driver (34) for the threaded rod. The worm wheel (46), the gear wheel (39), the worm wheel (40) and the gear teeth (35) form a gearing mechanism (46,39,40,35) to gear down the rotation of the motor (42) into a rotation of the threaded rod.

Figure 5E:
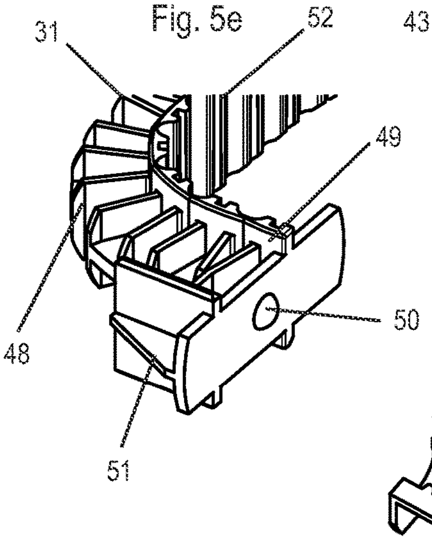
Figure 5F:
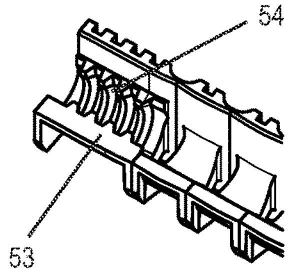
Figure 5G:
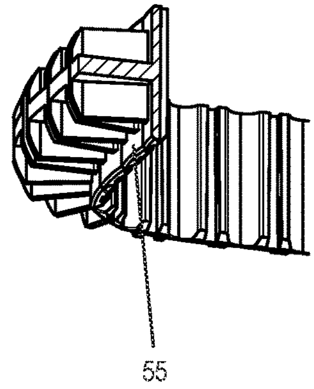

Details of the piston rod (31) are shown in FIGS. 5*e*, 5*f* and 5*g*. The piston rod comprises segments (48) that are connected to each other via hinges (52) such that the individual segments can rotate with respect to each other. The segments (48) have a segment guide (55) that protrudes from each segment in a direction perpendicular to the direction for advancing the piston rod (31). The last segment (49) of the piston rod comprises a protrusion (50) configured for engaging a spacer that is part of the cartridge unit to form a pivot bearing between the spacer and the last segment (49). The last segment may comprise a guiding fin (51) that is configured to engage the barrel of the cartridge such that the last segment, possibly together with the segmented piston rod, correctly enters the cartridge. The first segment (53) of the segmented piston rod may comprise an internal threading (54) that engages an external threading of the threaded rod (25).

Figure 5H:
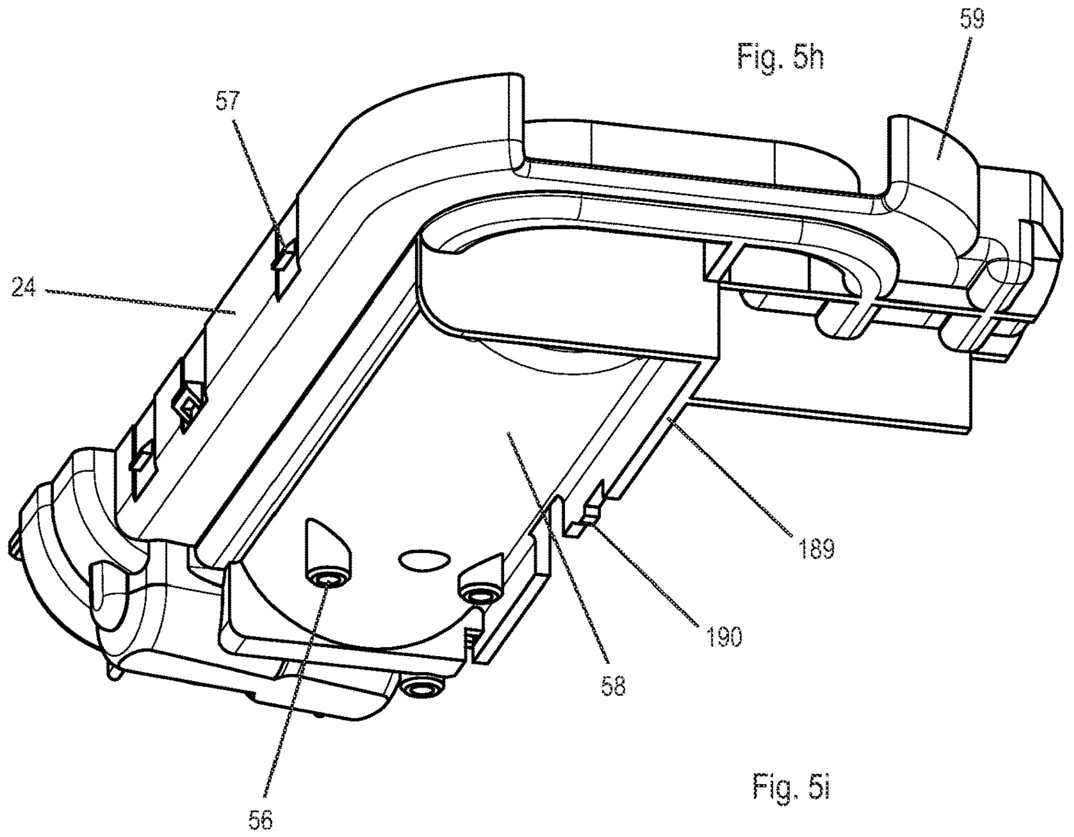
Figure 5I:
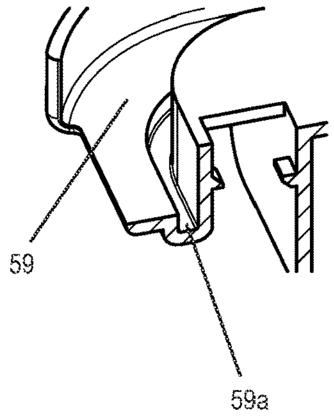
Figure 5J:
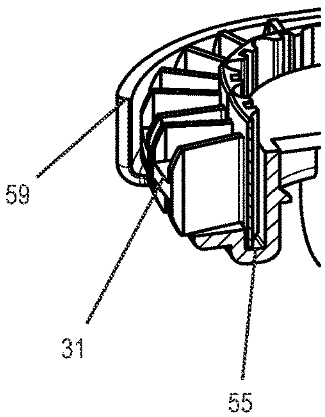

The drive carrier (24) comprises cylindrical apertures (56) that are aligned with the apertures (32) of the drive cover after assembly to guide the contact springs (29) through the drive unit (FIG. 5*h*). The carrier furthermore comprises a holder (58) for the battery (30) and the stepper motor (28), and protrusions or snappers (57) that may connect, for example irreversibly, to the snappers (33) of the drive cover. A guide (59) (FIG. 5*i*) guides the segments of the piston rod such that the piston rod may go from a straight or stacked configuration of the individual segments to a curved configuration and back to a straight configuration, thereby rotating the individual hinges between the segments. The piston rod may have a U-shape due to the guide (59) of the drive carrier. A detail of the segmented piston rod (31) engaging the guide (59) is shown in FIG. 5*j*. The segment guide (55) of each segment (48) engages a slot or keyway (59*a*) of the drive carrier thereby further guiding the piston rod (31) and preventing rotation of the piston rod around its own axis. The threaded engagement of the first segment of the piston rod with the threaded rod is therefore transferred in axial advancement (or retraction) of the piston rod once the threaded rod is rotated via the gear mechanism (46,39,40,35).

Figure 5K:
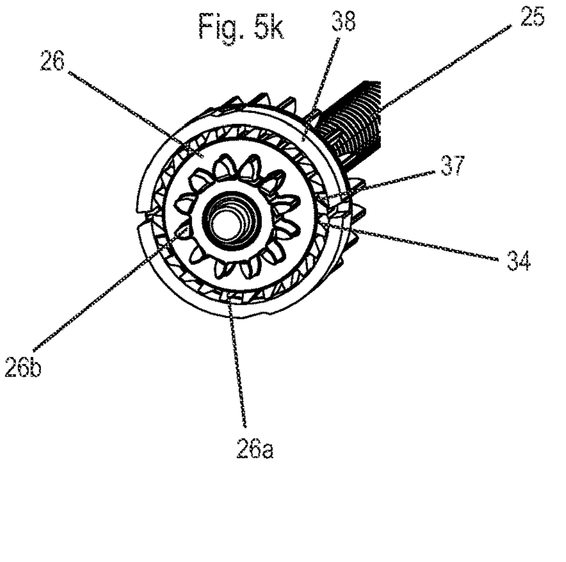

A coupling mechanism between the driver (34) of the threaded rod (25) and the ratchet wheel (26) is shown in FIG. 5*k*. The ratchet wheel (26) is inserted in the hollow space of the driver (34) onto the shaft and ratchet teeth (26*a*) on the outer surface of the ratchet wheel (26) engage the ratchet member (37) of the driver (34). The interaction between the shaft of the threaded rod and the ratchet wheel (26) is such that the ratchet wheel may rotate in both directions with respect to the shaft. However the ratchet teeth (26*a*) are asymmetrically shaped, for example saw tooth shaped that extend radially outwards, and the engagement with the ratchet member (37) mounted on a flexible arm (38) is such that the ratchet wheel may rotate in one direction only due to the one way ratchet (37, 26*a*). Or, as the driver (34) is rotationally fixed to the threaded rod (25), rotation of the driver in one direction is always transmitted to the ratchet wheel due to the form fit between the teeth (37, 26*a*), whereas the ratchet member (37) ratchets over the teeth (26*a*) in the opposite direction thereby generating audible clicks. In the latter case the ratchet wheel may not rotate or only rotates once a certain frictional resistance has been overcome.

Figure 6:
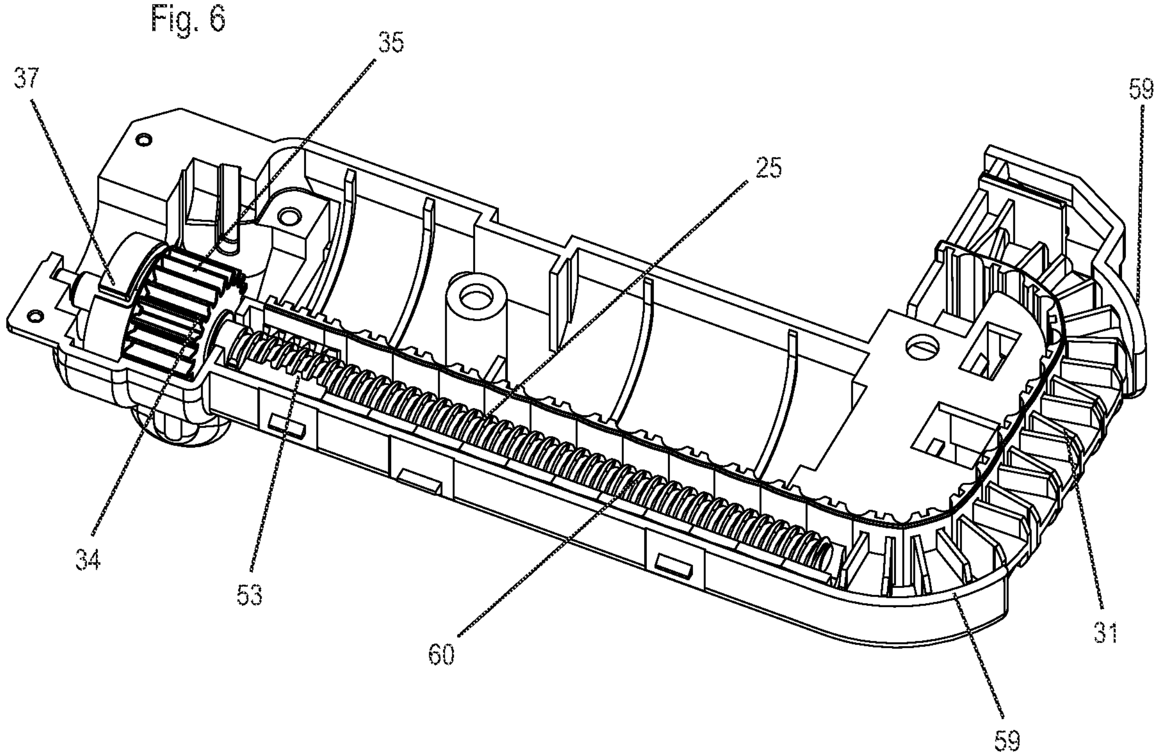
FIG. 6: Threaded rod, piston rod within drive carrier of the drive unit.

The drive carrier supporting the threaded rod (25) engaging the segmented piston rod (31) is shown in FIG. 6. The threaded rod (25) comprises an external threading (60) which engages the internal threading (54) of the first segment. The segmented piston rod is guided by two guides (59) that direct the segmented piston rod in a U-shape. Rotation of the threaded rod driver (34) via the gear mechanism will advance the piston rod, e.g. slide the piston rod, due to the threaded engagement with the first segment.

Figure 7:
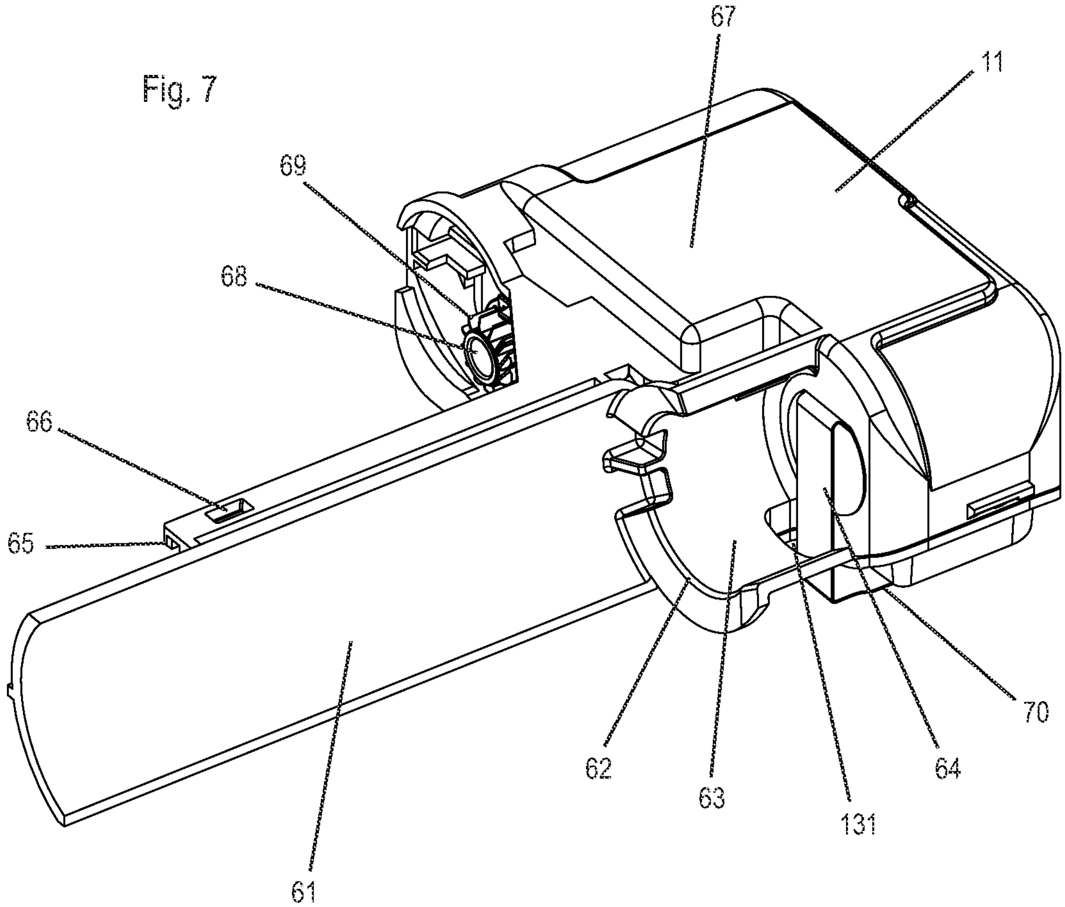
FIG. 7: Needle unit (NU)

The needle unit (11) is shown in FIG. 7 and has a cartridge holder (61) adapted to receive the cartridge unit (12) whereby the neck of the cartridge engages the abutment surface (62) of the cartridge holder to axially position the cartridge unit in the cartridge holder (61). A distal end of the cartridge unit, for example the crimp, is receivable in the receiving section (63) of the cartridge holder. The housing (67) is closed by a sterile barrier film (64) that is attached to the housing and covering a passage for a cartridge needle. The sterile barrier film (64) has a pull tab (70) that is guided through an aperture (13) located between the needle housing and the cartridge holder to an outside surface, for example a surface of the release liner, of the injection device. A rotatable cam shaft (68) having a gear wheel (69) located outside of the needle unit is available for driving the components located inside the needle unit. The cam shaft is mechanically transferring rotation within the drive unit to the needle unit. The passage of the cam-shaft (68) is sealed to form a tight barrier (for example using an O-ring or V-ring) that prevents contamination from outside the needle unit via the cam-shaft surface to the inside of the needle unit. The needle unit (11) is attachable, to the drive unit (10) using protrusions or keys (65) that match corresponding slots or keyways on the drive unit and the connection may be fixed, e.g., non-reversible, using locking aperture (66) of the needle unit that is engageable with a corresponding sloped protrusion on the drive unit.

Figure 8:
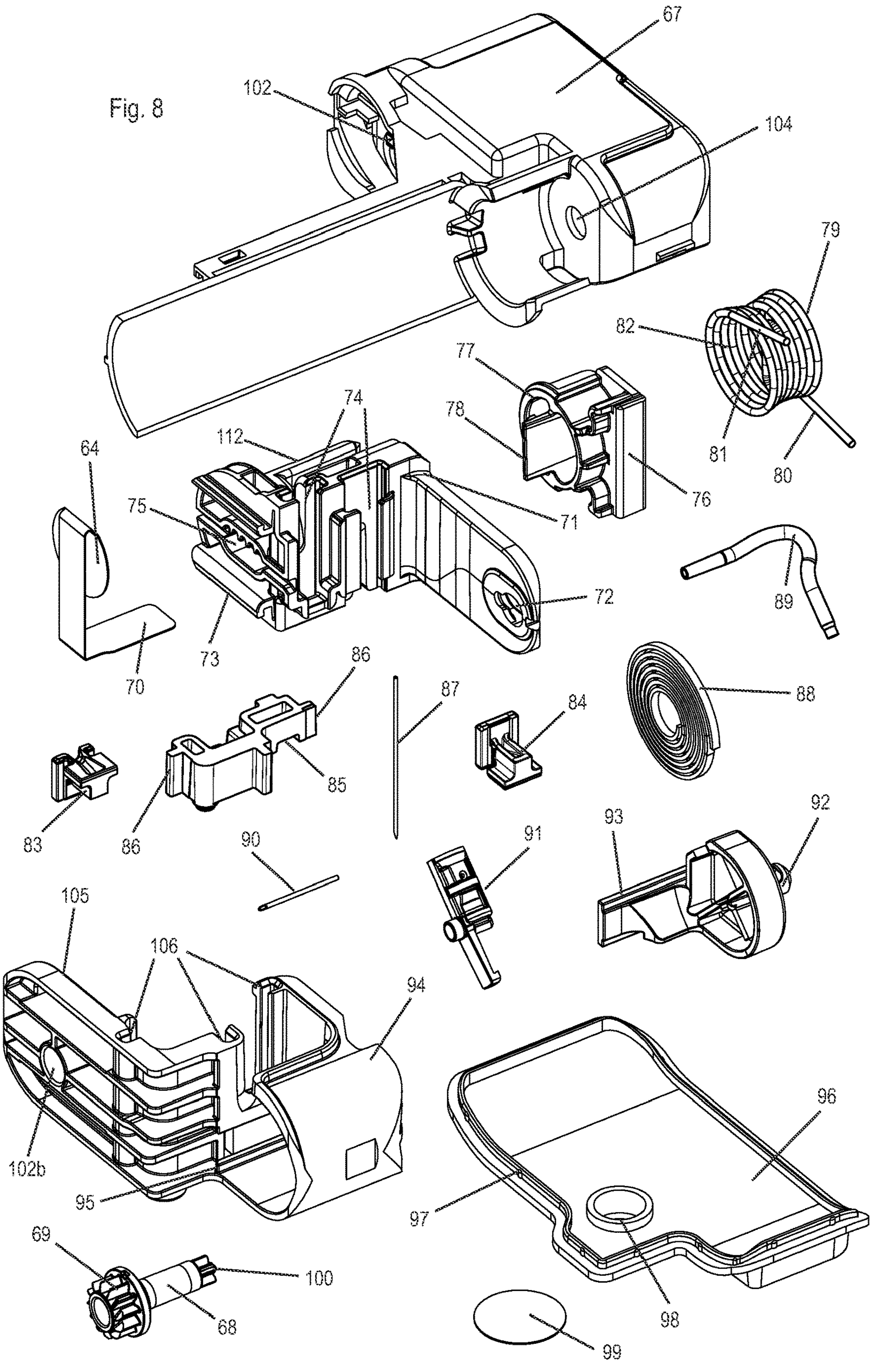
FIG. 8: Exploded view showing all components of the needle unit.

An exploded view with the components forming the needle unit is displayed in FIG. 8 and comprises a needle housing (67) enclosing a fluid path and the components for the needle insertion and retraction mechanism. The needle housing is part of the enclosure forming a sterile barrier preventing contamination of the fluid path and passages (102, 104, 98) in the needle housing need to be sealed or covered accordingly. The passage (104) for a cartridge needle is covered by a sterile barrier film (64) that may be removed from the needle housing using a pull tab (70) guided to the outside or an outside surface of the injection device.

The needle housing (67) comprises a mechanism holder (94) which provides structural support to a slider (71), a skin needle holder (85), a cartridge needle slider (92) and the cam shaft (68). The mechanism holder (94) is a separate part of the needle housing (67) but functionally behaves as an integrated part of the needle housing (67).

The slider (71) may move parallel to the bottom surface of the housing unit between discrete lateral positions and the movement is controlled by the PCB unit and driven by the drive unit. The lateral movement is guided by linear keys (73) that engage linear guides (105) of the mechanism holder (94). The slider (71) comprises a gear rack (75) for driving the slider in the latter direction by the cam shaft that is coupled to the gear mechanism (46,39,40,35) of the drive unit. The slider (71) comprises linear guides (74) that engage spring sliders (83, 84), the linear guides are oriented perpendicular to the movement direction of the slider, or, in other words, parallel to the skin needle insertion direction. Furthermore, the slider has an extension comprising a locking fork (72) which holds a cartridge needle slider in a retracted position.

Figure 8A:
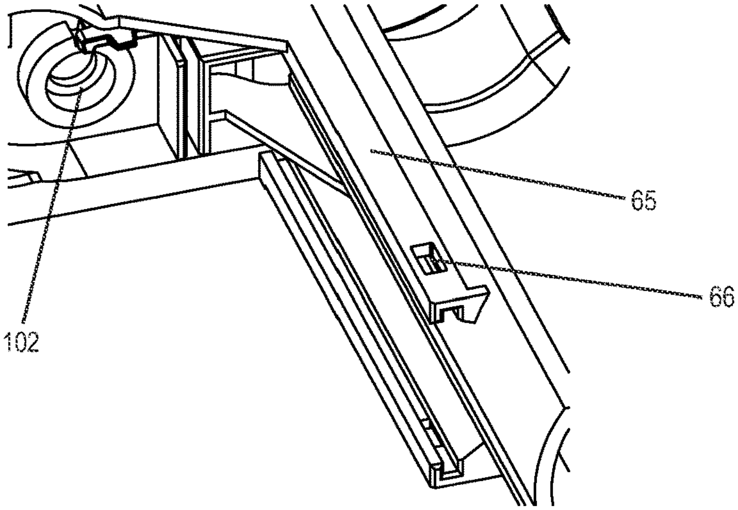
FIGS. 8*a*-8*r*: Individual component needle unit.
Figure 8B:
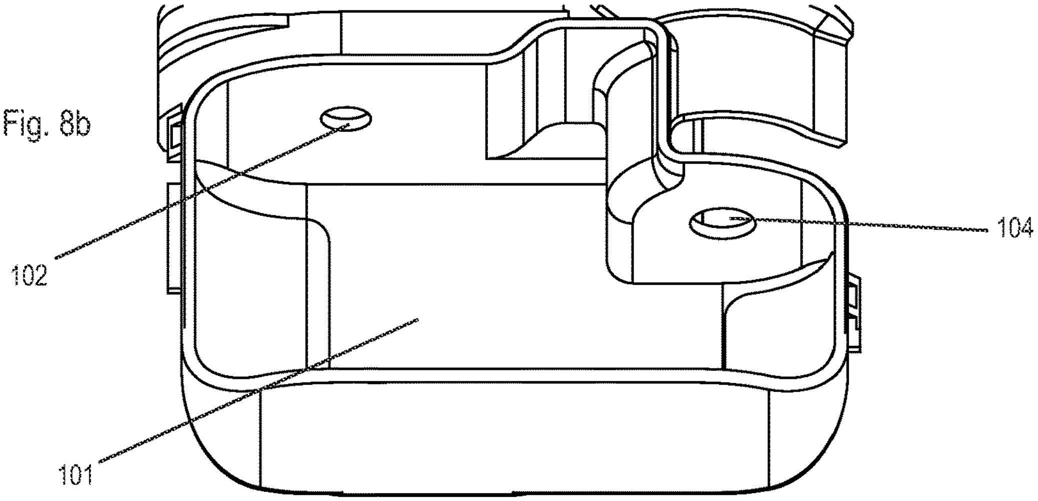
Figure 8C:
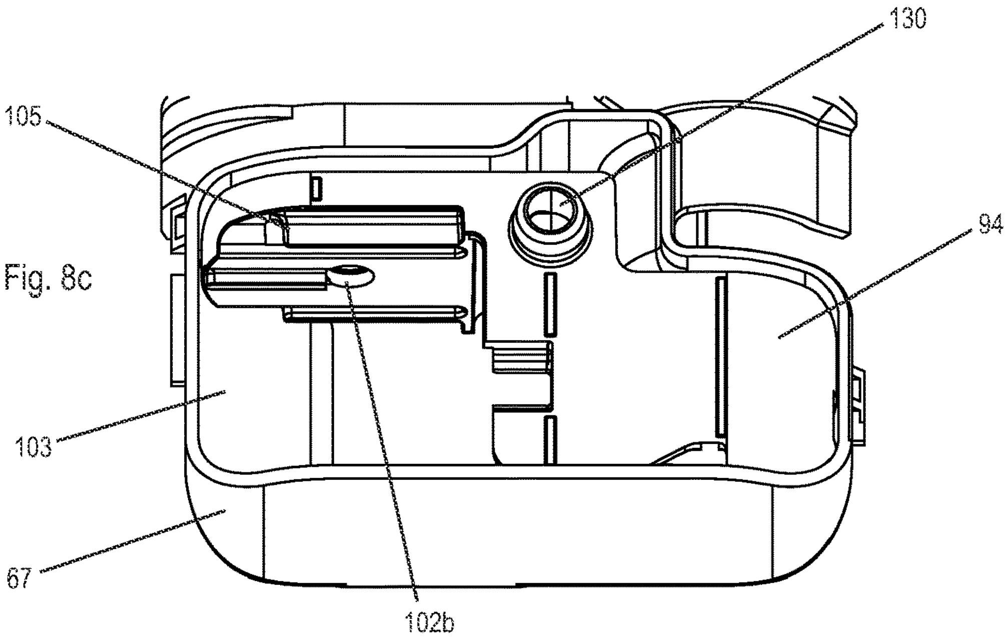
Figure 8D:
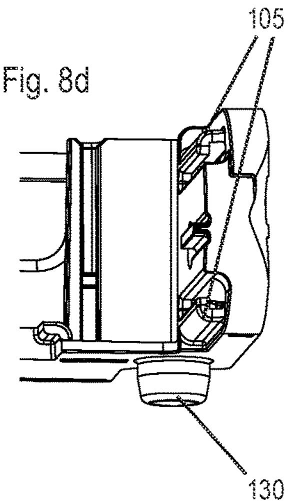
Figure 8E:
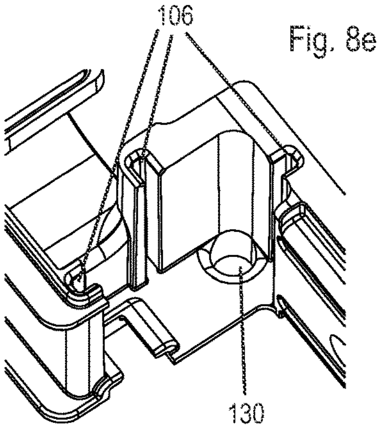
Figure 8F:
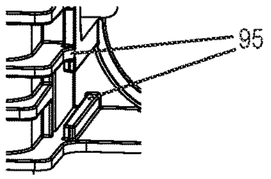
Figure 8G:
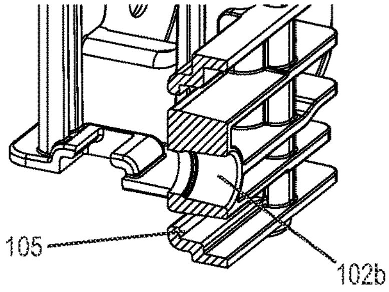

The slider (71) comprises a spring holder (112, see FIG. 8*k*) for holding a torsional spring (79), thus the torsional spring (79) follows the lateral movements of the slider. The torsional spring (79) is fixated after insertion into the spring holder using a spring fixator (76). The torsional spring (79) has an upper leg (81) and a lower leg (80) connected by a coil (82). The coil (82) biases the two legs towards each other when the torsional spring is assembled in the needle unit. The coil (82) has a connecting bar (117) connecting two parts of the coil spring that ensure that the two legs are biased towards each other when tensioned (FIG. 8*m*). The upper leg (81) biases an upper spring slider (83) and the lower leg (80) biases a lower spring slider (84) as will be described in detail below. The connecting bar (117) is configured to be inserted into a receiving pocket (113) of the spring holder (112) and the coil (79) surrounds the spring holder.

The mechanism holder (94) supports a skin needle holder (85) and has linear guides (106) to guide the skin needle holder (85) for moving perpendicular to the bottom surface of the housing unit of the injection device. The skin needle holder (85) has a plurality of protrusions or keys (86) that engage the linear guides (106) of the mechanism holder for guiding the skin needle holder from a needle retracted to an inserted position and from the inserted position back to the retracted position. The skin needle holder (85) is driven by the torsional spring between those two positions using the two legs. The skin needle holder (85) holds the skin needle (87) which is a hollow steel needle that is fluid tight sealed into the holder, for example using a rigid or flexible glue. The skin needle holder comprises a passage connecting the needle to an outlet in the holder adapted to receive a tube (89).

The tube (89) provides a fluid conduit between the skin needle (87) and a cartridge needle (90). The cartridge needle is inserted and attached (for example using an adhesive) to a cartridge needle holder (91) which provides mechanical support to the cartridge needle (91) and connects the needle to the tubing (89). The cartridge needle holder (91) may be an integrated part of, or inserted into a cartridge needle slider (92). The cartridge needle slider (92) has guides (93) which engage slots or keyways (95) of the mechanism holder (94) that allow for axial movement of the cartridge needle slider (92) parallel to the bottom of the injection device. The lateral movement of the slider (71) may be perpendicular to the movement of the cartridge needle slider (92). The cartridge needle (90) can be moved from a retracted position inside the needle unit to an extended position outside the needle unit thereby passing through the passage (104), for example after removing the sterile barrier (64). The cartridge needle (90) may be a hollow steel needle with a sharp tip that is open, or alternatively the steel needle is a pencil tip needle with a closed tip and a lateral opening. Optionally, plastic needles or spikes may be used.

The needle unit (11) further comprises the cam shaft (68) comprising the gear wheel (100) for the gear rack (75) that is located on the slider (71) inside the needle housing (67), and a gear wheel (69) located outside the needle unit and configured for engaging the gear mechanism of the drive unit (10). The cam-shaft (68) is rotatably received by the passage (102) of the needle housing and a corresponding passage (102*b*) in the mechanism holder. A sealing is present between the cam shaft (68) and the needle housing (67) and/or the mechanism holder, to prevent contamination of the fluid path enclosed by the needle housing. Such a sealing may comprise an elastic element such as an O-ring or V-ring surrounding the cam shaft and being in a press-fit engagement with a housing part.

The needle housing has an opening or fluid path compartment (101, FIG. 8*b*) that is closed by a needle cover (96) which encloses the fluid path after insertion and mounting of all components into the fluid path compartment (101). The needle cover may be substantially flat or may have angulated ends (winglets) such as shown in FIGS. 8, 16*a* and 16*b*. Alternative shapes for the needle cover will be described below. The needle cover (96) has a sealing rim (96) which may be fixated in a corresponding recess of the needle housing (67) to form a tight seal preventing contamination of the fluid path compartment. The needle cover may be made from a plastic material that is welded, for example laser welded or ultrasonic welded onto the needle housing. The needle cover (67) comprises an aperture (98) for the skin needle (87) which is closed by a sterile barrier film (99) (FIG. 17). The sterile barrier films (99, 64) may be made from a porous membrane allowing for chemical sterilization techniques such as gas plasma or ETO sterilization. An example is a non-woven polyethylene fiber membrane, such as the Tyvek membrane.

Details of the components forming the needle unit will be described in FIGS. 8*a* to 8*r*. A detail of the key (65) and the locking aperture (66) of the needle unit (67) is shown in FIG. 8*a*. The key (65) may engage a connecting ridge (189) that is part of the drive unit (FIG. 5*h*) and once the locking aperture (66) engages the locking protrusion (190), then the drive unit (10) and needle unit (11) are irreversibly attached to another. The fluid path compartment (101) that provides part of the sterile enclosure for the fluid path is shown in FIG. 8*b*. The apertures (102, 104) for the cam shaft and cartridge needle are part of wall sections oriented perpendicular to the bottom surface of the fluid path compartment. The passage (102) for the cam shaft (68) on the outside surface of the wall section has a protruding rim for mechanical support and/or fixation of the sealing element as can be seen in FIG. 8*a*. The mechanism holder (94) fits into the fluid path compartment, for example by press-fit or by another locking means such as a snapper or by an adhesive connection. See FIG. 8*c*, which represent a view from the below of the device showing the aperture for the skin needle (130) in the mechanism holder (94). The passage for the cam shaft (102*b*) in the mechanism holder is aligned with the passage (102) of the needle housing (67) and a compartment (103) is available for the slider to move laterally as the slider is guided by the guides (105) of the mechanism holder (94), see also FIG. 8*d* (representing a view from the side of the mechanism holder). The linear guides (106) for engaging the skin needle holder (85) are shown in a top view on the mechanism holder in FIG. 8*e* whereas details for the keyways (95) guiding the cartridge needle slider and details of the passage for the cam shaft (102*b*) can be seen in cross sections in FIGS. 8*f* and 8*g*, respectively.

Figure 8H:
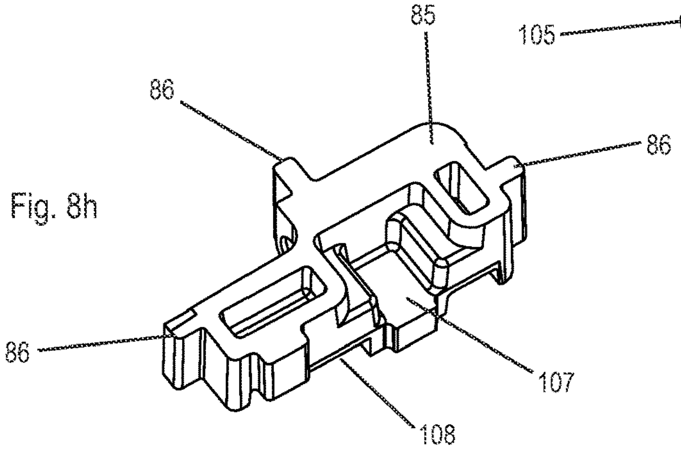
Figure 8I:
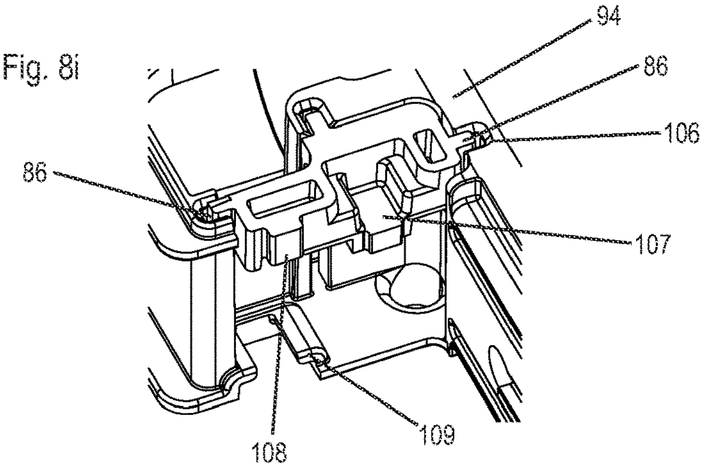

The skin needle holder (85) in FIG. 8*h* comprises next to the linear keys (86) receiving sections (107, 108) for the upper spring slider (83) and the lower spring slider (84). The key-keyway engagement (86, 106) guides the skin needle holder in the mechanism holder such that the skin needle holder can only move in the needle insertion direction. The receiving sections (107, 108) have an engagement surface for the spring sliders such that forces from the legs of the torsional spring may be transferred to the skin needle holder while the spring sliders can move on the engagement surface in a direction that is perpendicular to the skin needle insertion direction. The assembly of the mechanism holder (94) and the skin needle holder (85) is shown in FIG. 8*i*, with the skin needle holder in the needle retracted position.

Figure 8J:
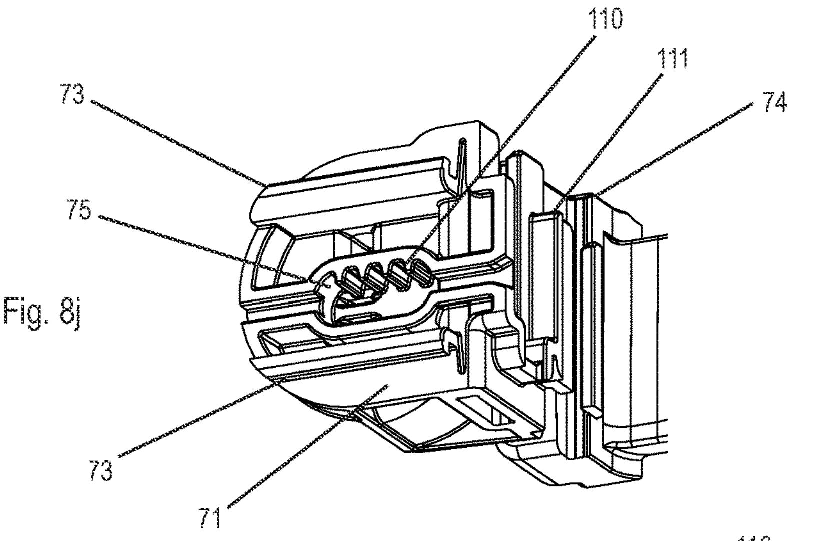
Figure 8K:
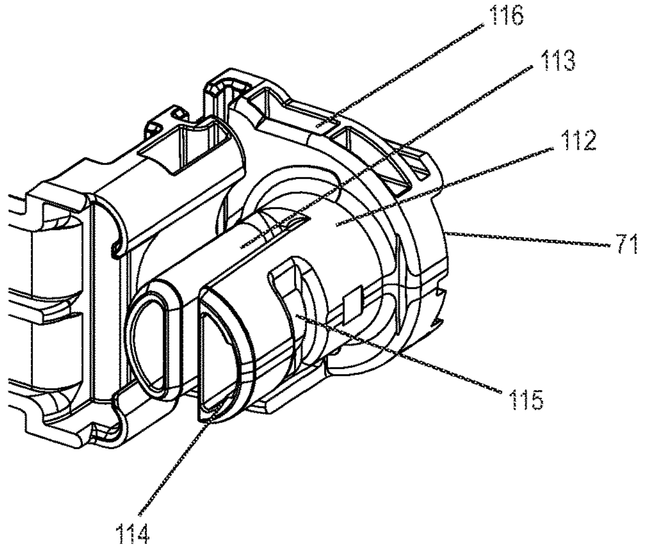
Figure 8L:
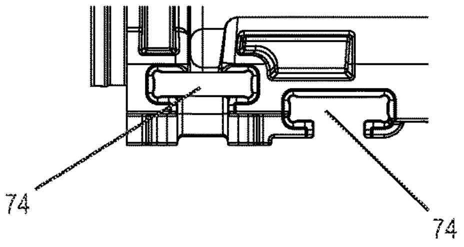
Figure 8M:
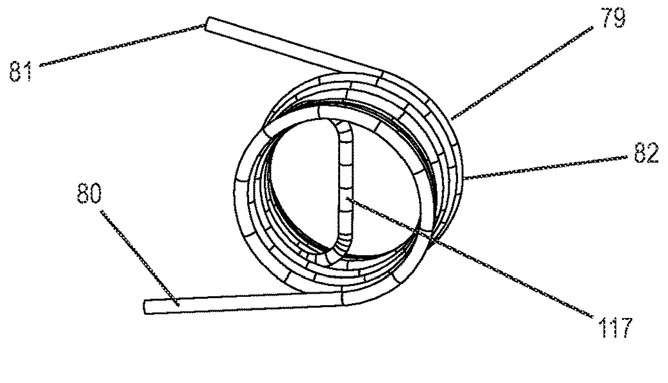

The needle control element or slider (71) comprises the linear keys (73) for engaging the mechanism holder, and two linear guides (74) for engaging the spring sliders (83,84). The slider further comprises a stop surface (111) that is adapted to abut a surface, for example a bottom surface, of the skin needle holder (85) for keeping the skin needle holder in a retracted position. The slider (71) comprises a gear rack (75) having gear teeth (110) that may engage the gear wheel (110) of the cam shaft. The linear guides together with the gear rack-gear wheel interaction (75,110) ensure that the slider can move in the lateral direction (FIG. 8*j*). A top view of a section of the slider (71) showing the two linear guides (74) that may engage the spring sliders (83, 84) is presented in FIG. 8*l*. The spring sliders (83,84) are keyed to the slider such that they can move up and down in the guide (74) while they have to follow the lateral movement of the slider (71). A spring holder (112) is attached to, and protrudes from a base (116) of the slider (71). The spring holder (112) has a circular outer shape that is split apart by a receiving pocket (113) and further comprises a cut-out (115) that is configured for attaching the spring fixator (76) thereto. The receiving pocket receives and rotationally fixates the bridging bar (117) of the torsional spring (79) to the slider. Furthermore the receiving pocket together with the connecting bar provides the counterbalance for the two legs of the spring when tensioned. Thus the lateral movement of the slider (71) will be followed by the torsional spring (79) with the upper and lower spring legs (84, 85), by the upper and lower spring sliders (83, 84) and by the locking fork (72).

The assembly of the torsional spring (79) onto the spring holder (112) is shown in FIGS. 8*n* and 8*o*. First the coil spring (79) is mounted onto the spring holder (112) whereby the bridging bar (117) is inserted into the receiving pocket. The bridging bar (117) abuts a surface (118) of the slider and the spring fixator (76) is mounted onto the end section (114) of the spring holder (112) whereby a wing (78) of the fixator fits into the receiving pocket and pushes the bridging bar (117) towards the abutment surface (118) of the slider (71). The fixator has a flexible arm with a protrusion that snap fits into the cut-out (115) of the spring holder and locks the spring to the slider.

The upper spring slider (83) and the lower spring slider (84) are shown in FIGS. 8*p* and 8*q*, respectively. The upper spring slider (83) comprises a key (120) that engages the linear guide (74) of the slider (71). Furthermore the slider has an opening (123) for receiving the upper leg (81) of the torsional spring into a receiving section (122) of the upper slider. The lower spring slider (84) may be identical to the upper spring slider but oriented upside down and showing a holding surface (124) which is intended to engage a locking member (109) that is present on the mechanism holder (94). The assembly of the upper and lower spring sliders engaging the linear guides (74) of the slider (71) is presented in FIG. 8*r*.

The tube or conduit (89) connecting the skin needle holder (85) to the cartridge needle holder (91) is presented in FIG. 9. The ends of the tube are inserted into the holders and fluid tight connected by a press-fit of the elastic tubing material, or the ends are adhesively connected to the holders.

The cartridge needle holder (91) has a locking feature (125), for example a locking arm or a snapper that may engage the cartridge needle slider (92). A detail of the cartridge needle slider (92) is shown in cross sectional view of FIG. 11. The cartridge needle slider (92) is engaged with the mechanism holder (94) through the key-keyway engagement (95, 93, FIGS. 8, 8*f*) and can move from a retracted position to an extended position parallel to the bottom surface of the device. The cartridge needle slider spring (88) is positioned and compressed between the mechanism holder (94) and the cartridge needle slider (92) thereby biasing the slider to move towards the inserted position. The cartridge needle slider is retained in the retracted position by knob (126) that is part of the cartridge needle slider (92) which engages the locking fork (72) of the slider (71). As a consequence, the slider (71) is pushed against the mechanism holder (94). Once the slider (71) is moved in a lateral direction, for example from a starting position to an intermediate position, then the engagement between the fork (72) and the knob (126) is released and the cartridge needle slider (92) moves together with the cartridge needle (90), the cartridge needle holder (91) and the end of the flexible tube (89) towards the passage (104) of the fluid path compartment. The engagement between the fork (72) on the slider and the knob (126) on the cartridge needle slider (92) is such that the abutment surfaces between the knob (126) and the fork (72) of the slider are essentially perpendicular to the needle axis of cartridge needle (90). The slider (72) is pressed against the mechanism holder (94) which may lead to an increased frictional resistance that needs to be overcome when moving the slider. An alternative embodiment for reducing the frictional losses whereby the slider releases an intermediate member is described further below.

The cartridge needle (90) will at least partially go through the passage for penetrating a septum of the cartridge unit. A detailed view of the cartridge needle slider spring (88) is shown in FIG. 10. The spring may be a tapered coil spring having the advantage of a space saving arrangement when the spring is compressed as the coil sections do not abut each other when compressed.

The assembled needle insertion and retraction mechanism and the fluid path is shown in FIG. 12. The slider (71) is in the starting position and can move due to rotation of the cam shaft (68) in the lateral direction as the slider (71) is guided by the mechanism holder (94). The upper leg (81) of the torsional spring (79) presses onto the upper spring slider (83) which itself presses onto the receiving section (107) of the skin needle holder (85). The skin needle holder is kept in the retracted position against the bias of the spring force as will be explained in FIG. 13. The torsional spring (79) is locked to the slider (71) by the spring fixator (76) and the locking fork (72) engages the knob (126) of the cartridge needle slider. The skin needle holder (85) is kept in the retracted position when the slider (71) is in the starting position due to the stop surface (111) of the slider (71) abutting the lower surface of the skin needle holder (85), FIG. 13.

Details of the cam shaft (68) with the two gear wheels (69, 100) at each end is shown in FIG. 14, and a cross section of the cam shaft going through the passages (102, 102*b*) of the needle housing and the mechanism holder in FIG. 15. The gear wheel (69) at one end of the cam shaft (68) is located on the inside of the (sterile) fluid path compartment whereas the gear wheel (100) at the other end is located outside of the needle housing (non-sterile). An O-ring forms a seal between the housing and the cam shaft preventing contamination of a sterile fluid path compartment and providing a frictional resistance for rotating the cam shaft (68). The needle cover (96) comprising the aperture (98) for the skin needle is shown in FIG. 16*b*. The outside surface of the needle cover (FIG. 16*a*) has a sealing surface (128) and a circumferential rim (129) that surrounds the aperture (98) and sealing surface. The barrier film (99) may be attached to the sealing surface (128) only and not to the rim (129) (FIG. 18). The attachment has an adhesive strength F1 which is 6 Newtons at the most. The rim acts as a support for attaching the surface of the barrier film (99) to an adhesive layer, for example a strengthening film or to the release liner itself, for example with and adhesive strength F3 that is at least 10 Newtons. During removal of the sterile film (99), either using the release liner or via the strengthening film, then the film (99) may not be attached to the circumferential rim (129) as this will facilitate the roll-off or peel-off of the sterile film (99) from the sealing surface (128). The needle cover (96) may have a bottom surface essentially parallel to the bottom surface of the housing unit HU with two winglet sections at each end that are angulated (FIG. 16*a*, 16*b*).

Figure 19:
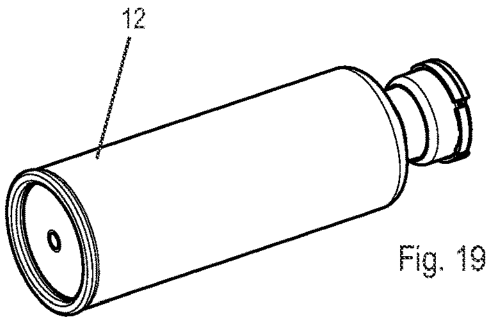
FIG. 19: Cartridge unit (CU)
Figure 20:
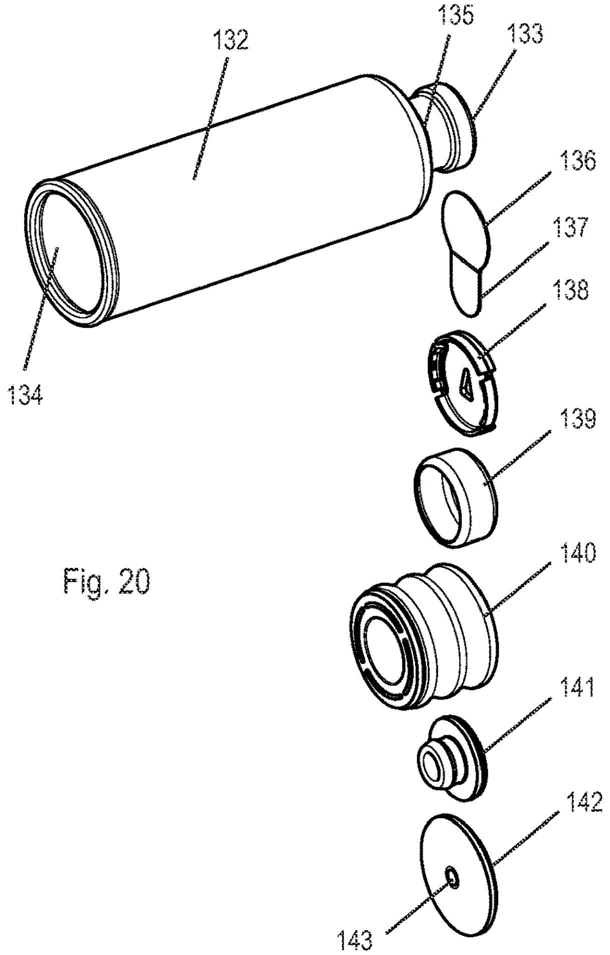
FIG. 20: Exploded view showing components of the cartridge unit.

The assembled cartridge unit (12) is shown in FIG. 19 and a detailed view of the individual parts in FIG. 20. The cartridge unit (12) comprises a barrel (132) which is a hollow cylinder having a distal opening (133) and a proximal opening (134). At the distal end, the barrel has a neck (135) area with a lower diameter compared to the proximal barrel section. The distal opening (133) is closed by a pierceable septum (141) which is attached to the neck using a crimp cap (139). The crimp cap has an opening that is available for a needle or spike for penetrating the septum (141). A sterile barrier film (136) may be attached to an end wall of the crimp cap thereby covering the opening of the crimp cap and the septum's surface underneath. The adhesive strength F1 between the crimp and the barrier film is 6 Newton or less. The sterile barrier film (136) is glued, welded, heat welded or otherwise sealed to the surface of the crimp cap thereby forming a protective layer for the surface of the septum. The sterile barrier film (136) may be a film made from porous non-woven fibers and the porosity allows for chemical sterilization agents to pass through. The sterile barrier film (136) has a pull tap (137) which is an integral part of the porous film or a separate film connected to the sterile barrier film (136). The pull tab may require an additional connection surface between an end of the pull tab (137) and the sterile barrier film (136) with an adhesive strength F2 that may be 10 Newton whereas the other end of the pull tab is connected to the release liner with an adhesive strength F3 which is above 10 Newton. The pull-tab (137) may be guided to the outside or an outside surface of the injection device such that the barrier film may be removed by pulling the tab. The sterile barrier film (136) and/or the pull tab (137) may be folded to promote the peel-off, or roll-off, of the sterile barrier film (136) from the crimp cap. The sterile barrier film and/or pull tab may be guided around pins or wheels within the housing unit to facilitate film removal, for example using a pulley system.

The cartridge unit (12) may comprise a flip-off cap (138) covering the sterile barrier film (136). The flip-off cap (136) may be attached to the crimp (139). The flip-off cap (138) protects the sterile barrier film during handling of the cartridge unit and the cap may be removed just prior to inserting the cartridge unit (12) into the housing unit of the injection device. The flip-off cap (138) may have openings to enable sterilization of the sterile barrier film (136) and the septum's surface and/or penetration of a needle. The flip-off-cap (138) may be made from a plastic material and attached to the crimp cap using heat welding, laser welding or ultrasonic welding. The crimp cap (139) may be made from a metal such as aluminum. Furthermore, the flip-off cap (138) may have perforated sections forming predetermined breaking points for easy flip-off cap removal. The parts of the flip-off cap remaining on the crimp cap may be used to position the correctly cartridge unit in the housing unit, for example the angular position.

A plunger (140) is moveably positioned within the proximal opening (134) of the barrel (132) thereby forming a sealing for the medicament that is enclosed in the cartridge. The plunger may be moved by the piston rod (31) of the drive unit (10) during medicament delivery. The plunger may be placed at different axial positions in the barrel for cartridges having different fill volumes of the medicament. It may be beneficial to have the piston rod (31) at a fixed starting position (or retracted position) and compensate the gap between the end of the piston rod (31) and the proximal end of the plunger (140) using a spacer (142). The spacer (142) compensates for the gap and is beneficial for a homogeneous distribution of the forces from the piston rod to the plunger (140). Optionally, a pivot bearing (143,50) is formed between the protrusion (50) on the distal end of the last segment of the piston rod and a bearing surface (143) present on a proximal surface of the spacer (142). The bearing surface (143) may be a recessed section matching a ball shaped protrusion on the end of the piston rod to form a ball in a socket bearing. Alternatively one of the two surfaces is flat and abutting a ball shaped protrusion for a ball on plate bearing.

Figure 21:
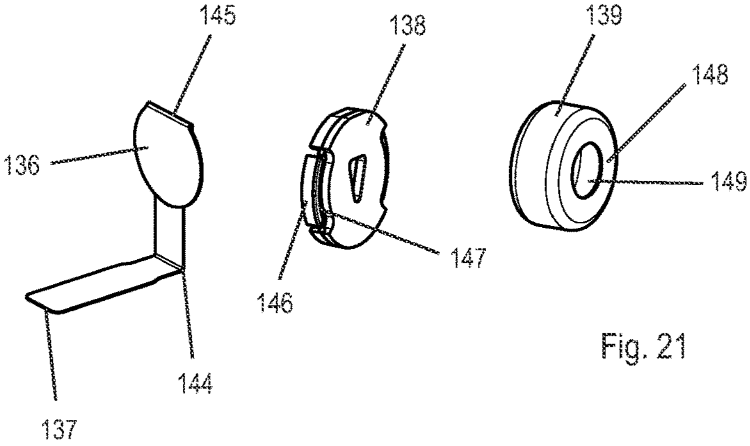
FIG. 21: Details of the sterile barrier film, flip-off cap and crimp of the cartridge unit.
Figure 22:
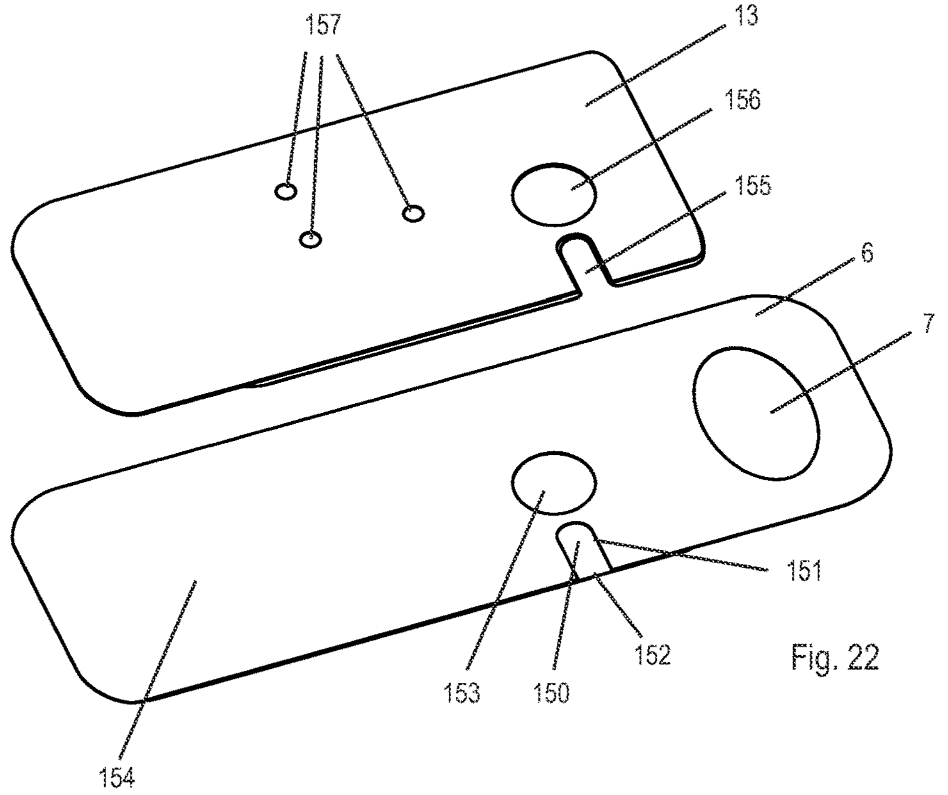
FIG. 22: Components sensing patch unit (SU)

FIG. 21 shows a detailed view of the flip-off cap (138), the crimp cap (139) and the sterile barrier film (136). The crimp cap has an end surface (148) with an aperture (149) for the cartridge needle. The end surface (148) is used for attaching the sterile barrier film (136) to the crimp cap. The sterile barrier film (136) may be heat sealed to the crimp cap. The surface of the crimp cap may be heat treated, etched, roughened or coated with an adhesion promotor to enhance the connection between the sterile barrier film (136) and the crimp cap. The sterile barrier film on the other hand may be treated as well for promoting adhesion to the crimp cap, for example by coating or dipping the barrier film with an adhesive or an adhesion promotor. This may also reduce the amount of particulates released from the barrier film, for example under vacuum or in a clean room or sterile environment. The flip-off cap (138) comprises connectors (146) for connecting to the crimp cap (139) and predetermined breaking points (147) facilitate the controlled release of the flip-off cap from the cartridge unit. The sterile barrier film (136) and/or pull tab (137) may have an internal fold (145) that is located inside the housing and the pull tab (137) may have an additional external fold (144) located outside the housing when the device is assembled.

Figure 23:
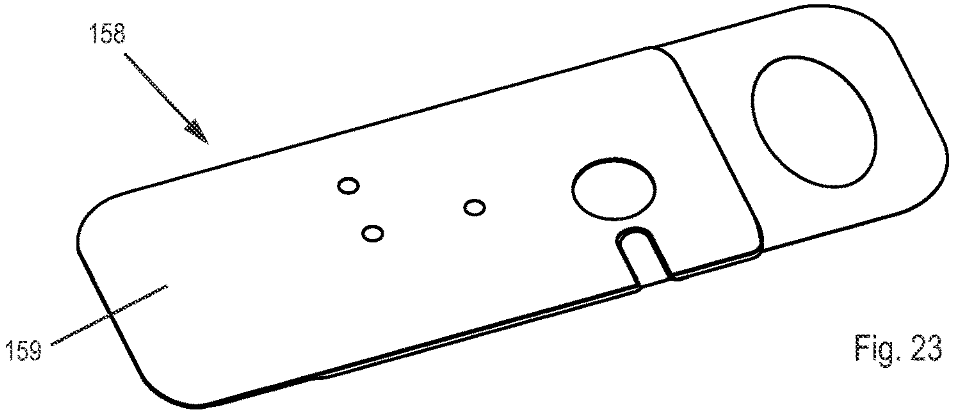
FIG. 23: Sensing patch unit assembled with release liner.
Figure 24:
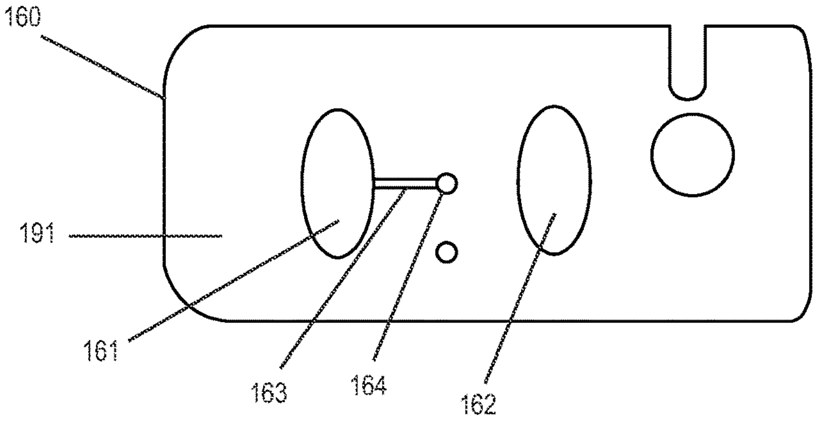
FIG. 24: Sensor layer in sensing patch.

A detailed view of the sensing patch unit (13) is given in FIGS. 22, 23, 24 and 25. The sensing patch unit (13) comprises an aperture, for example a circular aperture (156) in the film, that is available for the skin needle. Furthermore the sensing patch unit (13) has an opening, or at least semi-open aperture, for example a notch shaped opening (155) located at a rim of the film-shaped unit, which is available for inserting the sterile barrier films from the needle unit and/or the cartridge unit. The sensing patch unit (13) further comprises contact points (157) located in the top surface that may contact the contact springs (29) for connecting the sensing patch unit to the printed circuit board unit. The release liner (6) for the sensing patch unit may comprise a conductive layer (154) that at least partially covers one or both of the surfaces of the release liner. The conductive layer (154) may be a coated or a printed metal layer on top of a polymeric sheet of material forming the base for the release liner. Examples are a silver ink layer or an aluminum or gold layer deposited onto the surface. Alternatively a non-metallic coating may be used, for example a carbon black coating. The release liner has an aperture (153) for the skin needle that is aligned with the aperture (156) of the sensing patch unit (13). The release liner has a notch (150) that is located at a rim of the release liner and aligned with the notch (155) of the sensing patch unit such that the sterile barrier films may pass through the sensing patch unit (13) and the release liner (6). The notch (150) has an opening (152) located at an edge of the release liner and the notch may have two legs that start at the opening (152) to form a U-shaped notch. The assembly of the sensing patch unit (13) and the release liner is shown in FIG. 23, the top layer (159) facing the housing unit comprises an adhesive for attachment to the device. The sensing patch unit (13) comprises at least one sensor layer (160) that is located between the adhesive layer (159) connecting the patch to the housing and the release liner (6). The sensor layer (160) comprises a sensor area (161) that is connected to contact (164) using electrically conductive leads (163). The contact (164) is connected to one of the contacts (157) present in the top layer (see FIG. 22) such that signals can be transmitted from—and to—the sensor (161) via the contact springs (29). The sensor layer (160) may have at least one second sensor area (162) that is connected via a separate lead that is not shown to the contact springs. The sensor area (161) and second sensor area (162) each form a capacitive sensor where each capacitance depends on the dielectric present adjacent to the sensors (skin or air) and/or the presence of an electrical shielding that may be present in the release liner. The latter enables the electronic detection of the release liner removal. The sensing patch unit may further comprise additional sensor areas and/or sensor layers and grounding layers present between the several layers to reduce the signal to noise ratio and improve the accuracy of the capacitive measurements. Furthermore isolation layers may be present between two layers having conductive leads.

The sensor layer may have one sensor area (161) only.

The sensing patch unit further comprises a skin adhesive layer (191) that is adjacent to the release liner. The skin adhesive layer (191) is the outermost layer of the sensing patch unit when the sensing patch unit is attached to the housing using the adhesive top layer (159).

Figure 25:
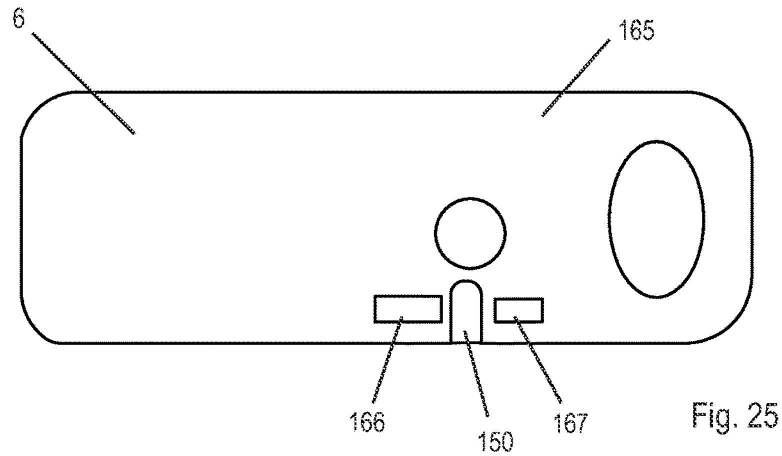
FIG. 25: Release liner, bottom view on surface not attached to skin adhesive layer.
Figure 26:
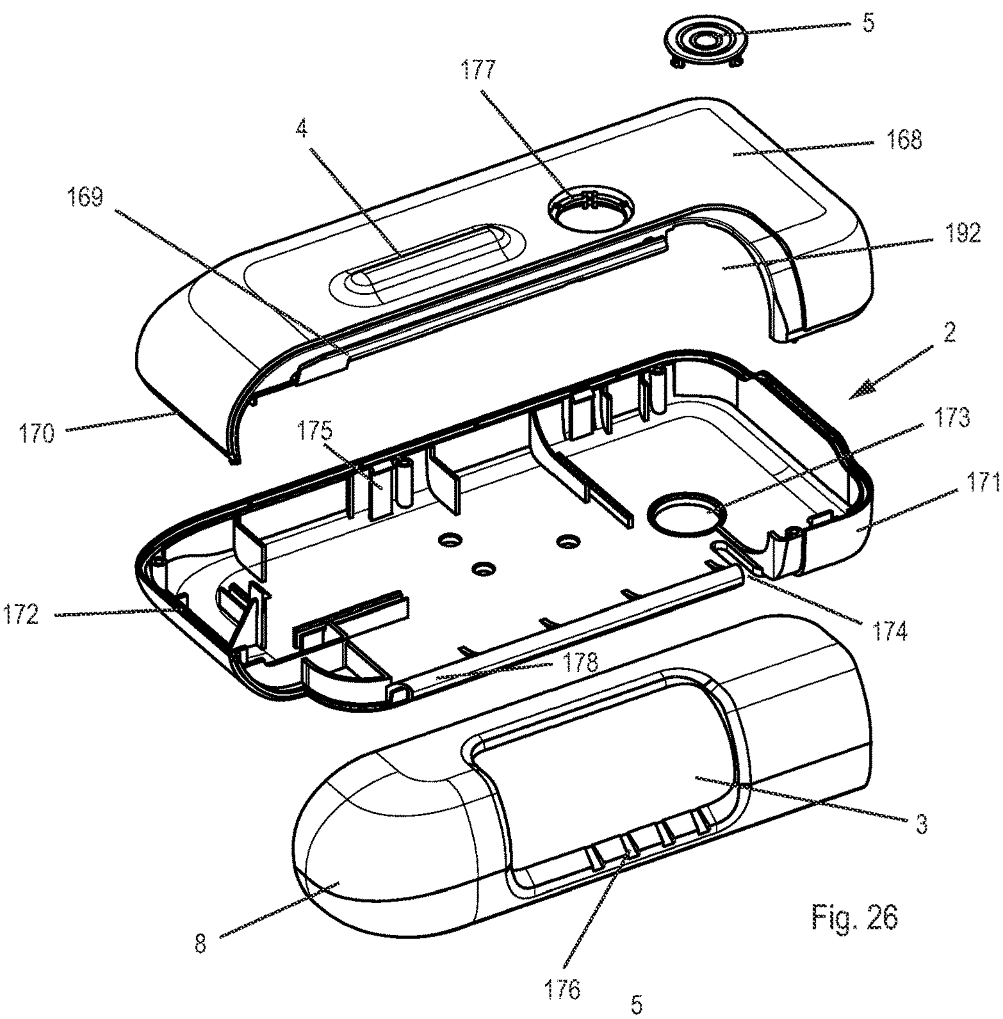
FIG. 26: Exploded view housing unit (HU)

A bottom view of the release liner (6) is shown in FIG. 25. The backside surface (165) that is not in contact with the skin adhesive layer (191) comprises adhesive or connecting spots (166, 167) that are each located adjacent from the notch (150) in the release liner. The adhesive spots are arranged to allow for attaching one or both of the sterile barrier films (64, 136) from the needle unit and/or the cartridge unit to the release liner's backside surface and may contribute to establishing adhesive strength F3. The spots may be opposite to another to ensure that both ends of the sterile barrier films (for example the ends of the pull tabs) are each connected to one side of the notch for an even stress distribution upon release liner removal. The adhesive spots may comprise double sided adhesive tape, a hot melt or a spot that is prepared for adhering or gluing the ends of the films (or pull tabs) to the backside surface (165) of the release liner. The surface of the release liner may be treated (roughened, etched, heat treated or coated with an adhesion promotor) to enhance the attachment between the release liner and the sterile barrier films, The housing unit (2) is presented in FIG. 26 and comprises a housing cover (168) forming the top surface of the injection device. The housing cover (168) comprises the indicator (4) which may be an elevated and semi-transparent section of the housing cover (16) such that underlying LED lights can shine through the indicator for showing a status of the device or of the injection procedure or for the connectivity to an external device. A plurality of LED lights may be used having different colors and/or different intensity and each of the plurality of LED lights may be separated from the other LED lights using partition walls there between. The housing cover (168) has an aperture (177) shaped to receive and hold the push button (5). The housing cover further comprises a guiding rib (169) for guiding the cover (8) of the housing unit during device assembly. The housing cover (168) is attached to a housing base (171) via a closure rim (170) engaging a matching rim (172) on the housing base. The connection may be an adhesive connection or the two parts may be welded (heat, laser, ultrasonic) together after assembly of the needle unit and drive unit into the housing unit. The housing base (171) comprises support flanges or snappers (175) to engage the drive unit and or the needle unit, and an aperture (173) for the skin needle. Housing base (171) has guiding rib (178) which forms together with the guiding rib (169) of the housing cover (168) guiding means to guide the cover (8) when closing the housing unit and fixating the cartridge unit in the cartridge holder. The cover (8) may have markings (176) printed onto or embossed in the cover (8) such that the user can monitor the fluid level in the cartridge through the viewing window (3). The viewing window may be sized or arranged such that plunger (140) cannot be seen via the window once the plunger (140) has been advanced to the final (most forefront, see FIG. 45) position. The housing base (171) comprises a notch (174) that is aligned in the assembled device with the notches in the release liner, the sensing patch unit and the needle housing (150, 155, 131) to form a passage for the sterile barrier film from the inside of the housing unit to the outside of the injection device or to an outside surface of the release liner.

Figure 27:
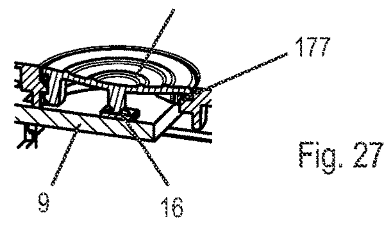
FIG. 27: Detailed view of push button in the housing unit.
Figure 28A:
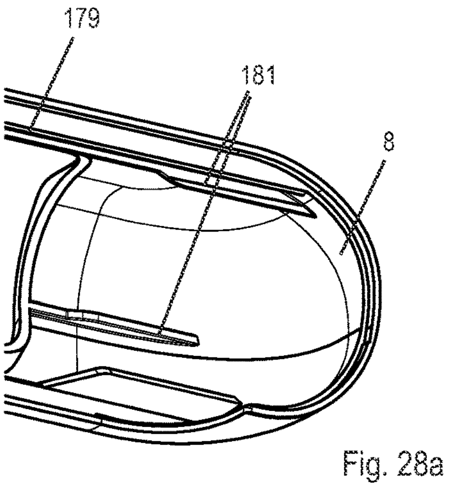
FIGS. 28*a*, 28*b*: Cover for housing unit.
Figure 28B:
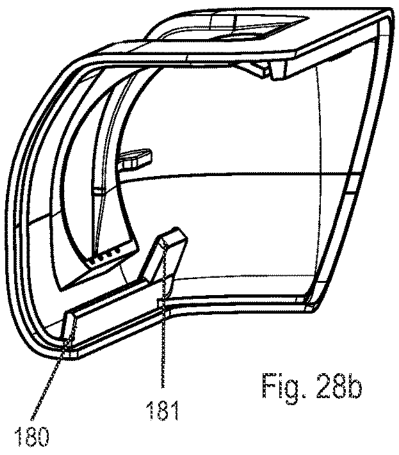
Figure 29:
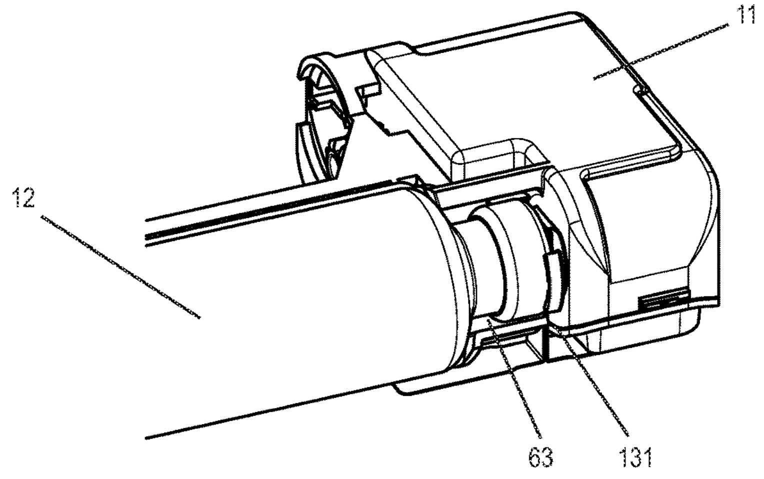
FIG. 29: Cartridge unit inserted in needle unit.
Figure 30:
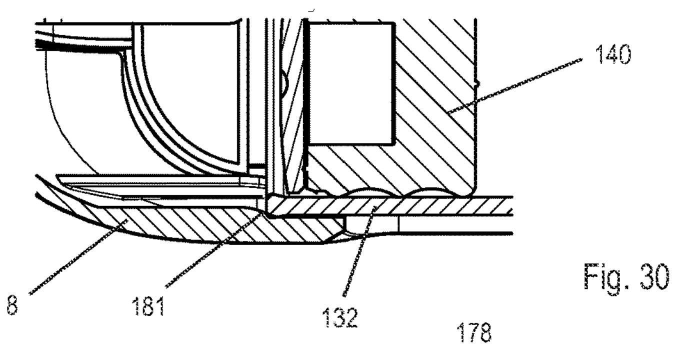
FIG. 30: Detail of cover housing unit fixating the cartridge of cartridge unit in the needle unit.

A detail of the push button (5) in the assembled device is presented in FIG. 27, showing the aperture (177) in the housing cover and the part of the PCB unit (9) below the aperture having the push button switch (16) contacted by a stem that protrudes from the push button. Once the sensing patch unit determines the removal of the release liner or device attachment to the skin, the push button switch is activated such that the injection may be started by pushing the button. Details showing the inside surface of the cover 8 are shown in FIG. 28*a* and FIG. 28*b*. A rib or keyway (179) of the cover may engage the guiding rib (169) of the housing cover and another rib or keyway (180) of the cover may engage the guiding rib (178) of the housing base, such that the cover (8) may be shifted over the opening (192) in the housing cover. A detail of the needle unit (11) with the cartridge unit (12) inserted into the cartridge holder is shown in FIG. 29. The cover (8) comprises deformable ribs or arresters (181) that engage a rim of the barrel (132) of the cartridge that is located at the proximal opening (134) and thereby fixating the cartridge in the device (FIG. 30).

Figure 31:
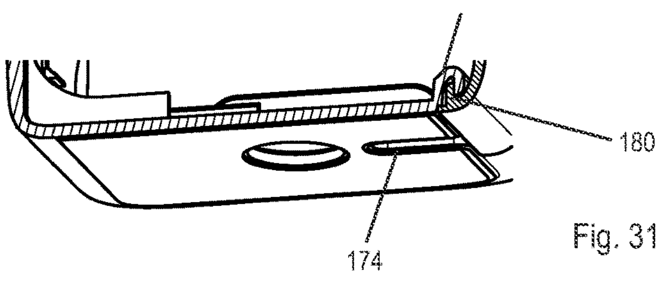
FIG. 31: Detail of cover housing unit closing the notch in the housing unit.

During assembly, the cartridge unit (12) is inserted in the cartridge holder of the needle unit (11). The sterile membrane (136) and/or the pull tab (137) may be inserted into the notch in the needle housing, for example from the side, and guided through the notch in the housing base, the sensing patch unit and the release liner such that the end of the sterile barrier or the pull tab may be attached to the outside surface of the release liner or is available for the user. The cartridge unit comprising the sterile barrier film (136) may be sideways inserted into the housing. Subsequently, the cover (8) is engaged with the ribs (169, 178) of the housing unit and moved to close the notch and prevent the sterile barriers from leaving the notch before liner removal (FIG. 31). During closure of the cover (8) the deformable ribs (18) are elastically and/or plastically deformed to axially or rotationally fixate the cartridge unit (12). The cover (8) may have a locking feature such as a protrusion or flexible arm engaging a counter locking feature on the housing cover or housing base to irreversibly lock the cover (8) to the housing unit.

Figure 32:
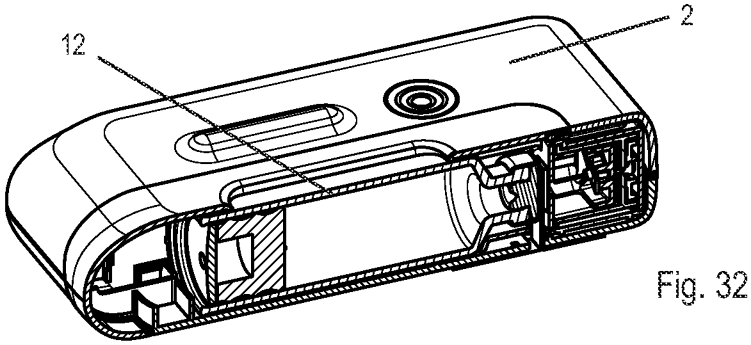
FIG. 32: Cross section of assembled injection device showing cartridge unit and needle unit.
Figure 33:
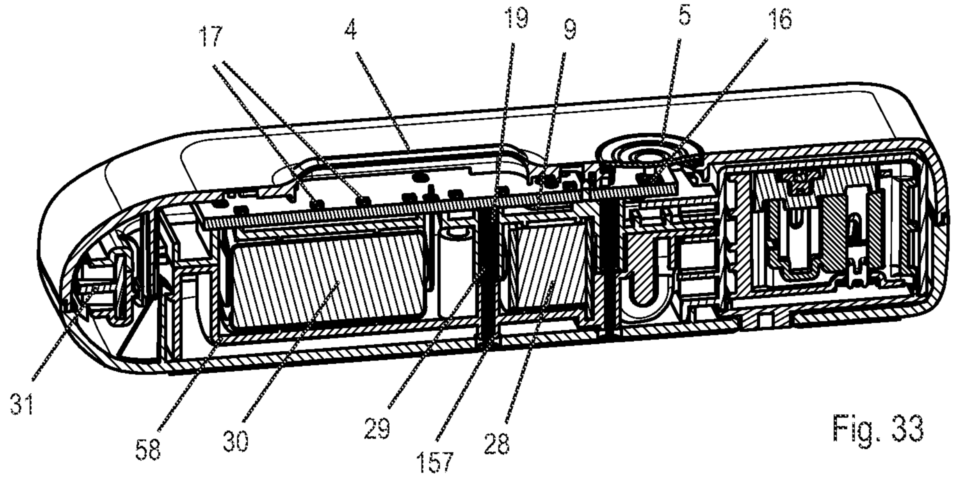
FIG. 33: Cross section of assembled injection device showing battery, electromotor and gear mechanism of the drive unit.

The assembled injection device including the cartridge unit (12) is shown in two cross sections taken in a plane through the cartridge unit (FIG. 32) and through the battery/stepper motor (FIG. 33). In FIG. 32, the plunger (140) can be seen via the viewing window as the plunger is in the starting position for a full cartridge. The cartridge unit (12) is oriented parallel to the bottom surface of the injection device and the septum is aligned with the passage in the needle housing such that the cartridge needle may move through the septum. The LED indicators (17) of the PCB unit are located below the indicator section (4) of the housing cover. In FIG. 33, there are no partition walls between the LEDs. The lower surface of the PCB unit (9) is contacted with the contacts (157) of the sensor layer in the sensing patch unit via the contact springs (29). The springs (29) are guided through the apertures (32, 56) in the drive unit. The battery (30) and the stepper motor (28) are fixated by form fit or an adhesive to the holder (58) of the drive unit.

Figure 34:
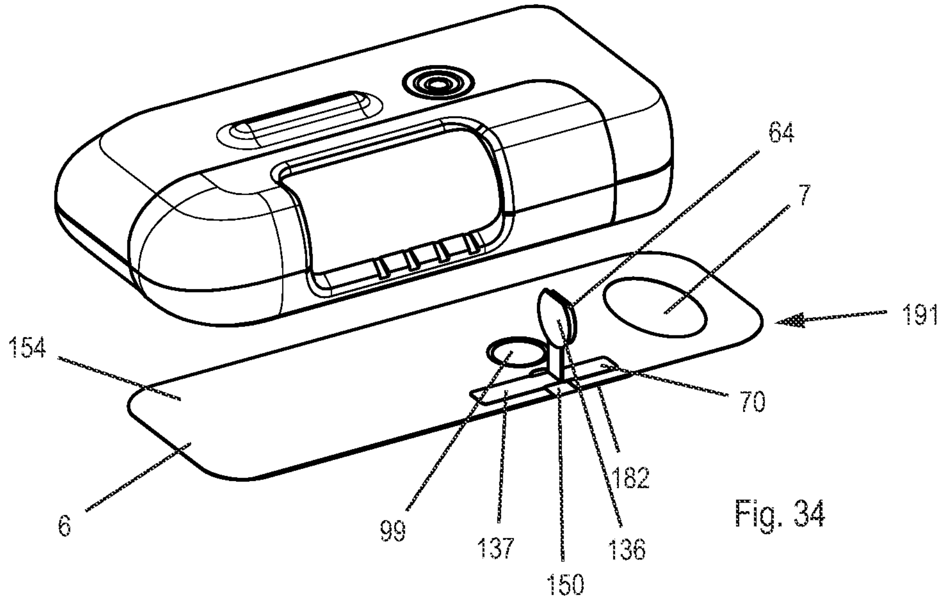
FIG. 34: Release liner removed from the injection device.

The functioning of the injection device will be described in the following. The electronic circuitry of the PCB unit (9) is powered by the battery (30) in the drive unit (10) throughout the lifecycle of the injection device, i.e., there is no separate switch closing the electronic circuit after shelf life (e.g., storage) and just prior to using the device. The status of the device may be monitored by measuring the signals from the sensor patch unit, for example at a low tact frequency to save battery power during shelf life. The user removes the injection device (1) from a packaging and selects a suitable injection location on the body while the release liner (6) is still attached to the skin adhesive layer of the sensing patch unit (13). The user grasps the gripping area (7) of the release liner and peels the release liner (6) from the skin adhesive layer as indicated by the arrow (191) in FIG. 34. As the liner is removed, the sterile barrier film (64) on the needle unit and/or the sterile barrier film (136) on the cartridge unit are peeled-off from the housing of the needle unit, respectively from the crimp cap of the cartridge unit. Both pull tabs (70, 137) may be connected to an outside surface (165) of the release liner on opposite sides of the notch (150) thereby ensuring that the sterile barrier films (64, 136) are removed one after another, and the forces are directed to different areas on the release liner thereby reducing the risk of liner fracture. The notch (150) in the release liner may be reinforced by a strengthening sheet (182) that is attached to the release liner and covering the notch (150) thereby further reducing the fracture risk. The strengthening sheet (182) is applied onto the surface of the release liner not contacting the skin adhesive layer and the strengthening sheet may cover one or both ends of the pull tabs (70, 137) for fixating the pull tabs to the release liner in case the pull tabs are not contacted using the adhesive spots (166, 167) on the backside of the liner. Alternatively, the strengthening sheet may further enhance the connection (adhesive strength F3) between the release liner and the pull tabs (70,137) if the pull tabs are adhered to the liner using the first and second adhesive spots (166, 167). The strengthening sheet (182) may be attached to the barrier film (99) covering the passage (98) in the needle housing such that the release liner removal simultaneously removes the sterile barrier for the skin needle. Thus during release liner removal at least one sterile barrier film is removed either from the needle unit, and/or from the cartridge unit and/or from the passage for the skin needle. Optionally, two strengthening sheets are used, one covering both pull tabs and the other the sterile barrier for the needle housing. As another option three strengthening sheets are used for each pull tab and the sterile barrier for the needle housing.

As an alternative none of the sterile barriers (64, 136) covering the needle unit and the cartridge unit is removed. In other words, the cartridge needle will penetrate two sterile barriers before piercing the septum. As yet another alternative only one sterile barrier film is removed, for example the sterile barrier film (64) covering the passage in needle unit. During cartridge needle insertion, the cartridge needle will penetrate the sterile barrier (136) still covering the septum of the cartridge. The sterile barriers are connected—or not connected—to the release liner accordingly.

By removing the release liner, all three sterile barrier films that cover the passage for the skin needle, the passage for the cartridge needle and the sterile barrier film covering the septum may be removed from the device, ensuring that both passages of the needle unit and the one passage for the cartridge unit are free.

The release liner (6) and/or the strengthening sheets (182) may be coated with a conductive layer (154) which at least partially shields the sensor areas (161, 162) in the sensor layer (160) of the sensing patch unit (13). Upon removal, the dielectric medium adjacent and/or between the at least two sensor areas (161, 162) changes as the release liner with the shielding layer is removed and the skin adhesive layer or sensors are exposed to the ambient. The change is measured by the capacitive sensors (161, 162) in the sensor layer (160) and signaled to the PCB unit (9) via the contacting springs (29). In principle the change can be measured with one of the two sensors (161,162) only. The tact frequency for the electronic circuit may be low to save energy and once the change is capacity is processed, the tact frequency may be increased. Furthermore, the push button switch (16) may be activated after the liner removal has been determined by the capacitive sensor. Alternatively, the push button switch (16) is activated after attaching the injection device to the skin of the patient. Once attached, the dielectric medium for the sensors (161, 162) in the sensor layer changes again, indicating proper skin attachment of the device. The release liner removal and/or the skin attachment may be notified to the user by the visual LED indicators and/or by audible signals generated by a buzzer, and/or signaled by an external device receiving the information via wireless transmittance.

After the liner removal and the skin attachment, the push button switch (16) of the PCB unit is active and the user may push the button (5) to start the injection sequence. As an alternative, the device does not have a push button (5) and push button switch (16), but starts automatically the injection procedure, for example after a delay time after the sensor patch unit determines that the device is attached to the skin. Safety loops may be included to ensure that the injection is not started too early, for example when the user is still manipulating the device at the injection location. Such as a safety loop may require a stable sensor signal for a minimum amount of time before the injection sequence is started automatically. Alternatively, the injection sequence is started based on an audible signal from the user that is picked up by a microphone connected to the PCB unit. As yet another alternative, the injection device does not have a mechanical push button on the device but a virtual release button is available on a separate device that is wireless connected to the injection device, for example a smart phone. The virtual release button is pressed on the external device and transmitted to the device which starts the injection sequence.

Figure 35:
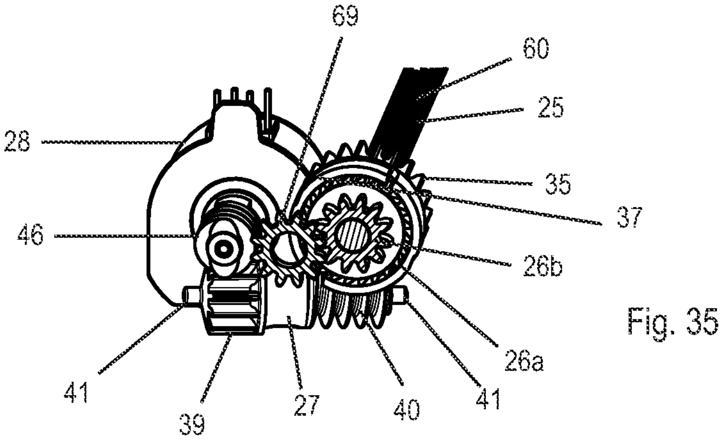
FIG. 35: Detail of the gear mechanism.
Figure 36:
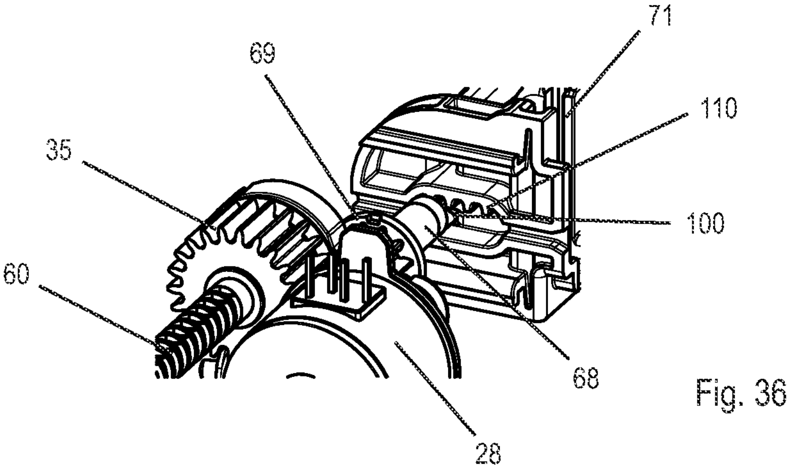
FIG. 36: Detail of the gear mechanism and the electromotor of the drive unit engaging the cam shaft and slider of the needle unit.
Figure 37A:
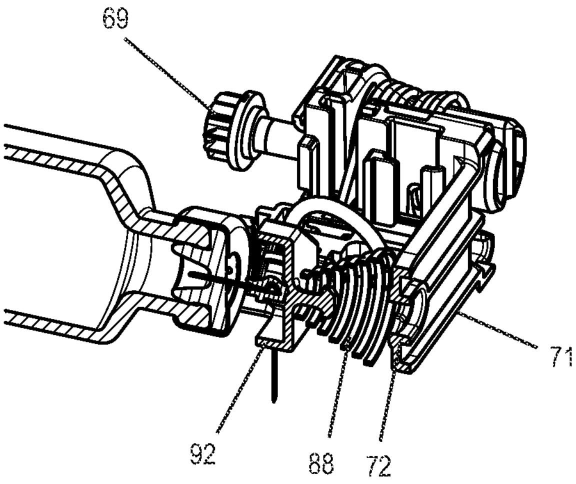
FIGS. 37*a*, 37*b*: Cartridge needle slider driven by the cartridge needle slider spring (all of needle unit) to pierce the septum of the cartridge unit.
Figure 37B:
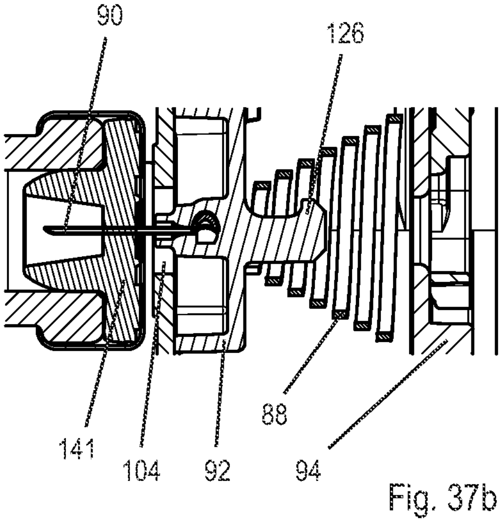

Cartridge needle insertion: When the user pushes the push button, the injection sequence is started or the injection sequence is automatically started if there is no mechanical push button in the device. The stepper motor (28) in the drive unit is controlled by the PCB unit (9) to rotate in a first rotation direction that may be at a first rotational speed optimized for the needle insertion. The rotation of the stepper motor is transferred by gearing (46,39,40,35) into a rotation of the ratchet wheel (26) as the one-way ratchet (37, 26*a*) between the driver (34) and the ratchet wheel (26) forces the latter to co-rotate with the driver (34). The cam shaft (68) rotates as well as the drive teeth (26*b*) of the ratchet wheel (26) engage the gear wheel (69) of the cam shaft, see FIG. 35. The rotation of the cam shaft (68) is transferred from the gear wheel (100) of the cam shaft to the gear rack (75) of the slider (71) located in the needle unit. The slider (71) will move from a starting position to a first intermediate position due to the gear teeth (110) of the gear rack (75) engaging the gear wheel (100) of the cam shaft (68), FIG. 36. The slider is guided by the mechanism holder (94) due to the linear guide formed by the linear keys (73) on the slider and the guide (105) on the mechanism holder. As the slider (71) moves to the first intermediate position, the engagement between the locking fork (72) of the slider and the knob (126) of the cartridge needle slider (92) is released and the cartridge needle slider (92) is moved by the decompressing spring (88) and the cartridge needle (90) pierces the septum (141) of the cartridge unit (FIGS. 37*a* and 37*b*). The movement of the assembly of cartridge needle holder (91) and cartridge needle slider (92) may be accompanied by an acoustic signal and/or visual signal (LED light) and/or tactile feedback to the user. In an alternative which will be described further below, the slider movement will release a lock for an intermediate member which will be subsequently moved by a biasing force. The movement of the intermediate member will release the cartridge needle slider.

Figure 38:
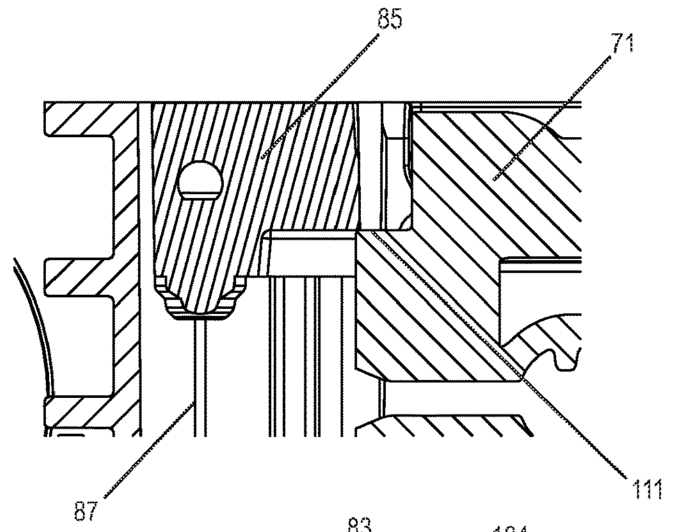
FIG. 38: Skin needle slider abutting the slider for keeping the skin needle in the retracted position.
Figure 39:
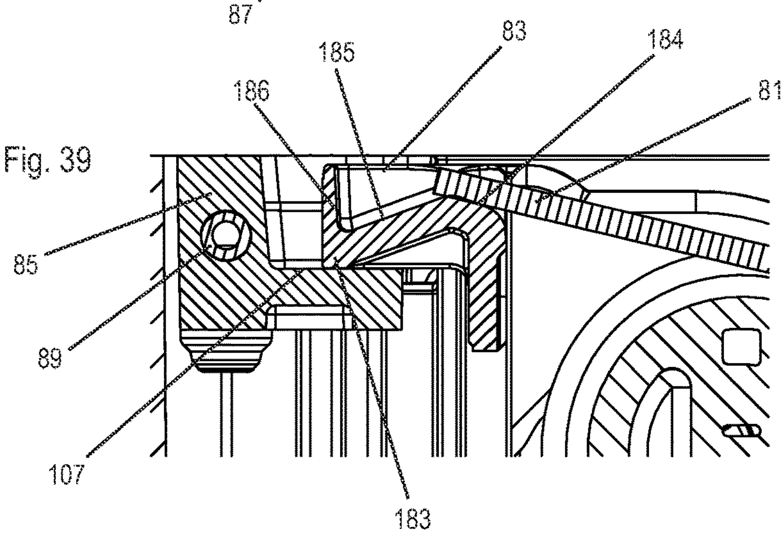
FIG. 39: Upper leg of torsional spring biasing the skin needle holder towards the inserted position via the upper spring slider.
Figure 40:
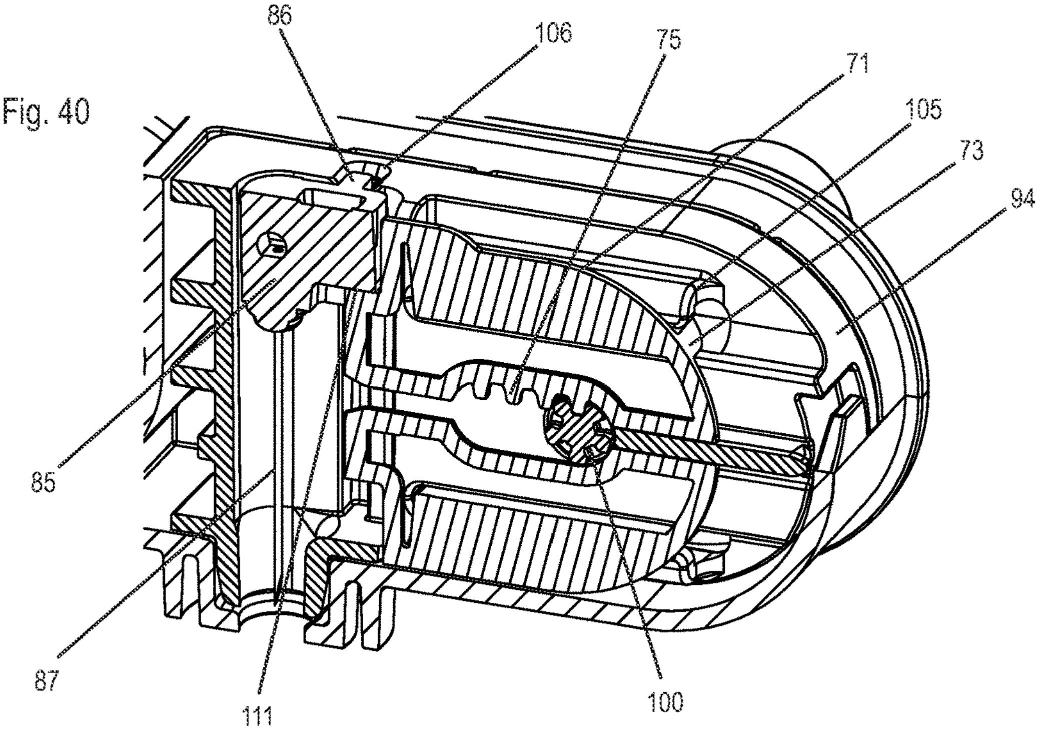
FIG. 40: Cross section of the needle unit with the slider in the starting position.
Figure 41:
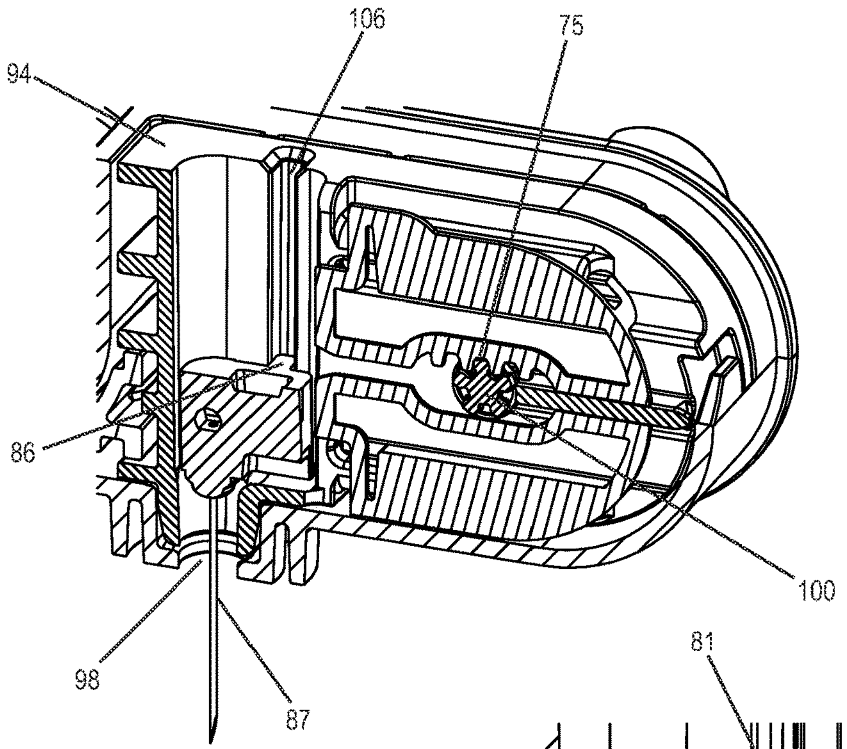
FIG. 41: Cross section of the needle unit with the slider in an intermediate position.
Figure 42:
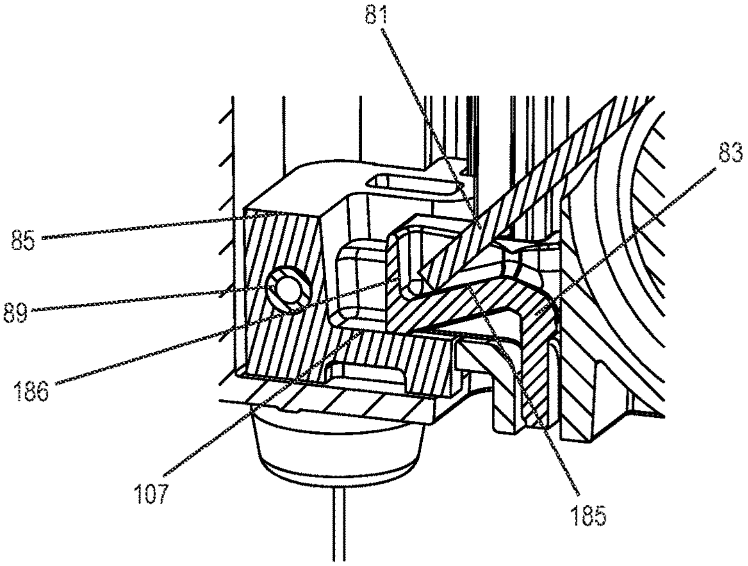
FIG. 42: Leg of torsional has moved the skin needle holder to the inserted position via upper spring slider.

Skin needle insertion: When the slider (71) is in the starting position (FIGS. 39 and 40), then the stop surface (111) of the slider abuts the skin needle holder (85), (FIG. 40) and keeps the skin needle holder in a needle retracted position against the bias of the upper leg (81) of the torsional spring (79) pushing on the skin needle holder (85) via the upper spring slider (83) and the receiving section (107) of the skin needle holder. The upper leg (81) abuts an abutment surface (184) of the upper spring slider which may be a sloped surface. Upon rotation of the cam shaft, the slider (71) moves towards the first intermediate position (FIG. 41) and the engagement between the slider (71) having stop surface (111) to the skin needle holder is released (see FIG. 38). The skin needle holder (85) will move together with the skin needle (87) towards the inserted position and the tip of the skin needle moves through the aperture (98) in the housing unit as the upper leg (81) of the torsional spring (79) pushes on the upper spring slider (83). The skin needle holder (85) is guided with its keys (86) through guides (106) of the mechanism holder (94) to insert the needle (87) perpendicular to the bottom surface of the injection device. In FIG. 42, the skin needle holder is in the needle inserted position and the conduit (89) can be observed in the cross sectional view. The cartridge needle has been inserted first in this example followed by the insertion of the skin needle thereby establishing a fluid contact between the patient and the medicament present in the cartridge unit. The situation may also be reversed, e.g. that first the skin needle (87) is inserted followed by the insertion of the cartridge needle (90). The insertion step may also comprise two intermediate positions for the slider (7) a first intermediate position where the cartridge needle is inserted and a second intermediate position where the kin needle is inserted. Alternatively there may be a continuous movement from the starting position to the first intermediate position while to two needles are inserted subsequently.

When the skin needle (87) is in the inserted position then there is an anti-shift back feature for the skin needle holder (85), FIG. 42. In the needle inserted position, the end of the upper leg (81) contacts a sloped surface (185) of the upper spring slider (83). When the upper spring slider (83) contacts the skin needle holder (85) via the receiving section (107) then a return movement of the holder will be stopped as the end of the upper leg (81) will abut end surface (186) of the upper skin slider (83). During a return movement, the sloped surface (185) will guide the end of the upper leg into abutment with the end surface (186) of the upper skin slider thereby blocking the upward movement of the skin needle holder (85).

Figure 47:
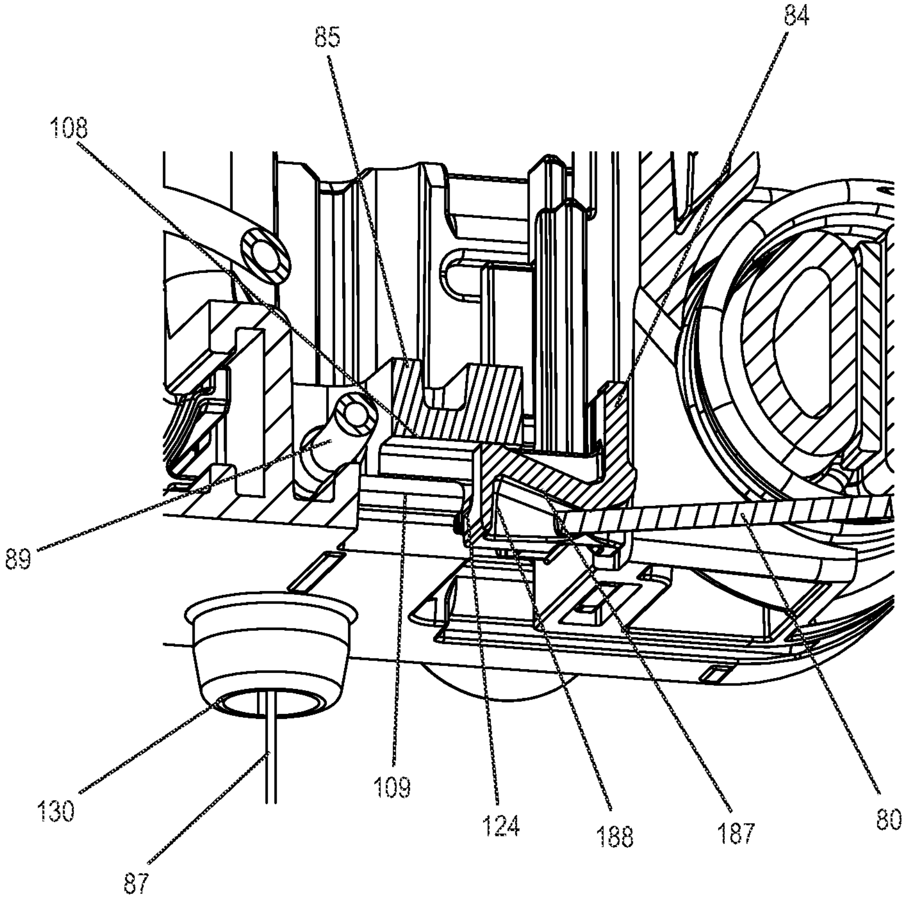
FIG. 47: Lower leg of spring biasing the lower spring slider towards the retracted position, locking member prevents movement of the lower spring slider towards the retracted position.

The movement of the skin needle holder (85) in the needle inserted direction is stopped when the skin needle holder (85) abuts a wall or stop surface that is present on the housing of the needle unit. The skin needle holder (85) may engage, for example, abuts in the inserted position the lower spring slider (84). The lower spring slider (84) may but the receiving section (108) on the skin needle holder (85), see FIG. 47. The lower spring slider (84) is kept in the needle inserted position under the bias of the lower leg (80) of the torsional spring (79) which intends to move the lower spring slider from the inserted position to the retracted position. The lower spring slider (84) is kept in the inserted position (FIG. 47) as the holding surface (124) of the lower spring slider engages the locking member (109) on the mechanism holder. The engagement between the holding surface (124) and the locking member (109) is such that the lower skin slider (84) may axially move together with the slider (71).

During assembly of the device, the upper spring slider (83) is in the needle retracted position and biased by the upper leg (81) towards the needle inserted position and this movement is blocked by the skin needle holder (85) engaging the slider (71). When the upper spring slider is in the needle retracted position, then the lower spring slider (84) is in the needle inserted position and not in abutment with the skin needle holder (85) yet. The lower spring needle slider (84) is kept in the inserted position due the engagement (109, 124) of the slider with the mechanism holder.

Figure 43:
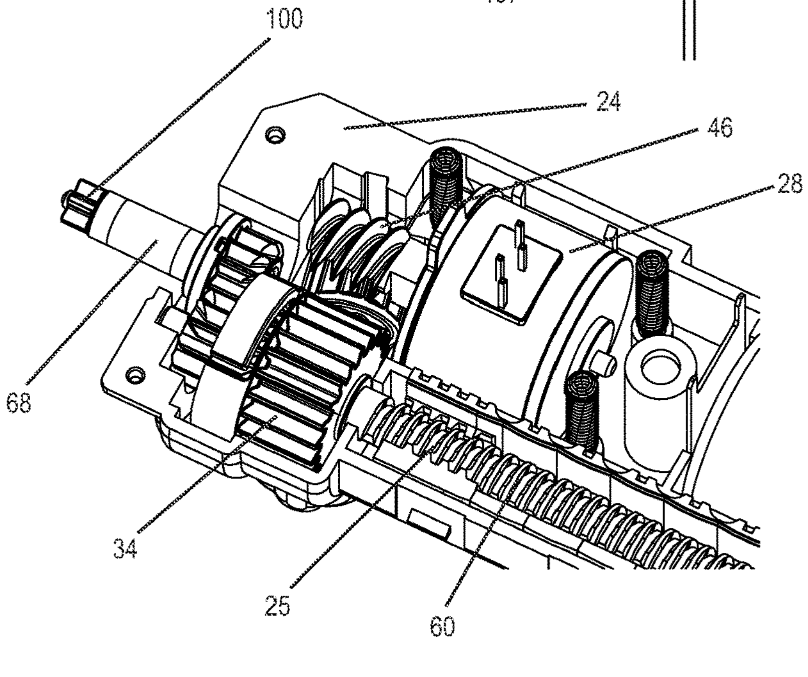
FIG. 43: Gear mechanism driving the threaded rod for piston rod advancement.

Dose delivery: The slider (71) is moved to an intermediate position for needle insertion and that position is defined by the number of revolutions (or steps) of the stepper motor in the first rotation direction and therewith the number of revolutions of the cam shaft (68) for sliding the slider (71). After a certain number of revolutions in one rotation direction, the rotation in that direction is stopped. Alternatively a separate sensor that is not shown measures the position of the slider and forwards the information to the PCB unit. After the insertion of both needles, the rotation direction of the stepper motor (28) is reversed. The threaded rod (25) comprising the driver (34) will be rotated in the opposite direction and the rotation of the driver (34) is not transmitted to the ratchet wheel (25) as the torque that is transmitted from the ratchet arms (37) of the driver (34) to the asymmetric ratchet teeth (26*a*) of the ratchet wheel (26) is below the friction between of the cam-shaft (68) and the housing as, for example, generated by the O-ring (102*a*) or to a lesser extent by the V-ring. Alternatively, there may be a tight press-fit between the cam shaft and the housing forming a sterile barrier. The ratchet wheel (26) will not rotate and the ratchet member (37) at the end of the flexible arms (38) will ratchet over the ratchet teeth (26*a*) of the ratchet wheel thereby generating audible clicks during dose delivery (FIG. 43).

The rotation of the driver (34) will rotate the threaded rod (25) and the piston rod (31) will advance due to the threaded engagement (54, 60) between the threaded rod (25) and the first segment (53) of the piston rod (31). The segmented piston rod is prevented from rotation around its own axis and will slide through the guides (59) during advancement thereby going through a U-shaped configuration. The last segment of the piston rod (49) either abuts the plunger (140) in the cartridge or abuts the spacer (142) abutting the plunger to expel medication through the cartridge needle, the conduit and the skin needle into the patient. The driver (34) is permanently rotationally coupled to the threaded rod (25) independent from the rotation direction that is transmitted from the stepper motor via the gear mechanism. This implies that during the needle insertion step the segmented piston rod may retract as the slider is moved from the first position to the intermediate position. The spacer may comprise a resilient element for keeping the pivot bearing between the last segment and the spacer in engagement during the piston rod retraction.

Figure 44:
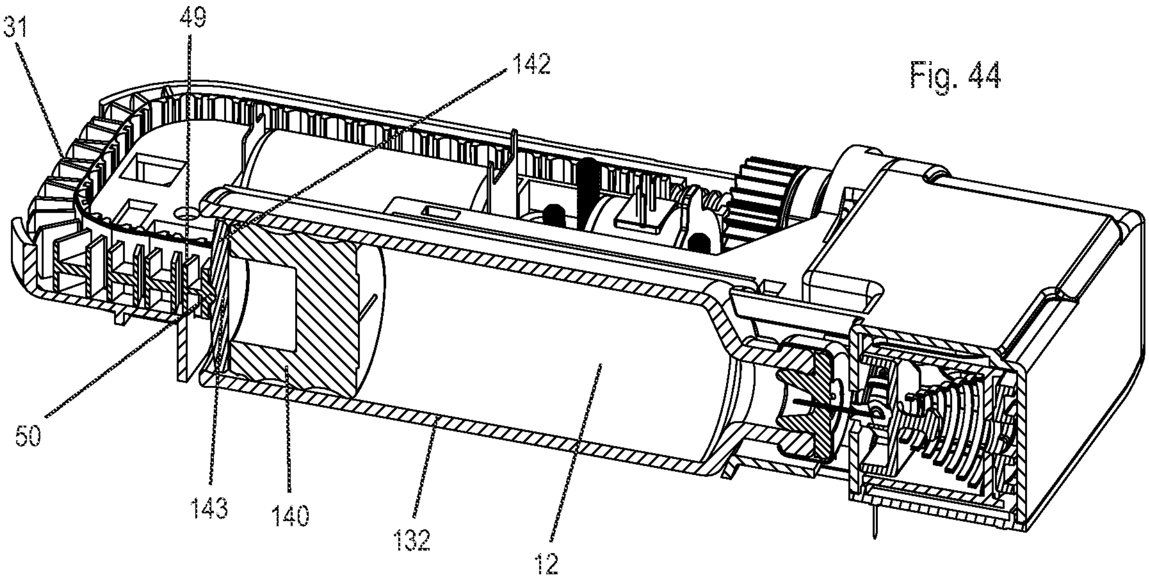
FIG. 44: Drive unit and needle unit, piston rod in retracted position with a full cartridge.
Figure 45:
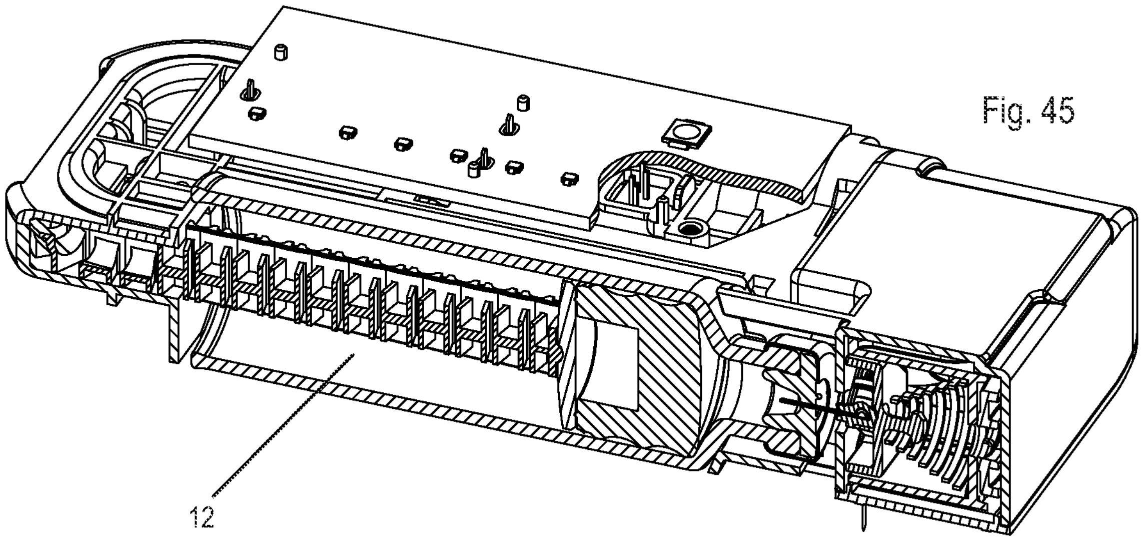
FIG. 45: Drive unit and needle unit, piston rod in extended position, cartridge empty.

The piston rod advancement is shown in FIGS. 44 and 45, where the piston rod (31) advances the plunger (140) in the barrel (132) of the cartridge unit. The last segment (49) of the piston rod comprises the protrusion (50) that engages a bearing surface (143) of the spacer (142). The pivot bearing that is established may be a ball-in-a-socket, or a ball-on-plate bearing ensuring that any off-axis loading by the piston rod entering the cartridge is compensated and that the plunger is not subjected to any tilting moment. When the plunger (140) has reached the end of the barrel and enters the neck section (FIG. 45) then the piston rod advancement is stopped. The plunger (140) may be covered by the frame surrounding the viewing window in the cover of the housing unit (8) when the piston rod has reached its final position.

As an alternative and not desired option, the plunger may stop in a position that is between the positions shown in FIGS. 44 and 45, due to an occlusion in the fluid path preventing further advancement of the plunger. The PCB unit may have several sensors for determining that the cartridge has been emptied or that there is an occlusion. The electromotor may have an encoder measuring the rotation or steps of the electromotor and a separate sensor (for example a photo sensor, or a sliding contact) following the rotation of the gear mechanism and a control module in the PCB unit measures any differences in rotation between the two for determining an empty cartridge or an occlusion. This set-up requires separate sensor units. Alternatively, the current is measured to energize the electromotor and used as a signal for the load delivered by the motor. The current signal needs to be processed by the control module for detecting a blocking of the piston rod advancement, which requires additional features in the PCB unit. In another arrangement, the Back Electro Motive Force (BEMF) is measured where the electromotor is operated as a generator for a limited period of time during a cycle and the resultant voltage is measured before the electromotor is switched back to motor operation. The back-EMF signal is measured and analyzed for counting the number of revolutions within the electromotor. This option has the advantage that it does not require any additional components. Finally, the extra load on the electromotor due to blockage of the piston rod advancement can be measured as a phase shift or step-loss due to an axial displacement of the rotor versus the stator in the electromotor and this may be used for determining an empty cartridge or an occlusion.

The control system in the PCB unit may activate optical (LED) or acoustic (buzzer) or tactile (vibrating signals to the user when the cartridge has been emptied or when the there is an occlusion in the fluid path preventing further piston rod advancement.

Figure 46:
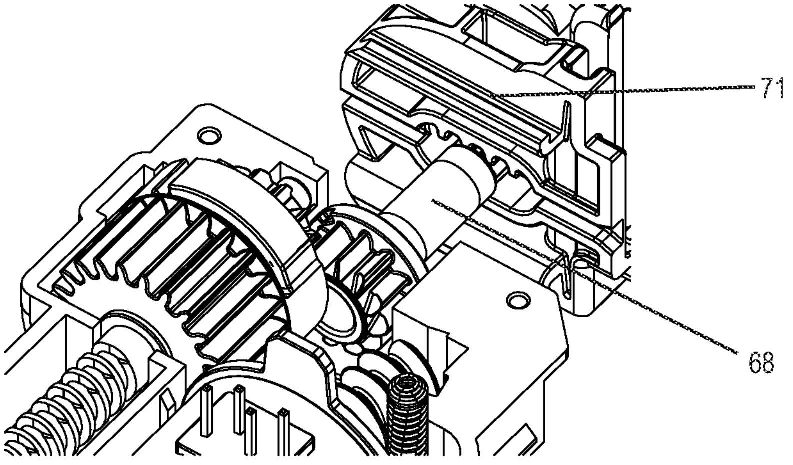
FIG. 46: Gear mechanism and slider in an intermediate position.
Figure 48:
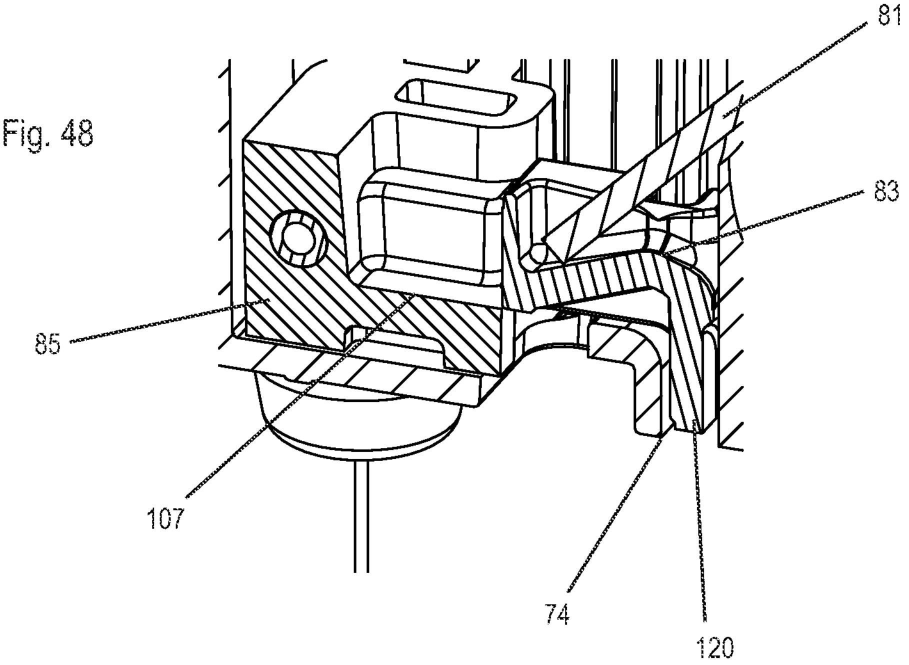
FIG. 48: Upper spring slider released from the skin needle holder.
Figure 49:
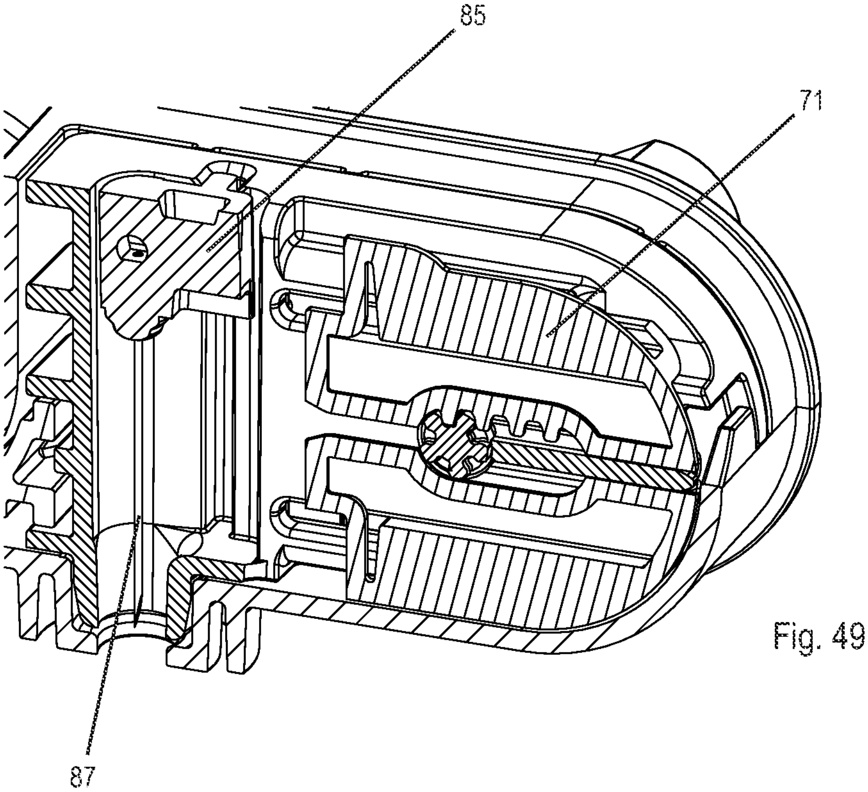
FIG. 49: Cross section of needle unit with slider in final position and skin needle holder in retracted position.
Figure 50:
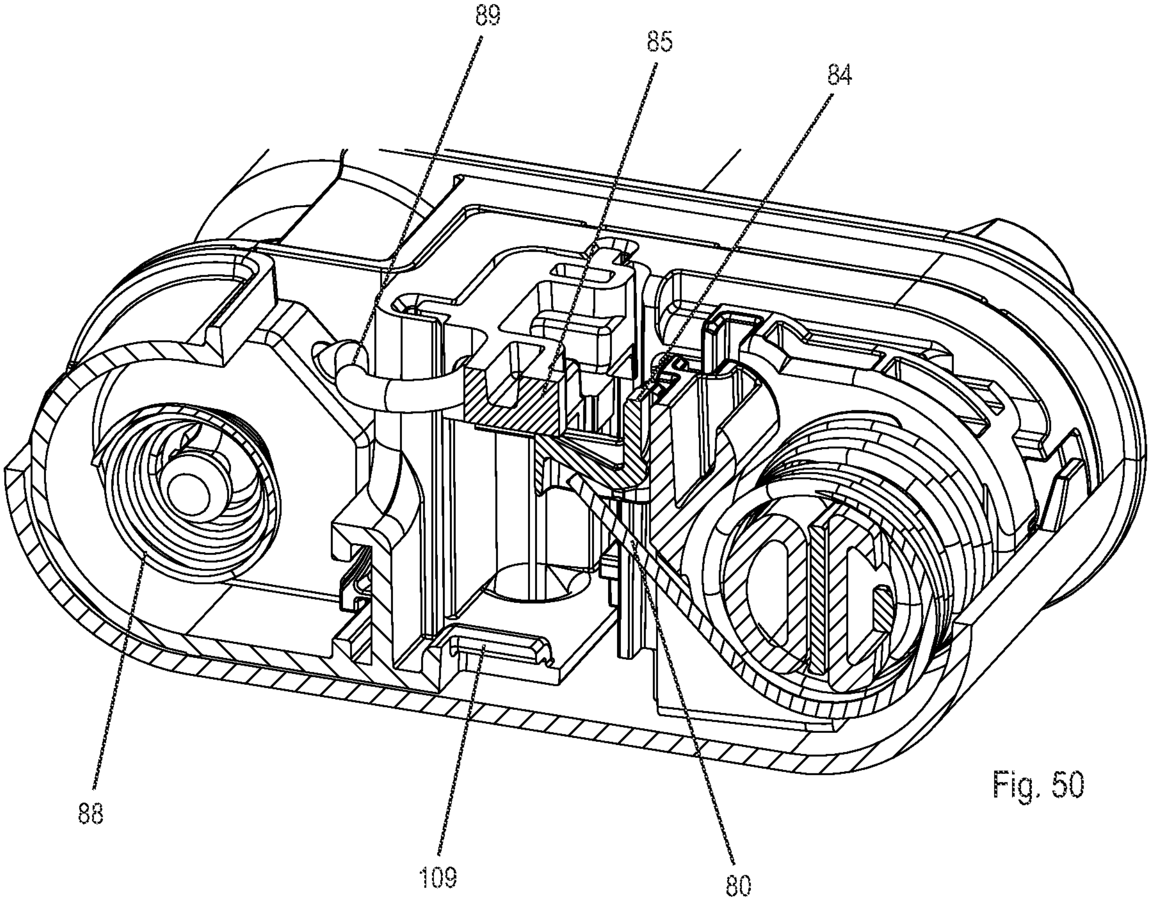
FIG. 50: Injection device with retracted needle.

Retraction of the skin needle: When the plunger has advanced to the end of the cartridge, a signal from a sensor, an encoder or the electromotor is received in the control/PCB unit signaling blockage of the piston rod as there are no further revolutions within the electromotor. If the number of revolutions equals or is above the target value then the PCB unit controlling the electromotor will reverse the rotation direction from the second rotation (for delivery) back to the first rotation direction that was also used for the needle insertion step once a predefined number of revolutions has been reached. The predefined number of revolutions corresponds to the final piston rod position, e.g. once the cartridge has been completely emptied. If the number of predefined number of revolutions has not been reached, then the plunger (and piston rod) may not have advanced to the final position which may be an indication of an occlusion or malfunctioning in the device. Also in this case the needle may be retracted but an error message may be provided to the user via the LEDs or via an external device. Reversal of the rotation direction, either for the empty cartridge or during an occlusion will have the following effect. The gear mechanism will rotate the driver (34) and the ratchet wheel (26) as the one way ratchet system is rotationally locked. As a result, the slider (71) will move from the first intermediate position to a next position (FIG. 46). The next position may be the final position or a subsequent intermediate position before moving to the final position. The slider may move from a first intermediate position without any additional stops to the final position. The movement of the slider (71) results in a lateral movement of the upper spring slider (83) and the lower spring slider (84) as the two spring sliders are engaged via the linear guides (74) to the slider (71), see FIGS. **8*l* and 8*r*. The skin needle holder (85) is engaged with the mechanism holder (94) resulting in a relative axial movement between the skin needle sliders (83,84) and the skin needle holder (85) as the slider (71) moves towards the final position. The engagement between the upper spring slider (83) and the engagement section (107) of the skin needle holder (85) may be released first (FIG. 48). The biasing force of the upper leg (81) may move the upper spring slider in a final position, for example in abutment with the mechanism holder and simultaneously the skin needle holder (85) is free to move back into the retracted position. In a subsequent step, while the slider is moving towards the final position, the engagement between the lower spring slider (84) and the mechanism holder (109, 84—FIG. 47) is released and the lower spring slider (84) moves towards the retracted position as the slider is guided by linear guides (74) of the slider due to the torque that is released from the torsional spring and applied to the lower spring slider via the lower leg (80). The lower spring slider (84) engages receiving section (108) of the skin needle holder and therefore the skin needle holder (85) including the needle (87) is moved back to the retracted position as the skin needle holder is guided in the mechanism holder (FIG. 49, FIG. 50). The lower skin slider has an end surface preventing movement back to the inserted position as the end of the lower leg (80) will abut the end surface of the lower skin slider. This mechanism equals the mechanism for preventing the movement the skin needle holder from the inserted to the retracted position using end surface (188**) for the upper spring slider, see above.

As an alternative, first the lower spring slider is released from the mechanism holder followed by the release of the upper spring slider from the skin needle holder.

As the slider (71) has reached the final position (FIG. 49), the sensor system described above will signal blocking of the gearing mechanism and this signal may be used by the PCB unit to provide and acoustic, visual or tactile signal to the user that the skin needle has been retracted. The PCB unit may apply a holding time, for example 60 seconds, more preferably 30 seconds, even more preferably between 5 and 10 seconds during (or after) which a signal is provided to the user before the user may remove the device from the skin. The holding time enhances the diffusion of the medicament into the (subcutaneous) tissue before removing the device from the skin. The end of injection signal may be directly sent to the user by the device and/or may be sent via a wireless connection (such as Bluetooth) to an external device which provides the end of injection signal.

Optionally, after the holding time or after a time substantially longer than the holding time (e.g., more than 5 minutes), the rotation direction of the electromotor may be reversed again thus attempting to further advance the piston rod in the cartridge. The piston rod is already in the most forefront position and the additional force executed on the piston rod will compress, damage or even fracture the segmented piston rod thereby preventing re-use of a device intended for single-use only. The feature may be linked to the piston rod position, e.g. for an emptied cartridge the control unit may allow for a further reversal of the rotation direction for damaging the piston rod. A piston rod (intermediate) position reached after an occlusion occurred or after a warning signal has been issued and thus not corresponding to the emptied cartridge may not be subject to the feature of a further reversal of the rotation direction of the electromotor to prevent excessive pressure in the (non-empty/partially filled) cartridge.

The signals provided by the sensors and/or the electromotor related to the needle insertion, piston rod advancement to the final position, occlusion in the fluid path unit or needle retraction may be used for the visual, tactile or audible signaling directly to the user. Optionally, the signals are sent to an external device, for example a smart phone and the smart phone provides for the visual, tactile or audible signals. Thus there may be a system were the injection device provide signals to the user, or that one of the device or the external device (smart phone) provides for the signals. The PCB unit may signal an alarm to the user upon malfunctioning of the device such as the occurrence of partial removal of the device as measured by the sensor unit, an occlusion in the fluid path, motor failure, low battery power, failure of the push button switch, failure to insert the cartridge needle into the cartridge unit, failure to insert the skin needle or failure to retract the skin needle. Such a signal may be followed by additional steps in the injection sequence, for example when the sensors in the sensor layer of the sensor patch unit measure partial removal of the device or when an occlusion occurs, then the processor may activate the needle retraction step (by reversing the rotation direction of the motor) before the cartridge has been emptied.

Signals may also be received from an external device to the PCB unit via a wireless communication such that the start of the injection may be triggered by an external device.

The PCB unit may be capable of receiving vocal instructions from the user, for example using a voice recognition tool. Alternatively, the PCB unit may provide vocal instructions using a speaker for giving instructions to the user.

The injection device is intended to be used in combination with a wide variety of medicaments each having a specific dosing volume and/or viscosity of the liquid and which require a certain injection time. The injection device may be configured to receive glass cartridges with a nominal volume between 2 mL and 20 mL, preferably between 5 and 10 mL. Smaller cartridges may use the cartridge holder that is designed for the larger cartridges using a volume adapter that compensates for the space between the smaller cartridge and the cartridge holder. The injection time may be below 30 minutes, more preferably below 10 minutes and most preferably less than 1 minute. The gear ratios of the gearing mechanism between the electromotor and the cam shaft may be adapted to accommodate different viscosities of the medicament in the cartridge unit and/or different needle gauges for the skin needle, respectively the cartridge needle used which may increase the force required to advance the piston rod.

Figure 51:
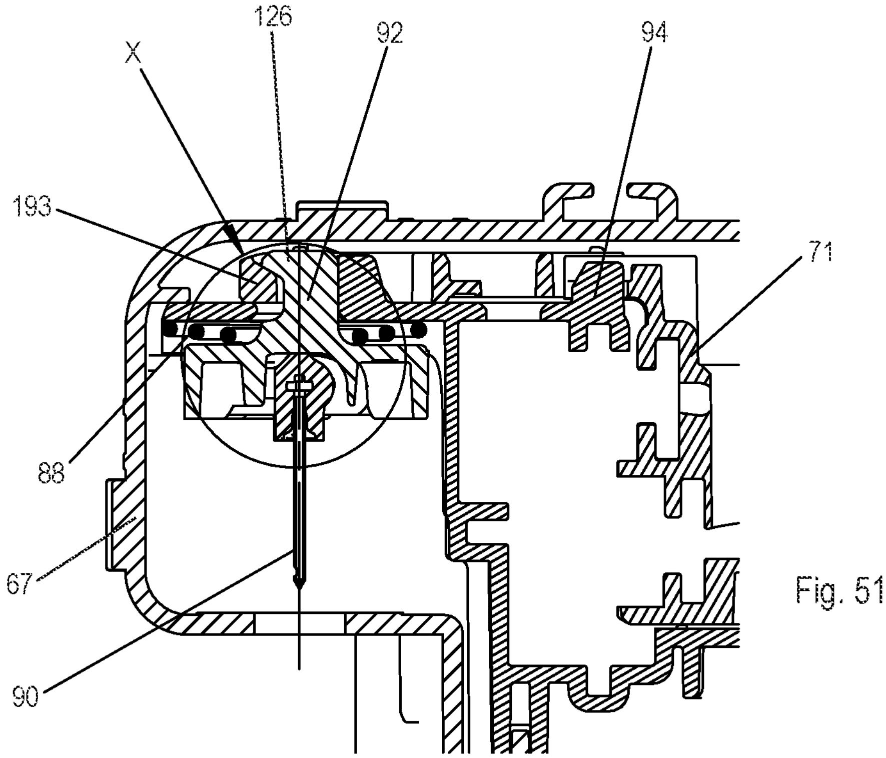
FIG. 51: Cross sectional view: Cartridge needle insertion mechanism with slider and slider release latch. Slider is in the first position keeping the lock between the slider release latch and the slider locked. The slider release latch is in the blocked position.
Figure 51A:
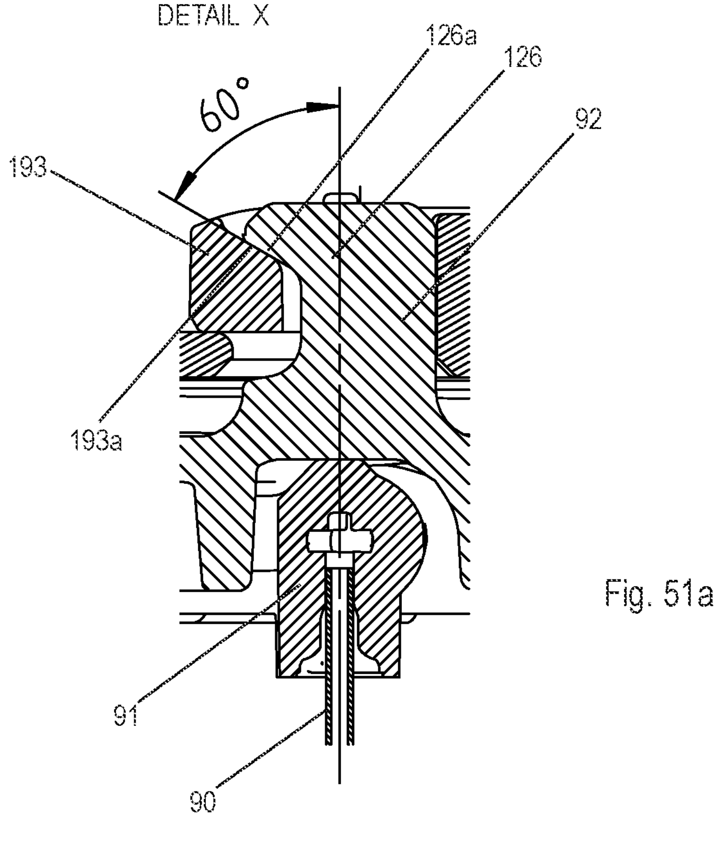
FIG. 51*a*: Detail of the needle holder (or cartridge needle slider) and gearing between the needle holder and the slider release latch.
Figure 52:
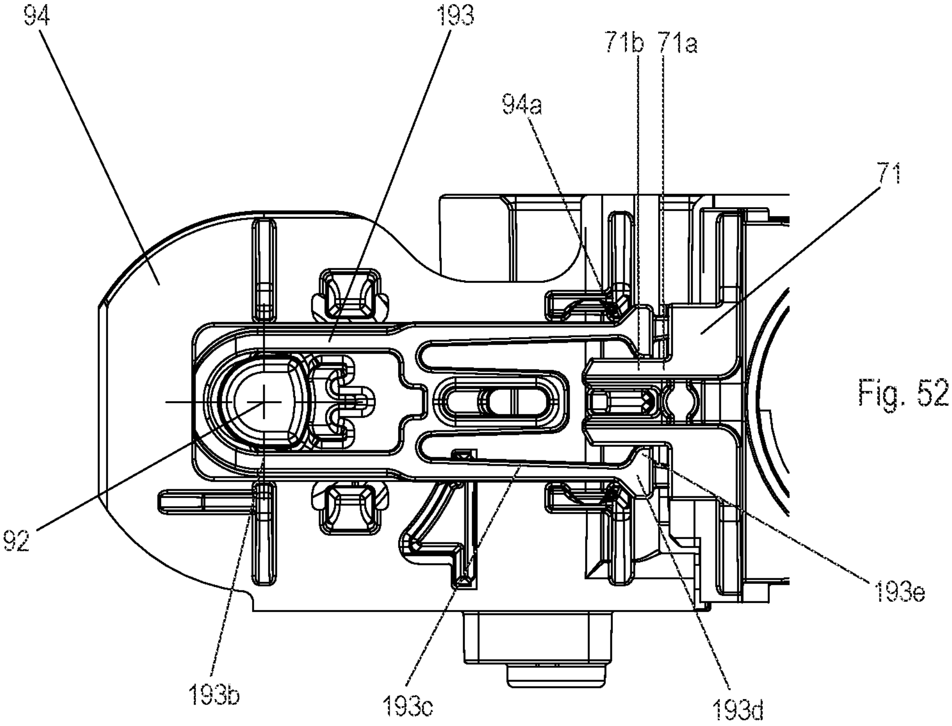
FIG. 52: Top view: Cartridge needle insertion mechanism with slider and slider release latch. Slider is in the first position keeping the lock between the slider release latch and the slider in the blocked position.

Another embodiment for the cartridge needle insertion mechanism is presented in FIGS. 51 to 55. In the embodiment described above and shown in more detail in FIG. 11, the slider (71) directly releases the cartridge needle slider (92) as the slider (71) is moved to the second position. The force of the spring presses the slider (71) towards the mechanism holder (94) which may increase the frictional force that needs to be overcome for moving the slider (71). In the embodiment in FIGS. 51 and 52, the slider (71) is shown in the first position and a separate slider release latch (SRL) (193) or so-called intermediate member is positioned between the slider (71) and the cartridge needle slider (92) comprising the needle holder (91) holding the cartridge needle (90). The slider release latch (193) is guided by the mechanism holder (94) for movement perpendicular to the needle axis of cartridge needle (90). The cartridge needle slider (92) has the knob (126) engaging the slider release latch (193). The slider release latch (193) comprises a gearing surface (193*a*) and the cartridge needle slider (92) comprises a complementary gearing surface (126*a*). The two gearing surfaces form a gearing (193*a*, 126*a*), see for details FIG. 51*a*. The gearing surfaces are oriented in this example at an angle of 60 degrees with respect to the needle axis. Other angles above or below 60 degrees are also an option, for example 40, 50, 70 0r 80 degrees. The spring (88) is positioned between the mechanism holder (94) and a flange on the cartridge needle slider (92) and the spring (88) biases the cartridge needle slider (92) for movement towards the inserted position. The force of the spring (88) also biases the slider release latch (193) via the gearing (193*a*, 126*a*) for movement perpendicular to the needle axis and opposite to the movement of the slider (71). The gearing (193*a*, 126*a*) may therefore also be called a biased gearing as the bias of the spring force permanently acts on the gearing surface (126*a*) of the cartridge needle slider (92) pushing on the complementary gearing surface (193*a*) of the slider release latch (193). In the previous embodiment (FIG. 11), the locking fork is directly connected to the slider and in the current embodiment, the so called locking fork is part of the slider release latch (193) and adjacent to an opening (193*b*) in the slider release latch (193). The Knob (126) can pass through the opening (193*b*) when the cartridge needle (90) is inserted. The cartridge needle slider (92) is guided in the mechanism holder (94) and prevented from movement perpendicular to the needle axis. The slider release latch (193) is prevented from movement by a lock (71*a*, 193*d*, 94*a*) whereby a part of the slider release latch (193) is located between the mechanism holder (94) and the slider (71) such that there is a form fit engagement preventing the slider release latch (193) from movement from a blocked position to a release position. The lock comprises an enlarged head or blocking member (193*d*) located at the end of a flexible arm (193*c*) of the slider release latch (193) engaging a protrusion (94*a*) on the mechanism holder (94) and an extension (71*a*) of the slider (71). The enlarged head (193*d*) is in a form-fit engagement with an abutment surface (71*b*) on the slider (71) and an abutment surface (94*b*) on the protrusion such that the slider release latch (193) cannot move towards the release position albeit biased by the biased gearing for movement into that position.

Figure 53:
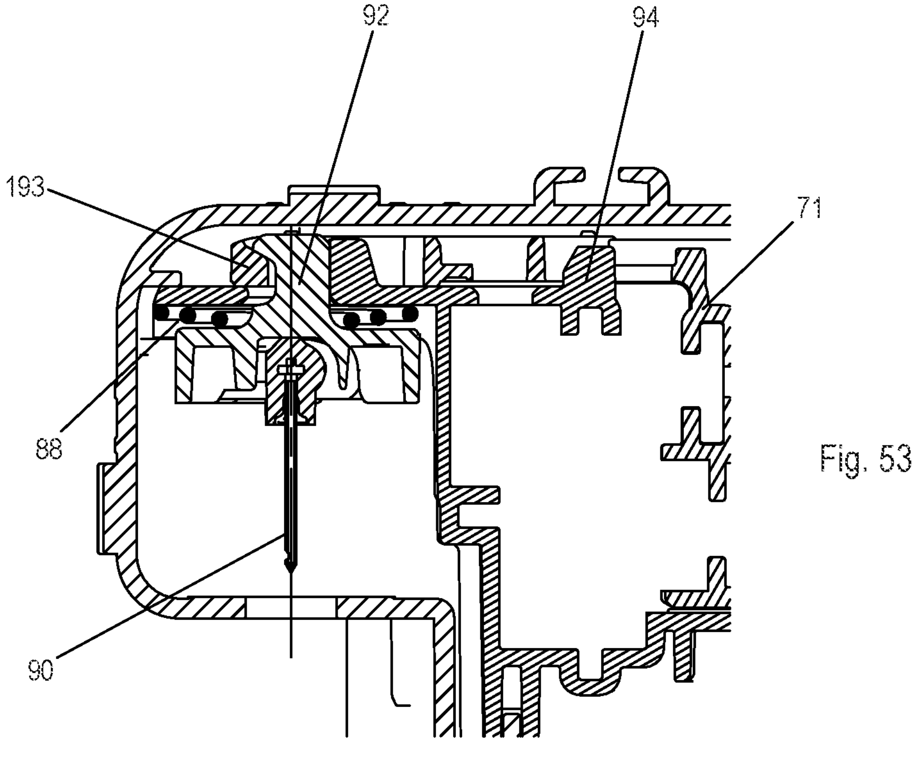
FIG. 53: Cross sectional view: Cartridge needle insertion mechanism with slider and slider release latch. Slider moves towards second position.
Figure 54:
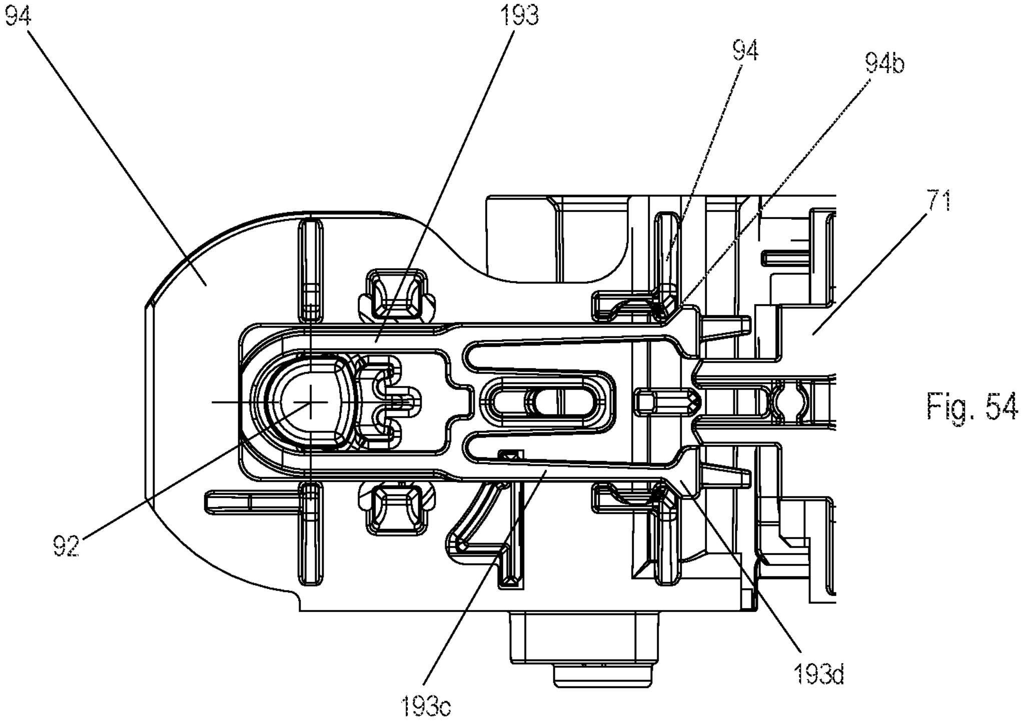
FIG. 54: Top view: Cartridge needle insertion mechanism with slider and slider release latch. Slider moves towards second position whereas the slider release latch moves towards the release position.
Figure 55:
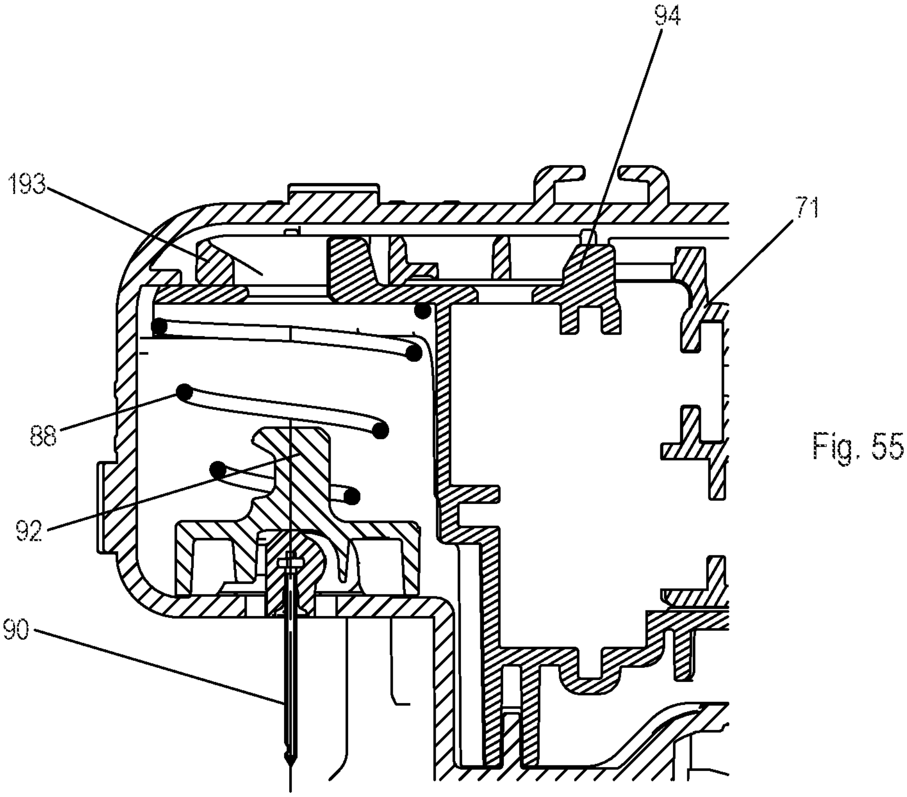
FIG. 55: Cross sectional view: Cartridge needle insertion mechanism with slider and slider release member. Slider is in the second position and the lock between the slider and the release member is unlocked. The biased gearing has moved the slider release latch to the release position for insertion of the cartridge needle.
Figure 56:
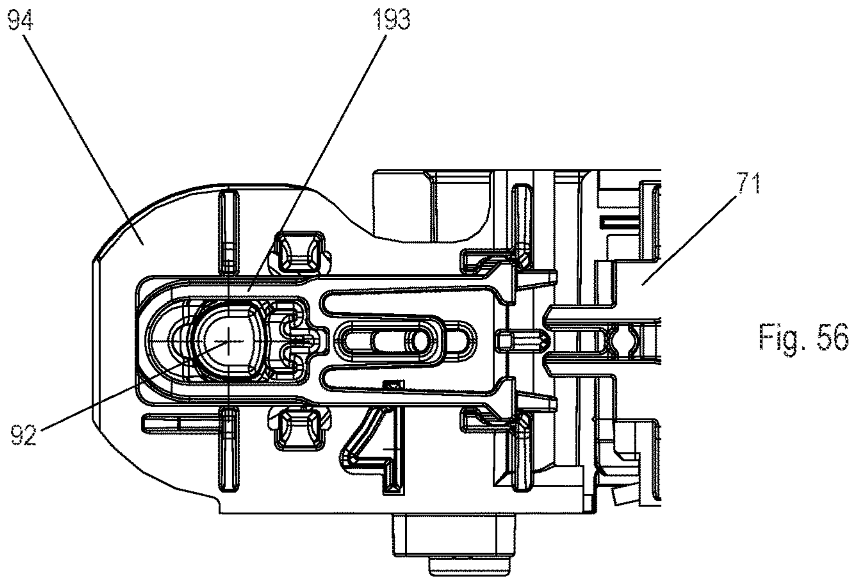
FIG. 56: Top view: Cartridge needle insertion mechanism with slider and slider release latch. Slider is in the second position and the lock between the slider and the release latch is unlocked.

Movement of the slider (71) by rotation of the cam shaft of the rack and pinion arrangement described above will move the slider (71) from the first position towards the second position (FIGS. 53 and 54). The abutment between the enlarged head (193*d*) and the slider (71*b*) is released (FIGS. 54 and 55) and the biased gearing will flex the flexible arms (193*c*) such that the enlarged head (193*d*) passes the protrusion (94*b*) on the mechanism holder. The slider release latch (193) is free to move towards the release position such that the engagement between the knob (126) and the cartridge needle slider (92) is released and the cartridge needle slider (92) is free to move into the inserted position (FIG. 56)

The slider (71) and the slider release latch (193) each move in opposite directions and the bias of the spring force together with the gearing surfaces facilitate the movement of the slider release latch (193) without requiring power from the drive train. The rack- and pinion-engagement between the cam shaft (68) and the gear rack of the slider (71) can be designed for movement of the slider (71) which, in contrast to the previous embodiment, is not biased towards or pressed onto the mechanism holder (94).

Figure 57A:
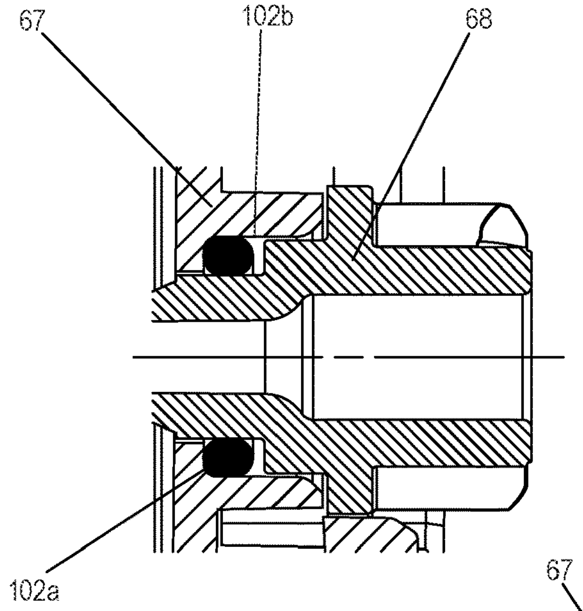
FIGS. 57*a*, 57*b*: Sealing between cam-shaft and needle housing using an O-ring or V-ring.
Figure 57B:
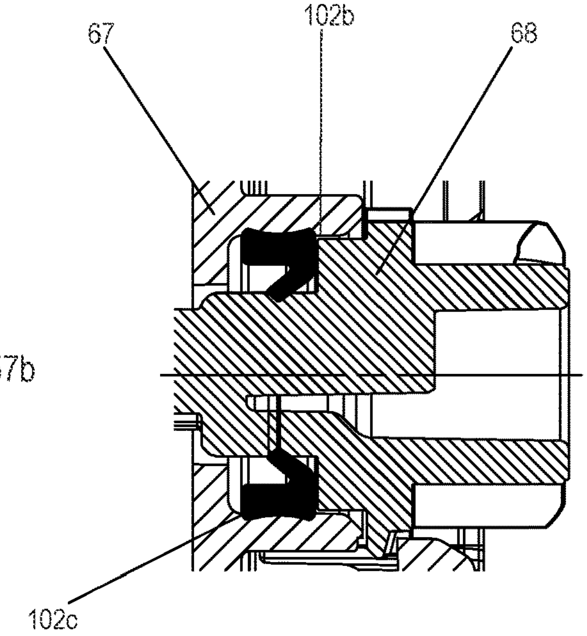

The engagement between the cam shaft (68) and the needle housing (67) is shown in FIGS. 57*a* and 57*b*. An O-ring or a so called V-ring may be present between the cam shaft (68) and the needle housing (67) providing a fluid tight seal or a sterile barrier for the needle housing (67). The sealing element are positioned in the passage (102*b*) for the cam shaft (68).

Figure 58A:
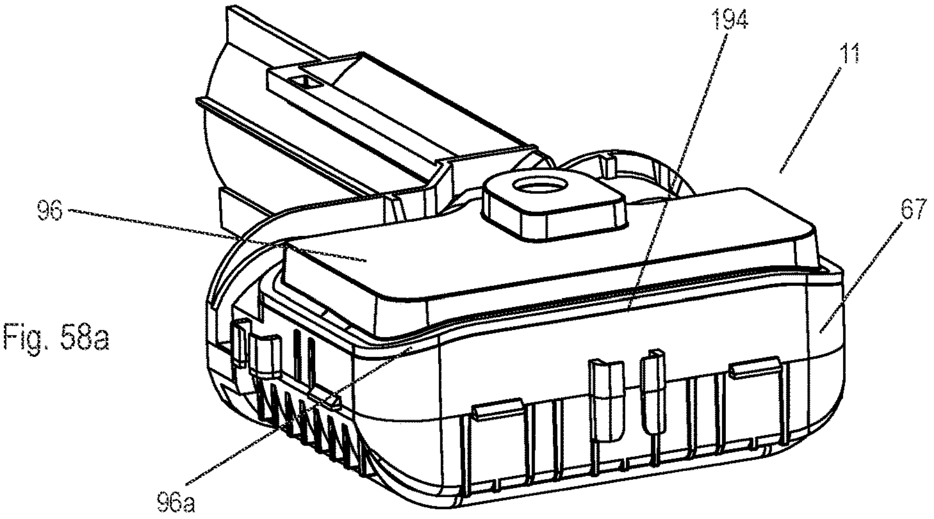
FIGS. 58*a*, 58*b*: Needle unit with flat needle cover and flat welding seam or with a needle cover having angulated winglets.
Figure 58B:
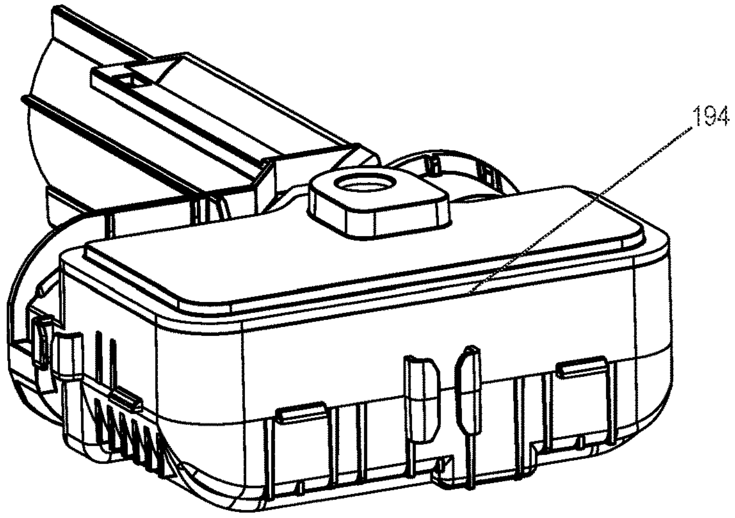

Alternatives for the needle housing (67) of the needle unit (11) are presented in FIGS. 58*a* and 58*b*, respectively. The opening in the needle unit is closed by a needle cover (96) attached to the needle housing (67) by a welding seam (194). The needle cover (96) may have angulated winglets (96*a*) to accommodate the needle unit in an oval shaped outer needle housing (67). Alternatively, no winglets are used (FIG. 58*b*) having the advantage that a laser welded seam is always parallel to the bottom surface which may have advantages during production (single focus for the laser beam in case laser welding is used).

Figure 59:
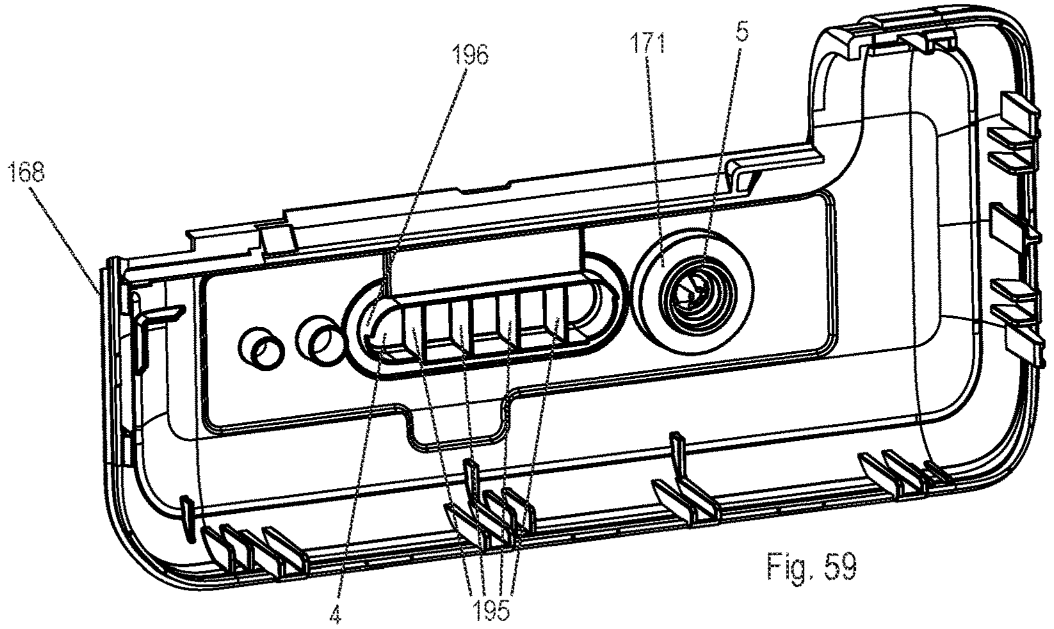
FIG. 59: Housing cover having compartments for receiving LED lights. The compartments are separated by partition walls.

An alternative for the housing cover (168) is shown in FIG. 59. The housing cover (168) is illuminated from the back by LED lights (17) to create the indicator (4), see FIG. 33. In FIG. 33, the laser lights are not separated from each other which may lead to a blurring effect for the user viewing the LEDs through the translucent part (4) in the housing cover. In FIG. 59, each LED is surrounded by its own compartment formed by a shielding wall (196) and partitioning walls (195) between the LEDs. This is beneficial for obtaining clear and sharp edged indicator signs for the user.

| PART ANNOTATION | |
|---|---|
| 1 | Injection device |
| 2 | Housing unit HU |
| 3 | Viewing window cover |
| 4 | Indicator |
| 5 | Push button |
| 6 | Release liner sensing patch unit |
| 7 | Gripping area |
| 8 | Cover HU |
| 9 | Printed circuit board unit PCB |
| 10 | Drive unit DU |
| 11 | Needle unit NU |
| 12 | Cartridge unit CU |
| 13 | Sensing patch unit SU |
| 14 | Top surface PCB |
| 15 | Bottom surface PCB |
| 16 | Push button switch |
| 17 | LED indicators |
| 18 | Positioning apertures PCB |
| 19 | Contacts for contact springs |
| 20 | Contacts to stepper motor |
| 21 | Contacts to battery |
| 22 | Protrusions drive unit |
| 23 | Drive cover DC |
| 24 | Drive carrier DR |
| 25 | Threaded rod TR |
| 26 | Ratchet wheel RW |
| 26a | Ratchet teeth ratchet wheel |
| 26b | Drive teeth ratchet wheel |
| 27 | Gear shaft GS |
| 28 | Stepper motor SR |
| 29 | Contact springs CS |
| 30 | Battery BY |
| 31 | Piston rod PR |
| 32 | Cylindrical aperture |
| 33 | Snapper |
| 34 | Threaded rod driver |
| 35 | Gear teeth threaded rod driver |
| 36 | Shaft end |
| 37 | Ratchet member |
| 38 | Flexible arm |
| 39 | Gear wheel gear shaft |
| 40 | Worm wheel gear shaft |
| 41 | Shaft ends |
| 42 | Motor |
| 43 | Edge end plate |
| 44 | End plate |
| 45 | Contacts |
| 46 | Worm wheel stepper motor |
| 47 | Handle end plate |
| 48 | Segment piston rod |
| 49 | Last segment piston rod |
| 50 | Protrusion last segment |
| 51 | Guiding fin |
| 52 | Hinge piston rod |
| 53 | First segment piston rod |
| 54 | Internal threading |
| 55 | Segment guide |
| 56 | Cylindrical aperture drive carrier |
| 57 | Protrusion, snapper |
| 58 | Holder for battery, motor |
| 59 | Guide piston rod |
| 59a | Keyway |
| 60 | Outside threading piston rod |
| 61 | Cartridge holder |
| 62 | Abutment surface |
| 63 | Receiving section |
| 64 | Sterile barrier needle unit |
| 65 | Key |
| 66 | Locking aperture |
| 67 | Housing needle unit |
| 68 | Cam shaft |
| 69 | Gear wheel cam shaft |

-continued

| PART ANNOTATION | |
|---|---|
| 70 | Pull tab |
| 71 | Slider |
| 71a | Extension |
| 71b | Abutment/locking surface |
| 71c | End extension |
| 72 | Locking fork slider |
| 73 | Linear keys slider |
| 74 | Linear guides to spring slider |
| 75 | Gear rack slider |
| 76 | Spring fixator |
| 77 | Aperture |
| 78 | Wing |
| 79 | Torsional spring |
| 80 | Lower leg |
| 81 | Upper leg |
| 82 | Coil |
| 83 | Upper spring slider |
| 84 | Lower spring slider |
| 85 | Skin needle holder |
| 86 | Linear keys |
| 87 | Skin needle |
| 88 | Tapered cartridge needle slider spring |
| 89 | Tube, conduit |
| 90 | Cartridge needle |
| 91 | Cartridge needle holder |
| 92 | Cartridge needle slider CNS |
| 93 | Guide |
| 94 | Mechanism holder |
| 94a | Protrusion |
| 94b | Abutment/locking surface |
| 95 | Keyways to guide CNS |
| 96 | Needle cover |
| 96a | Winglet |
| 97 | Sealing rim |
| 98 | Aperture skin needle |
| 99 | Barrier film |
| 100 | Gear wheel CT for gear rack |
| 101 | Fluid path compartment |
| 102 | Passage cam shaft |
| 102a | O-ring cam shaft |
| 102b | Passage cam shaft |
| 102c | V-ring |
| 103 | Slider compartment |
| 104 | Passage fluid path compartment |
| 105 | Guide mechanism holder to slider |
| 106 | Guide mechanism holder to skin needle holder |
| 107 | Receiving section upper spring slider |
| 108 | Receiving section for lower spring slider on skin needle holder |
| 109 | Locking member for lower spring slider on mechanism holder |
| 110 | Teeth gear rack |
| 111 | Stop surface to SNH |
| 112 | Spring holder |
| 113 | Receiving pocket |
| 114 | End section |
| 115 | Cut out |
| 116 | Base slider |
| 117 | Bridging bar |
| 118 | Abutment surface slider |
| 119 | Flexible arm spring holder |
| 120 | Key upper spring slider |
| 121 | Key lower spring slider |
| 122 | Receiving section |
| 123 | Opening for upper leg |
| 124 | Holding surface lower spring slider |
| 125 | Locking feature |
| 126a | Gearing surface |
| 126 | Knob |
| 127 | Aperture MH |
| 128 | Sealing surface |
| 129 | Circumferential rim |
| 130 | Aperture skin needle in MH |
| 131 | Aperture needle housing for sterile barrier film |
| 132 | Barrel |
| 133 | Distal opening |
| 134 | Proximal opening |

-continued

| | PART ANNOTATION |
|---|---|
| 135 | Neck |
| 136 | Sterile barrier film |
| 137 | Pull tab |
| 138 | Flip off cap |
| 139 | Crimp |
| 140 | Plunger |
| 141 | Septum |
| 142 | Spacer |
| 143 | Bearing surface |
| 144 | External fold |
| 145 | Internal fold |
| 146 | Connector |
| 147 | Predetermined breaking point |
| 148 | End surface |
| 149 | Aperture for cartridge needle |
| 150 | Notch RL |
| 151 | Legs U-shaped notch |
| 152 | Opening notch |
| 153 | Aperture RL skin needle |
| 154 | Conductive layer |
| 155 | Notch sensing patch unit |
| 156 | Aperture sensing patch unit |
| 157 | Contact points |
| 158 | Assembly |
| 159 | Adhesive top layer to HU |
| 160 | Sensor layer |
| 161 | Sensor area |
| 162 | Second sensor area |
| 163 | Lead |
| 164 | Contact |
| 165 | Backside surface RL |
| 166 | Adhesive spot |
| 167 | Second adhesive spot |
| 168 | Housing cover HC |
| 169 | Guiding rib |
| 170 | Closure rim |
| 171 | Housing base HB |
| 172 | Closing rim |
| 173 | Aperture skin needle |
| 174 | Notch HB |
| 175 | Support flange, snapper |
| 176 | Marks |
| 177 | Aperture HC push button |
| 178 | Guiding rib |
| 179 | Rib engager HC |
| 180 | Rib engager HB |
| 181 | Deformable ribs, arresters |
| 182 | Strengthening sheet |
| 183 | Contact surface spring slider to receiving section |
| 184 | Contact surface spring to slider |
| 185 | Sloped surface upper slider |
| 186 | End surface upper slider |
| 187 | Sloped surface lower slider |
| 188 | End surface lower slider |
| 189 | Connector |
| 190 | Lock protrusion |
| 191 | Skin adhesive layer |
| 192 | Opening housing cover |
| 193 | Slider release latch, intermediate member or part |
| 193a | Gearing surface |
| 193b | Opening |
| 193c | Flexible arm |
| 193d | Head, locking member |
| 193e | Abutment/locking surface |
| 194 | Welding seam |
| 195 | Partition wall |
| 196 | Shielding wall |
| 46, 39, 40, 35 | Gearing mechanism |
| 37, 26a | One-way ratchet |
| 71a, 193d, 94a | Lock |
| 193a, 126a | Gearing |

What is claimed is:

1. A needle insertion mechanism for an injection device comprising:

a needle holder holding a needle, the needle holder adapted to be advanced from a needle retracted position to a needle inserted position under a needle insertion bias;

a slider adapted to be moved from a first position retaining the needle holder in the retracted position, towards a second position allowing movement of the needle holder to the inserted position;

an intermediate member operatively arranged between the needle holder and the slider, the intermediate member configured to be moveable from a blocked position securing the needle holder in the retracted position to a release position releasing the needle holder for movement along a needle axis into the inserted position, wherein:

a biased gearing between the intermediate member and the needle holder is configured for biasing the intermediate member towards the release position, and a lock between the intermediate member and the slider is configured for locking the intermediate member in the blocked position against the bias of the biased gearing, and movement of the slider towards the second position unlocks the lock and the biased gearing moves the intermediate member into the release position thereby releasing the needle holder.

2. The needle insertion mechanism according to claim 1, further comprising a spring positioned between a housing of the needle insertion mechanism and the needle holder, wherein the spring is configured for providing the needle insertion bias.

3. The needle insertion mechanism according to claim 1, wherein the biased gearing comprises a gearing surface on the needle holder and a complementary gearing surface on the intermediate member.

4. The needle insertion mechanism according to claim 2, wherein the biased gearing comprises a gearing surface on the needle holder and a complementary gearing surface on the intermediate member.

5. The needle insertion mechanism according to claim 4, wherein the spring is configured to bias the biased gearing.

6. The needle insertion mechanism according to claim 4, wherein the gearing surface of the needle holder is arranged on a knob extending from the needle holder engaging the complementary gearing surface on a locking fork on the intermediate member.

7. The needle insertion mechanism according to claim 1, wherein the lock comprises a locking member on the intermediate member engaging a locking surface on the slider and/or a locking surface on a housing when the slider is in the first position.

8. The needle insertion mechanism according to claim 7, wherein the locking member and the locking surfaces are in a form-fit or in a friction fit engagement when the slider is in the first position.

9. The needle insertion mechanism according to claim 8, wherein the locking member is positioned between and abuts a locking surface on a protrusion on the slider in an abutment and abuts a locking surface on a protrusion on the housing in another abutment.

10. The needle insertion mechanism according to claim 9, wherein the locking member comprises at least one flexible arm present on the intermediate member and wherein an end of the flexible arm abuts the locking surfaces on the slider and/or on the housing.

11. The needle insertion mechanism according to claim 10, wherein the abutment between the locking member and the locking surface on the slider is released when the slider is moved from the first position towards the second position.

12. The needle insertion mechanism according to claim 11, wherein the flexible arm is flexed due to a movement of the intermediate member towards the release position by the biased gearing thereby releasing the another abutment between the locking surface on the housing and the locking member and unlocking the lock.

13. The needle insertion mechanism according to claim 1, wherein at least one of the intermediate member and the slider is guided by the housing in a movement perpendicular to a longitudinal axis.

14. The needle insertion mechanism according to claim 13, wherein the intermediate member and the slider are configured to be moved in opposite directions.

15. The needle insertion mechanism according to claim 1, wherein the slider is adapted to be moved by an electric motor.

16. A patch injection device comprising the needle insertion mechanism of claim 1.

17. A patch infusion device comprising the needle insertion mechanism of claim 1.

18. A patch injection device comprising the needle insertion mechanism of claim 11.

19. A patch injection device comprising the needle insertion mechanism of claim 15.

* * * * *